(12) United States Patent
Gray et al.

(10) Patent No.: US 10,793,844 B2
(45) Date of Patent: Oct. 6, 2020

(54) AMYLASES, NUCLEIC ACIDS ENCODING THEM AND METHODS FOR MAKING AND USING THEM

(71) Applicant: BASF Enzymes LLC, San Diego, CA (US)

(72) Inventors: Kevin A. Gray, San Diego, CA (US); Nahla M. Aboushadi, Oceanside, CA (US); James B. Garrett, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

(21) Appl. No.: 16/154,205

(22) Filed: Oct. 8, 2018

(65) Prior Publication Data

US 2019/0062715 A1 Feb. 28, 2019

Related U.S. Application Data

(62) Division of application No. 14/971,255, filed on Dec. 16, 2015, now Pat. No. 10,100,293, which is a division of application No. 14/012,532, filed on Aug. 28, 2013, now Pat. No. 9,249,400, which is a division of application No. 13/283,119, filed on Oct. 27, 2011, now Pat. No. 9,551,754, which is a division of application No. 12/756,079, filed on Apr. 7, 2010, now Pat. No. 8,071,350, which is a division of application No. 10/532,944, filed as application No. PCT/US03/33150 on Oct. 15, 2003, now Pat. No. 7,741,092.

(60) Provisional application No. 60/423,626, filed on Oct. 31, 2002.

(51) Int. Cl.

| | |
|---|---|
| *C12N 9/26* | (2006.01) |
| *A23L 29/00* | (2016.01) |
| *A23L 29/30* | (2016.01) |
| *A23K 20/189* | (2016.01) |
| *A23K 10/14* | (2016.01) |
| *C12N 9/28* | (2006.01) |
| *A21D 8/04* | (2006.01) |
| *C11D 3/386* | (2006.01) |
| *C12C 5/00* | (2006.01) |
| *C12N 9/34* | (2006.01) |
| *C12N 9/44* | (2006.01) |

(52) U.S. Cl.
CPC ............ *C12N 9/2411* (2013.01); *A21D 8/042* (2013.01); *A23K 10/14* (2016.05); *A23K 20/189* (2016.05); *A23L 29/06* (2016.08); *A23L 29/35* (2016.08); *C11D 3/386* (2013.01); *C12C 5/004* (2013.01); *C12N 9/2417* (2013.01); *C12N 9/2428* (2013.01); *C12N 9/2451* (2013.01); *C12Y 302/01001* (2013.01); *C12Y 302/01002* (2013.01); *A23V 2002/00* (2013.01); *C12Y 302/01* (2013.01); *Y02E 50/17* (2013.01)

(58) Field of Classification Search
CPC .................. A21D 8/042; C12Y 302/01; C12Y 302/01001; C12Y 302/01002; C12C 5/004; C12N 9/2411; C12N 9/2428; C12N 9/2451; C12N 9/2417; Y02E 50/17; A23K 20/189; A23K 10/14; A23L 29/06; A23L 29/35; A23V 2002/00; C11D 3/386

See application file for complete search history.

(56) References Cited

U.S. PATENT DOCUMENTS

| | | | |
|---|---|---|---|
| 5,093,257 A | 3/1992 | Gray | |
| 6,297,037 B1 | 10/2001 | Barnett | |
| 7,273,740 B2 | 9/2007 | Callen | |
| 8,551,754 B2 * | 10/2013 | Gray | ...... A21D 8/042 |
| | | | 435/202 |
| 8,841,107 B2 | 9/2014 | Power | |
| 2001/0053519 A1 | 12/2001 | Fodor | |
| 2003/0125534 A1 * | 7/2003 | Callen | ........ C12N 9/2417 |
| | | | 536/23.1 |
| 2015/0001770 A1 | 1/2015 | Power | |

FOREIGN PATENT DOCUMENTS

| | | |
|---|---|---|
| CN | 1222938 A | 7/1999 |
| EP | 0252666 B1 | 6/1993 |
| JP | 62-104580 A2 | 5/1987 |
| WO | 1993000426 A1 | 1/1993 |
| WO | 99/67408 A1 | 12/1999 |
| WO | 1999067406 A1 | 12/1999 |
| WO | 2002/029079 A2 | 11/2002 |
| WO | 2003012071 A2 | 2/2003 |

OTHER PUBLICATIONS

Broun—Science (1998) 282:1315-1317.
Guo—PNAS USA (2004) 101-9205-9210.
Kim—FEMS Microbiol. Lett. (1996)—138-147-152.
Laderman—J. of Biol. Chem. (1993)—268(32):24394-24401.
Malhotra—Lett. Appl. Microbiol. (2000) 31:378-384.
Narang—Lett. Appl. Microbiol. (2001) 32: 31-35.

(Continued)

*Primary Examiner* — Ganapathirama Raghu
(74) *Attorney, Agent, or Firm* — Richa Dhindsa

(57) ABSTRACT

In one aspect, the invention is directed to polypeptides having an amylase activity, polynucleotides encoding the polypeptides, and methods for making and using these polynucleotides and polypeptides. The polypeptides of the invention can be used as amylases to catalyze the hydrolysis of starch into sugars.

13 Claims, 4 Drawing Sheets
Specification includes a Sequence Listing.

(56) References Cited

OTHER PUBLICATIONS

Seffernick—J. of Bacteriol. (2001) 183(8):2405-2410.
Whisstock—Biophysics. (2003) 36 (3): 307-340.
Witkowski—Biochemistry (1999) 38:11643-11650.
Hulsmann—J. Bacteriol. (2000)—22-6292-6301.
Brown—Nature Genetics (1999)—21-33-37.
Bult—Science (1996)—273-1058-1073.
WIPO—PCT/US2003/33150—Search Report—Dec. 20, 2004.
Ausubel—Current Protocols in Molecular Biology, Chapters 1-3, 16 and Vectors-Appendix 5, John Wiley & Sons, New York, NY (1990)—Havel.
Gray—Journal of Bacteriology—(1986)—166-2-635-643.
JPO—Aug. 16, 2012⇒Office Action—JP2010-132602.
JPO—Dec. 20, 2012—Office Action—JP2011-022288.
SIPO—Oct. 12, 2012—Decision of Final Rejection & Translation—CN200910224585.4.
SIPO—Feb. 4, 2013—First Office Action and Translation—CN201210020583.5.
AUIPO—Dec. 6, 2013—Examiner's First Report—2012238328.
BPTO—Mar. 23, 2014—Office Action—PI0207770-1.
BPTO—Sep. 9, 2014—Office Action—PI0207770-1.
CIPO—Sep. 25, 2013—Office Action—CA 2,515,340.
CIPO—May 28, 2014—Examiner's Requisition—CA 2, 438, 205.
CIPO—Feb. 18, 2015—Examiner's First Requisition—CA 2,833,423.
EMBL Accession No. AAK17994 (2001).
EPO—Oct. 14, 2013—Art. 94(3) Communication—EP07869797.6.
EPO—Apr. 22, 2014—94(3) Communication—10 184 478.5.
EPO—Apr. 29, 2014—94(3) Communication—10 182 415.7.
EPO—May 13, 2014—94(3) Communication—09 171 688.6.
EPO—Dec. 22, 2014—94(3) Communication—10 184 415.7.
Genbank Accession No. AB115912—Watanabe (2003).
Genbank Accession No. AF032864.1—Da Silva—(1997).
Genbank Accession No. M38570.1—Udaka—(1993).
JPO—Feb. 5, 2014—Second Office Action—JP2011-022288.
Kim—Biotechnology Letters (1996)—18-169-174.
Robertson—Applied and Environmental Microbiology (2004)—70-2429-2436.
Saponins—Discover the Wealth of Benefits Saponins Provide—Ecological Surfactants, Inc. http://www.ecologicalsurfactants.com/saponin/—Retrieved Mar. 13, 2014.
SIPO—Sep. 11, 2013—Second Office Action—CN201210020583.5.
SIPO—Feb. 20, 2014—Third Office Action—CN201210020583.5.
SIPO—Mar. 5, 2014—Fourth Office Action and Translation—CN200910224585.4.
Surfactants: the ubiquitous amphiphiles—Royal Society of Chemistry, Chemistry World, http://www.rsc.org/chemistryworld/issues/2003/july/amphiphiles.asp (2003)—Retrieved Mar. 13, 2014.
USPTO—Oct. 29, 2013—Office Action, 892, IDSs considered U.S. Appl. No. 13/669,707.
USPTO—Mar. 20, 2014—Office Action, 892, Refs Considered—U.S. Appl. No. 13/482,919.
Chica—Curr. Opin. Biotechnol. (2005)—4-378-384.
Devos—Proteins: Structure, Function, and Genetics (2000)—41-98-107.
SEN—Appl. Biochem. Biotechnol (2007)—2-212-223.
EPO—EP10184415.7—Partial EP Search Report—dated Apr. 6, 2011.
EPO—EP10184381.1—EP Partial EP Search Report—dated May 24, 2011.
Uniprot Accession No. Q59222—Lin—1996.
Genbank Accession No. U22045—Lin—1995.
JP2008-136876—Office Action—dated Jun. 2, 2011.
USPTO—Jun. 10, 2011—Final Office Action—U.S. Appl. No. 12/567,550.
Uniprot Accession No. Q52413—Kim—1996.
AUIP—2010246342—Examiner's First Report—dated Jun. 8, 2011.
AUIP—2010246342—Examiner's Second Report—dated Aug. 18, 2011.
AUIP—2009222426—Examiner's Second Report—dated Aug. 22, 2011.
AUIP—2009222426—Examiner's First Report—dated Jul. 4, 2011.
Lin—Journal of Applied Microbiology—(1997)—82-325-334.
Lin—Letters in Applied Microbiology—(1997)—24-365-368.
Genbank Accession No. CAB88152 (Apr. 19, 2000).
EPO—10184415.7—Extended EP Search Report—dated Aug. 9, 2011.
SIPO—Aug. 15, 2011—Decision of Rejection—CN200480012052.5.
SIPO—Aug. 23, 2011—First Office Action—CN200910224585.4.
EPO—EP10184478.5—Extended EP Search Report—dated Aug. 9, 2011.
JP2008-136876—Office Action—Jun. 2, 2011.
EPO—10184415.7—Extended EP Search Report—Aug. 9, 2011.
EPO—EP10184478.5—Extended EP Search Report—Aug. 9, 2011.
U.S. Appl. No. 12/822,413—Office Action—Oct. 12, 2011.
EPO—May 29, 2012—Extended EP Search Report—EP12152662.8.
EPO—May 29, 2012—Extended EP Search Report—EP12152656.0.
Uniprot Accession No. Q0C881—Birren—2006.
EBI Accession No. EAU29552—Aspergillus terreus NIH2624—2006.
EBI Accession No. ABB80178—Jiang—2003.
Geneseq Accession No. ABQ80348—Jiang—2003.
Uniprot Accession No. QOCPK9—Birren—2006.
NCBI Accession No. EAU34822—Aspergillus terreus NIH2624 glucoamylase precursor—2006.
Geneseq Accession No. ABB80181—Jiang—2003.
Geneseq Accession No. ABQ80354—Jiang—2003.
EPO—Feb. 7, 2012—94(3) Communication—EP09171688.6.
EPO—Mar. 7, 2012—94(3) Communication—EP10182375.5.
EPO—Mar. 15, 2012—94(3) Communication—EP09180956.6.
EPO—May 2, 2012—94(3) Communication—EP10184415.7.
EPO—May 2, 2012—94(3) Communication—EP10184478.5.
Hu—Journal of General Microbiology (1992)—138-1647-1655.
INPO—Jun. 7, 2012—First Examination Report—3819/KOLNP/2008.
JPO—May 14, 2012—Office Action—JP2010-135846.
USPTO—Apr. 30, 2012—Office Action—U.S. Appl. No. 12/520,523.
Wishart—Journal of Biological Chemistry—(1995)—270-26782-26785.
CIPO—Jan. 9, 2012—Office Action—CA2438205.
USPTO—Nov. 16, 2011—Final Office Action—U.S. Appl. No. 12/567,550.
CIPO—Nov. 14, 2011—Office Action—CA2515340.
EPO—EP07869797.9—Office Action—dated Dec. 13, 2011.

\* cited by examiner

AMYLASES, NUCLEIC ACIDS ENCODING THEM AND METHODS FOR MAKING AND USING THEM

CROSS-REFERENCE TO RELATED APPLICATIONS

This application is a divisional of U.S. patent application Ser. No. 14/971,255, filed Dec. 16, 2015, now U.S. Pat. No. 10,100,293, granted on Oct. 16, 2018; which is a divisional of U.S. Ser. No. 14/012,532, filed Aug. 28, 2013, now U.S. Pat. No. 9,249,400; which is a Divisioinal of U.S. Ser. No. 13/283,119, filed Oct. 27, 2011, now U.S. Pat. No. 8,551,754, granted on Oct. 8, 2013; which is a Divisional of U.S. Ser. No. 12/756,079, filed Apr. 7, 2010, now U.S. Pat. No. 8,071,350, granted Dec. 6, 2011; which is a Divisional of U.S. Ser. No. 10/532,944, filed Jun. 21, 2006, now U.S. Pat. No. 7,741,092, granted on Jun. 22, 2010; which is a national phase application claiming benefit of priority under 35 U.S.C. § 371 to Patent Convention Treaty (PCT) International Application Serial No: PCT/US2003/033150, filed Oct. 15, 2003 (published as WO 2004/042006, on May 21, 2004), which claims benefit of priority to U.S. Provisional Patent Application Ser. No. 60/423,626, filed Oct. 31, 2002. The aforementioned applications are all explicitly incorporated herein by reference in their entirety and for all purposes.

REFERENCE TO SEQUENCE LISTING SUBMITTED VIA EFS-WEB

This application includes a nucleotide and amino acid sequence listing in computer readable from (CRF) and conforming to the requirements of 37 C.F.R. 1.821 through 1.825. The sequence listing of this application is being submitted to the USPTO via the EFS-WEB server as authorized and set forth in MPEP § 502.05. The sequence listing of this application is filed in an ASC II text (.txt) file as identified below and is hereby incorporated by reference into the specification of this application in its entirety and for all purposes.

| File Name | Date of Creation | Size (bytes) |
|---|---|---|
| SequenceListing.txt | Sep. 10, 2018 | 58.7 KB (60,205 bytes) |

TECHNICAL FIELD

This invention relates to molecular and cellular biology and biochemistry. In one aspect, the invention is directed to polypeptides having an amylase activity, polynucleotides encoding the polypeptides, and methods for making and using these polynucleotides and polypeptides. The polypeptides of the invention can be used as amylases to catalyze the hydrolysis of starch into sugars.

BACKGROUND

Amylase is an enzyme that catalyzes the hydrolysis of starches into sugars. Amylases can hydrolyze internal alpha-1, 4-glucosidic linkages in starch, largely at random, to produce smaller molecular weight malto-dextrins. The product of hydrolysis of one amylase, alpha-amylase (α-amylase) can be maltose, maltotriose or α-dextrin. These polysaccharides can be converted to glucose by the action of other enzymes including, for example, beta-amylase (β-amylase). Some β-amylases hydrolyze residues at the non-reducing terminus of the polysaccharide.

Amylases can be used commercially in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper and in animal feed. Amylases are also useful in textile desizing, brewing processes, starch modification in the paper and pulp industry and other processes.

SUMMARY

The invention provides isolated or recombinant nucleic acids comprising a nucleic acid sequence having at least about 85%, 86%, 87%, 88%, 89%, 90%, 91%, 92%, 93%, 94%, 95%, 96%, 97%, 98%, 99%, or more, or complete (100%) sequence identity to SEQ ID NO:5 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more, residues, wherein the nucleic acid encodes at least one polypeptide having an amylase activity, and the sequence identities are determined by analysis with a sequence comparison algorithm or by a visual inspection.

The invention provides isolated or recombinant nucleic acids comprising a nucleic acid sequence having at least about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:7 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more, residues, wherein the nucleic acid encodes at least one polypeptide having an amylase activity, and the sequence identities are determined by analysis with a sequence comparison algorithm or by a visual inspection.

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%), sequence identity to SEQ ID NO:11 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more, or more, residues, wherein the nucleic acid encodes at least one polypeptide having an amylase activity, and the sequence identities are determined by analysis with a sequence comparison algorithm or by a visual inspection.

The invention provides isolated or recombinant nucleic acids comprising a nucleic acid sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:13 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more, residues, wherein the nucleic acid encodes at least one polypeptide having an amylase activity, and the sequence identities are determined by analysis with a sequence comparison algorithm or by a visual inspection.

The invention provides isolated or recombinant nucleic acids comprising a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:15 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more, residues, wherein the nucleic acid encodes at least one polypeptide having an amylase activity, and the sequence identities are determined by analysis with a sequence comparison algorithm or by a visual inspection.

In one aspect, the invention provides isolated or recombinant nucleic acids, wherein the nucleic acid sequence comprises a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof.

In one aspect, the invention provides isolated or recombinant nucleic acids, wherein the nucleic acid sequence encodes a polypeptide comprising a polypeptide having a sequence as set forth in SEQ ID NO:2, SEQ ID NO:4, SEQ ID NO:6, SEQ ID NO:8, SEQ ID NO:10, SEQ ID NO:12, SEQ ID NO:14 or SEQ ID NO:16, or a subsequence or fragment thereof.

In one aspect, the sequence comparison algorithm is a BLAST version 2.2.2 algorithm where a filtering setting is set to blastall −p blastp −d "nr pataa"−F F, and all other options are set to default.

In one aspect, the amylase activity comprises hydrolyzing glucosidic bonds. The amylase activity can comprise a glucoamylase activity, a 1,4-α-D-glucan glucohydrolase activity, an α-amylase activity, an exoamylase activity, or a β-amylase activity. In one aspect, the glucosidic bonds comprise an α-1,4-glucosidic bond. In another aspect, the glucosidic bonds comprise an α-1,6-glucosidic bond. In one aspect, the amylase activity comprises hydrolyzing glucosidic bonds in starch, e.g., liquefied starch. The amylase activity can further comprise hydrolyzing glucosidic bonds into maltodextrines. In one aspect, the amylase activity comprises cleaving a maltose or a D-glucose unit from non-reducing end of the starch.

In one aspect, the isolated or recombinant nucleic acid encodes a polypeptide having an amylase activity which is thermostable. The polypeptide can retain an amylase activity under conditions comprising a temperature range of between about 37° C. to about 95° C.; between about 55° C. to about 85° C., between about 70° C. to about 95° C., or, between about 90° C. to about 95° C.

In another aspect, the isolated or recombinant nucleic acid encodes a polypeptide having an amylase activity which is thermotolerant. The polypeptide can retain an amylase activity after exposure to a temperature in the range from greater than 37° C. to about 95° C. or anywhere in the range from greater than 55° C. to about 85° C. In one aspect, the polypeptide retains an amylase activity after exposure to a temperature in the range from greater than 90° C. to about 95° C. at pH 4.5.

The invention provides isolated or recombinant nucleic acids comprising a sequence that hybridizes under stringent conditions to a nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof. In one aspect, the nucleic acid encodes a polypeptide having an amylase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide having an amylase activity, wherein the probe comprises at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more, consecutive bases of a sequence comprising a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof.

The invention provides a nucleic acid probe for identifying a nucleic acid encoding a polypeptide having an amylase activity, wherein the probe comprises/consists of a nucleic acid of the invention (which includes both sense and antisense strands) that is at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues. In one aspect, the probe has at least about 99.5% or more sequence identity to SEQ ID NO:1, wherein the sequence identities are determined by analysis with a sequence comparison algorithm or by visual inspection.

The invention provides a nucleic acid probe for identifying a nucleic acid encoding a polypeptide having an amylase activity, wherein the probe comprises/consists of a sequence of the invention at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues. In one aspect, the probe comprises at least about 99.5% or more sequence identity to SEQ ID NO:3, wherein the sequence identities are determined by analysis with a sequence comparison algorithm or by visual inspection.

In one aspect, the invention provides a nucleic acid probe for identifying a nucleic acid encoding a polypeptide having an amylase activity, wherein the probe comprises a nucleic acid sequence having at least about 90%, 91%, 92%, 93%, 94%, 95%, 96%, 97%, 98%, 99%, or more, or complete (100%), sequence identity to SEQ ID NO:5 over a region of at least about 100, 200, 300, 400, 500, 600, 700, 800, 900, 1000, 1100, 1200, 1300, 1400, 1500 or more residues, wherein the sequence identities are determined by analysis with a sequence comparison algorithm or by a visual inspection.

The invention provides a nucleic acid probe for identifying a nucleic acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:7 over a region of at least about 100, 200, 300, 400, 500, 600, 700, 800, 900, 1000, 1100, 1200, 1300, 1400, 1500 or more residues, wherein the sequence identities are determined by analysis with a sequence comparison algorithm or by a visual inspection.

The invention provides a nucleic acid probe for identifying a nucleic acid encoding a polypeptide having an amylase activity, wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues having at least about 99.5% or more sequence identity to SEQ ID NO:9, wherein the sequence identities are determined by analysis with a sequence comparison algorithm or by visual inspection.

The invention provides a nucleic acid probe for identifying a nucleic acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:11 over a region of at least about 100, 200, 300, 400, 500, 600, 700, 800, 900, 1000, 1100, 1200, 1300, 1400, 1500 or more residues, wherein the sequence identities are determined by analysis with a sequence comparison algorithm or by a visual inspection.

The invention provides a nucleic acid probe for identifying a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, or more, or complete sequence identity to SEQ ID NO:13 over a region of at least about 100, 200, 300, 400, 500, 600, 700, 800, 900, 1000, 1100, 1200, 1300, 1400, 1500 or more residues, wherein the sequence identities are determined by analysis with a sequence comparison algorithm or by a visual inspection.

The invention provides a nucleic acid probe for identifying a nucleic acid sequence having at least 90%, 91%, 92%, 93%, 94%, 95%, 96%, 97%, 98%, 99%, or more, or complete sequence identity to SEQ ID NO:15 over a region of at least about 100, 200, 300, 400, 500, 600, 700, 800, 900, 1000, 1100, 1200, 1300, 1400, 1500 or more residues, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof.

The invention provides an amplification primer sequence pair for amplifying a nucleic acid encoding a polypeptide having an amylase activity, wherein the primer pair is capable of amplifying a nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, 25, 26, 27, 28, 29, 30 or more consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30 or more residues of the complementary strand of the first member.

The invention provides amylase-encoding nucleic acids generated by amplification, e.g., polymerase chain reaction (PCR), using an amplification primer pair of the invention. The invention provides amylases generated by amplification, e.g., polymerase chain reaction (PCR), using an amplification primer pair of the invention. The invention provides methods of making amylases by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having an amylase activity comprising amplification of a template nucleic acid with an amplification primer sequence pair capable of amplifying a nucleic acid sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or fragments or subsequences thereof.

The invention provides expression cassettes comprising a nucleic acid of the invention, e.g., a nucleic acid comprising: (i) a sequence as set forth in SEQ ID NO:1, a nucleic acid sequence having at least 90% sequence identity to SEQ ID NO:5 over a region of at least about 100 residues, a nucleic acid sequence having at least 60% sequence identity to SEQ ID NO:7 over a region of at least about 100 residues, a nucleic acid sequence having at least 50% sequence identity to SEQ ID NO:11 over a region of at least about 100 residues, a nucleic acid sequence having at least 70% sequence identity to SEQ ID NO:13 over a region of at least about 100 residues, or a nucleic acid sequence having at least 80% sequence identity to SEQ ID NO:15 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof.

In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or a environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides vectors comprising a nucleic acid of the invention, e.g., a nucleic acid comprising (i) a sequence as set forth in SEQ ID NO:1, a nucleic acid sequence having at least 90% sequence identity to SEQ ID NO:5 over a region of at least about 100 residues, a nucleic acid sequence having at least 60% sequence identity to SEQ ID NO:7 over a region of at least about 100 residues, a nucleic acid sequence having at least 50% sequence identity to SEQ ID NO:11 over a region of at least about 100 residues, a nucleic acid sequence having at least 70% sequence identity to SEQ ID NO:13 over a region of at least about 100 residues, or a nucleic acid sequence having at least 80% sequence identity to SEQ ID NO:15 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention, e.g., a nucleic acid comprising (i) a sequence as set forth in SEQ ID NO:1, a nucleic acid sequence having at least 90% sequence identity to SEQ ID NO:5 over a region of at least about 100 residues, a nucleic acid sequence having at least 60% sequence identity to SEQ ID NO:7 over a region of at least about 100 residues, a nucleic acid sequence having at least 50% sequence identity to SEQ ID NO:11 over a region of at least about 100 residues, a nucleic acid sequence having at least 70% sequence identity to SEQ ID NO:13 over a region of at least about 100 residues, or a nucleic acid sequence having at least 80% sequence identity to SEQ ID NO:15 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell.

The invention provides transgenic non-human animals comprising a nucleic acid of the invention or an expression cassette (e.g., a vector) of the invention. In one aspect, the animal is a mouse.

The invention provides transgenic plants comprising a nucleic acid of the invention or an expression cassette (e.g., a vector) of the invention. The transgenic plant can be a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid of the invention or an expression cassette (e.g., a vector) of the invention. The transgenic seed can be a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention, e.g., (i) a sequence as set forth in SEQ ID NO:1, or a subsequence thereof; a sequence as set forth in SEQ ID NO:3, or a subsequence thereof; a nucleic acid sequence having at least 90% sequence identity to SEQ ID NO:5 over a region of at least about 100 residues, or a subsequence thereof; a nucleic acid sequence having at least 60% sequence identity to SEQ ID NO:7 over a region of at least about 100 residues, or a subsequence thereof; a nucleic acid sequence having at least 50% sequence identity to SEQ ID NO:11 over a region of at least about 100 residues, or a subsequence thereof; a nucleic acid sequence having at least 70% sequence identity to SEQ ID NO:13 over a region of at least about 100 residues, or a subsequence thereof; or a nucleic acid sequence having at least 80% sequence identity to SEQ ID NO:15 over a region of at least about 100 residues, or a subsequence thereof; wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof. The antisense oligonucleotide can be between about 10 to 50, about 20 to 60, about 30 to 70, about 40 to 80, or about 60 to 100 bases in length.

The invention provides methods of inhibiting the translation of an amylase message in a cell comprising administering to the cell or expressing in the cell an antisense oligonucleotide comprising a nucleic acid sequence complementary to or capable of hybridizing under stringent conditions to a nucleic acid of the invention.

The invention provides methods of inhibiting the translation of an amylase message in a cell comprising administering to the cell or expressing in the cell an antisense oligonucleotide comprising a nucleic acid sequence complementary to or capable of hybridizing under stringent conditions to a nucleic acid of the invention. The invention provides double-stranded inhibitory RNA (RNAi) molecules comprising a subsequence of a sequence of the invention. In one aspect, the RNAi is about 15, 16, 17, 18, 19, 20, 21, 22, 23, 24, 25 or more duplex nucleotides in length. The invention provides methods of inhibiting the expression of an amylase in a cell comprising administering to the cell or expressing in the cell a double-stranded inhibitory RNA (iRNA), wherein the RNA comprises a subsequence of a sequence of the invention.

The invention provides an isolated or recombinant polypeptide comprising: (a) an amino acid sequence having at least 99.5% or more, identity to SEQ ID NO:2 over a region of at least about 10, 20, 30, 40, 50, 60, 70, 80, 90, 100, 150, 200, 250, 300, 350, 400, 450, 500, 550, or more, residues, or, an amino acid sequence as set forth in SEQ ID NO:2, an amino acid sequence having at least 90%, 91%, 92%, 93%, 94%, 95%, 96%, 97%, 98%, 99%, or more, or complete (100%) identity to SEQ ID NO:6 over a region of at least about 10, 20, 30, 40, 50, 60, 70, 80, 90, 100, 150, 200, 250, 300, 350, 400, 450, 500, 550, or more, residues; an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) identity to SEQ ID NO:8 over a region of at least about 10, 20, 30, 40, 50, 60, 70, 80, 90, 100, 150, 200, 250, 300, 350, 400, 450, 500, 550, or more, residues, an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) identity to SEQ ID NO:12 over a region of at least about 10, 20, 30, 40, 50, 60, 70, 80, 90, 100, 150, 200, 250, 300, 350, 400, 450, 500, 550, or more, residues; an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) identity to SEQ ID NO:14 over a region of at least about 10, 20, 30, 40, 50, 60, 70, 80, 90, 100, 150, 200, 250, 300, 350, 400, 450, 500, 550, or more, residues; or an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) identity to SEQ ID NO:16 over a region of at least about 10, 20, 30, 40, 50, 60, 70, 80, 90, 100, 150, 200, 250, 300, 350, 400, 450, 500, 550, or more, residues, or (b) a polypeptide encoded by a nucleic acid comprising (i) a nucleic acid sequence as set forth in SEQ ID NO:1, a nucleic acid sequence having at least 90% sequence identity to SEQ ID NO:5 over a region of at least about 100 residues, a nucleic acid sequence having at least 60% sequence identity to SEQ ID NO:7 over a region of at least about 100 residues, a nucleic acid sequence having at least 50% sequence identity to SEQ ID NO:11 over a region of at least about 100 residues, a nucleic acid sequence having at least 70% sequence identity to SEQ ID NO:13 over a region of at least about 100 residues, or a nucleic acid sequence having at least 80% sequence identity to SEQ ID NO:15 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:5, or a subsequence thereof, a sequence as set forth in SEQ ID NO:7, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof. In one aspect, the polypeptide has an amylase activity.

The invention provides an isolated or recombinant polypeptide or peptide, wherein the polypeptide or peptide comprises an amino acid sequence as set forth in SEQ ID NO:2, SEQ ID NO:4, SEQ ID NO:6, SEQ ID NO:8, SEQ ID NO:10, SEQ ID NO:12, SEQ ID NO:14 or SEQ ID NO:16, or a subsequence or fragment thereof. Another aspect of the invention provides an isolated or recombinant polypeptide or peptide including at least 10, 15, 20, 25, 30, 35, 40, 45, 50, 55, 60, 65, 70, 75, 80, 85, 90, 95 or 100 or more consecutive bases of a polypeptide or peptide sequence of the invention, sequences substantially identical thereto, and the sequences complementary thereto. The peptide can be, e.g., an immunogenic fragment, a motif (e.g., a binding site), a signal sequence (e.g., as in Table 4), a prepro sequence or an active site.

In one aspect, the amylase activity comprises hydrolyzing glucosidic bonds. The amylase activity can comprise a glucoamylase activity, a 1,4-α-D-glucan glucohydrolase activity, an α-amylase activity, an exoamylase activity, or a β-amylase activity. In one aspect, the glucosidic bonds comprise an α-1,4-glucosidic bond or an α-1,6-glucosidic bond. In one aspect, the amylase activity comprises hydrolyzing glucosidic bonds in starch, e.g., liquefied starch. The amylase activity can further comprise hydrolyzing glucosidic bonds into maltodextrines. In one aspect, the amylase activity comprises cleaving a maltose or a D-glucose unit from non-reducing end of the starch.

In one aspect, the amylase activity can be thermostable. The polypeptide can retain an amylase activity under conditions comprising a temperature range of between about 37° C. to about 95° C., between about 55° C. to about 85° C., between about 70° C. to about 95° C., or between about 90° C. to about 95° C. In another aspect, the amylase activity can be thermotolerant. The polypeptide can retain an amylase activity after exposure to a temperature in the range from greater than 37° C. to about 95° C., or in the range from greater than 55° C. to about 85° C. In one aspect, the polypeptide can retain an amylase activity after exposure to a temperature in the range from greater than 90° C. to about 95° C. at pH 4.5.

In one aspect, the isolated or recombinant polypeptide can comprise the polypeptide of the invention that lacks a signal sequence. In one aspect, the isolated or recombinant polypeptide can comprise the polypeptide of the invention comprising a heterologous signal sequence, such as a heterologous amylase or non-amylase signal sequence. In one aspect, the invention provides a signal sequence comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 (or a longer peptide) of a polypeptide of the invention.

In one aspect, the invention provides chimeric proteins comprising a first domain comprising a signal sequence of the invention and at least a second domain. The protein can be a fusion protein. The second domain can comprise an enzyme. The enzyme can be an amylase or another enzyme.

The invention provides chimeric polypeptides comprising at least a first domain comprising signal peptide (SP), a prepro sequence and/or a catalytic domain (CD) of the invention and at least a second domain comprising a heterologous polypeptide or peptide, wherein the heterologous polypeptide or peptide is not naturally associated with the signal peptide (SP), prepro sequence and/or catalytic domain (CD). In one aspect, the heterologous polypeptide or peptide is not an amylase. The heterologous polypeptide or peptide can be amino terminal to, carboxy terminal to or on both ends of the signal peptide (SP), prepro sequence and/or catalytic domain (CD).

The invention provides isolated or recombinant nucleic acids encoding a chimeric polypeptide, wherein the chimeric polypeptide comprises at least a first domain comprising signal peptide (SP), a prepro domain and/or a catalytic domain (CD) of the invention and at least a second domain comprising a heterologous polypeptide or peptide, wherein the heterologous polypeptide or peptide is not naturally associated with the signal peptide (SP), prepro domain and/or catalytic domain (CD).

In one aspect, the amylase activity comprises a specific activity at about 37° C. in the range from about 100 to about 1000 units per milligram of protein. In another aspect, the amylase activity comprises a specific activity from about 500 to about 750 units per milligram of protein. Alternatively, the amylase activity comprises a specific activity at 37° C. in the range from about 500 to about 1200 units per milligram of protein. In one aspect, the amylase activity comprises a specific activity at 37° C. in the range from about 750 to about 1000 units per milligram of protein. In another aspect, the thermotolerance comprises retention of at least half of the specific activity of the amylase at 37° C. after being heated to the elevated temperature. Alternatively, the thermotolerance can comprise retention of specific activity at 37° C. in the range from about 500 to about 1200 units per milligram of protein after being heated to the elevated temperature.

The invention provides the isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a P. pastoris or a S. pombe.

In one aspect, the polypeptide can retain an amylase activity under conditions comprising about pH 6.5, pH 6, pH 5.5, pH 5, pH 4.5 or pH 4 or less. In another aspect, the polypeptide can retain an amylase activity under conditions comprising about pH 7, pH 7.5 pH 8.0, pH 8.5, pH 9, pH 9.5, pH 10, pH 10.5 or pH 11 or more. In one aspect, the polypeptide can retain an amylase activity after exposure to conditions comprising about pH 6.5, pH 6, pH 5.5, pH 5, pH 4.5 or pH 4 or less. In another aspect, the polypeptide can retain an amylase activity after exposure to conditions comprising about pH 7, pH 7.5 pH 8.0, pH 8.5, pH 9, pH 9.5, pH 10, pH 10.5 or pH 11 or more.

The invention provides protein preparations comprising a polypeptide of the invention, wherein the protein preparation comprises a liquid, a solid or a gel.

The invention provides heterodimers comprising a polypeptide of the invention and a second protein or domain. The second member of the heterodimer can be a different amylase, a different enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having an amylase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides food supplements for an animal comprising a polypeptide of the invention or a polypeptide encoded by the nucleic acid of the invention, e.g., a polypeptide comprising an amino acid sequence having at least 90% identity to SEQ ID NO:2, SEQ ID NO:4, SEQ ID NO:6, SEQ ID NO:8, SEQ ID NO:10, SEQ ID NO:12, SEQ ID NO:14 or SEQ ID NO:16, or a subsequence or fragment thereof over a region of at least about 100 residues; or a polypeptide encoded by a nucleic acid comprising a nucleic acid sequence having at least 90% identity to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a nucleic acid that hybridizes under stringent conditions to a nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or a subsequence thereof. In one aspect, the polypeptide can be glycosylated.

The invention provides edible enzyme delivery matrices comprising a polypeptide of the invention or a polypeptide encoded by the nucleic acid of the invention, e.g., a polypeptide comprising an amino acid sequence having at least 90% identity to SEQ ID NO:2, SEQ ID NO:4, SEQ ID NO:6, SEQ ID NO:8, SEQ ID NO:10, SEQ ID NO:12, SEQ ID NO:14 or SEQ ID NO:16, or a subsequence or fragment thereof over a region of at least about 100 residues; or a polypeptide encoded by a nucleic acid comprising a nucleic acid sequence having at least 90% identity to SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or a nucleic acid that hybridizes under stringent conditions to a nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13 or SEQ ID NO:15, or a subsequence thereof. In one aspect, the delivery matrix comprises a pellet. In one aspect, the polypeptide can be glycosylated. In one aspect, the amylase activity is thermotolerant. In another aspect, the amylase activity is thermostable.

The invention provides method of isolating or identifying a polypeptide having an amylase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having an amylase activity.

The invention provides methods of making an anti-amylase antibody comprising administering to a non-human animal a nucleic acid of the invention or a polypeptide of the invention or subsequences thereof in an amount sufficient to generate a humoral immune response, thereby making an anti-amylase antibody. The invention provides methods of making an anti-amylase immune comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having an amylase activity comprising the following steps: (a) providing a polypeptide of the invention; or a polypeptide encoded by a nucleic acid of the invention; (b) providing an amylase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having an amylase activity. In one aspect, the substrate can be a starch, e.g., a liquefied starch.

The invention provides methods for identifying an amylase substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an amylase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of an amylase activity comprising the following steps: (a) providing a polypeptide of the invention or a polypeptide encoded by a nucleic acid of the invention, including a nucleic acid having at least 90% or more sequence identity to SEQ ID NO:1, SEQ ID NO:3, or SEQ ID NO:9; (b) providing a test compound; (c) contacting the polypeptide of step (a) with the test compound of step (b) and measuring an activity of the amylase, wherein a change in the amylase activity measured in the presence of the test compound compared to the activity in the absence of the test compound provides a determination that the test compound modulates the amylase activity. In one aspect, the amylase activity can be measured by providing an amylase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of amylase activity. An increase in the amount of the substrate or a decrease in the amount of the reaction product with the test compound as compared to the amount of substrate or reaction product without the test compound identifies the test compound as an inhibitor of amylase activity.

The invention provides computer systems comprising a processor and a data storage device wherein said data storage device has stored thereon a polypeptide sequence or a nucleic acid sequence of the invention, or a polypeptide encoded by a nucleic acid of the invention. In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention; or a polypeptide encoded by a nucleic acid of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program.

The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having an amylase activity from an environmental sample comprising the steps of: (a) providing an amplification primer sequence pair for amplifying a nucleic acid encoding a polypeptide having an amylase activity, wherein the primer pair is capable of amplifying a nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, or a subsequence thereof; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having an amylase activity from an environmental sample. One or each member of the amplification primer sequence pair can comprise an oligonucleotide comprising at least about 10 to 50 consecutive bases of a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or a subsequence thereof.

The invention provides methods for isolating or recovering a nucleic acid encoding a polypeptide having an amylase activity from an environmental sample comprising the steps of: (a) providing a polynucleotide probe comprising a nucleic acid of the invention or a subsequence thereof, including a nucleic acid having at least 90% or more sequence identity to SEQ ID NO:1, SEQ ID NO:3, or SEQ ID NO:9; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having an amylase activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having an amylase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant amylase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until an amylase having an altered or different activity or an altered or different stability from that of a polypeptide encoded by the template nucleic acid is produced. In one aspect, the variant amylase polypeptide is thermotolerant, and retains some activity after being exposed to an elevated temperature. In another aspect, the variant amylase polypeptide has increased glycosylation as compared to the amylase encoded by a template nucleic acid. Alternatively, the variant amylase polypeptide has an amylase activity under a high temperature, wherein the amylase encoded by the template nucleic acid is not active under the high temperature. In one aspect, the method can be iteratively repeated until an amylase coding sequence having an altered codon usage from that of the template nucleic acid is produced. In another aspect, the method can be iteratively repeated until an amylase gene having higher or lower level of message expression or stability from that of the template nucleic acid is produced.

The invention provides methods for modifying codons in a nucleic acid encoding a polypeptide having an amylase activity to increase its expression in a host cell, the method comprising the following steps: (a) providing a nucleic acid of the invention encoding a polypeptide having an amylase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell. The invention provides methods for modifying codons in a nucleic acid of the invention encoding a polypeptide having an amylase activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding an amylase.

The invention provides methods for modifying codons in a nucleic acid encoding a polypeptide having an amylase activity to increase its expression in a host cell, the method comprising the following steps: (a) providing a nucleic acid of the invention encoding an amylase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having an amylase activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified amylase active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or a subsequence thereof, and the nucleic acid encodes an amylase active site or an amylase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified amylase active sites or substrate binding sites. In one aspect, the method comprises mutagenizing the first nucleic acid of step (a) by a method comprising an optimized directed evolution system, gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises an amylase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

The invention provides methods for modifying a small molecule comprising the following steps: (a) providing an amylase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the amylase enzyme, thereby modifying a small molecule by an amylase enzymatic reaction. In one aspect, the method can comprise a plurality of small molecule substrates for the enzyme of step (a), thereby generating a library of modified small molecules produced by at least one enzymatic reaction catalyzed by the amylase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule which exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an amylase enzyme comprising the steps of: (a) providing an amylase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for an amylase activity, thereby determining a functional fragment of an amylase enzyme. In one aspect, the amylase activity is measured by providing an amylase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods for hydrolyzing a starch comprising the following steps: (a) providing a polypeptide having an amylase activity, wherein the polypeptide comprises a polypeptide of the invention, or a polypeptide encoded by a nucleic acid of the invention, or a subsequence thereof; (b) providing a composition comprising a starch; and (c) contacting the polypeptide of step (a) with the composition of step (b) under conditions wherein the polypeptide hydrolyzes the starch. In one aspect, the composition comprising starch that comprises an α-1,4-glucosidic bond or an α-1,6-glucosidic bond.

The invention provides methods for liquefying or removing a starch from a composition comprising the following steps: (a) providing a polypeptide having an amylase activity, wherein the polypeptide comprises a polypeptide of the invention, or a polypeptide encoded by a nucleic acid of the invention; (b) providing a composition comprising a starch; and (c) contacting the polypeptide of step (a) with the composition of step (b) under conditions wherein the polypeptide removes or liquefies the starch.

The invention provides methods of increasing thermotolerance or thermostability of an amylase polypeptide, the method comprising glycosylating an amylase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the amylase polypeptide. In one aspect, the amylase specific activity can be thermostable or thermotolerant at a temperature in the range from greater than about 37° C. to about 95° C.

The invention provides methods for overexpressing a recombinant amylase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides detergent compositions comprising a polypeptide of the invention or a polypeptide encoded by a nucleic acid of the invention, wherein the polypeptide comprises an amylase activity. In one aspect, the amylase can be a nonsurface-active amylase. In another aspect, the amylase can be a surface-active amylase.

The invention provides methods for washing an object comprising the following steps: (a) providing a composition comprising a polypeptide having an amylase activity, wherein the polypeptide comprises: a polypeptide of the invention or a polypeptide encoded by a nucleic acid of the invention; (b) providing an object; and (c) contacting the polypeptide of step (a) and the object of step (b) under conditions wherein the composition can wash the object.

The invention provides methods for hydrolyzing starch, e.g., in a feed or a food prior to consumption by an animal, comprising the following steps: (a) obtaining a composition, e.g., a feed material, comprising a starch, wherein the polypeptide comprises: a polypeptide of the invention or a polypeptide encoded by a nucleic acid of the invention; and (b) adding the polypeptide of step (a) to the composition, e.g., the feed or food material, in an amount sufficient for a sufficient time period to cause hydrolysis of the starch, thereby hydrolyzing the starch. In one aspect, the food or feed comprises rice, corn, barley, wheat, legumes, or potato.

The invention provides methods for textile desizing comprising the following steps: (a) providing a polypeptide having an amylase activity, wherein the polypeptide comprises a polypeptide of the invention or a polypeptide encoded by a nucleic acid of the invention; (b) providing a fabric; and (c) contacting the polypeptide of step (a) and the fabric of step (b) under conditions wherein the amylase can desize the fabric.

The invention provides methods for deinking of paper or fibers comprising the following steps: (a) providing a polypeptide having an amylase activity, wherein the polypeptide comprises a polypeptide of the invention or a polypeptide encoded by a nucleic acid of the invention; (b) providing a composition comprising paper or fiber; and (c) contacting the polypeptide of step (a) and the composition of step (b) under conditions wherein the polypeptide can deink the paper or fiber.

The invention provides methods for treatment of lignocellulosic fibers comprising the following steps: (a) providing a polypeptide having an amylase activity, wherein the polypeptide comprises a polypeptide of the invention or a polypeptide encoded by a nucleic acid of the invention; (b) providing a lignocellulosic fiber; and (c) contacting the polypeptide of step (a) and the fiber of step (b) under conditions wherein the polypeptide can treat the fiber thereby improving the fiber properties.

The invention provides methods for producing a high-maltose or a high-glucose syrup comprising the following steps: (a) providing a polypeptide having an amylase activity, wherein the polypeptide comprises a polypeptide of the invention or a polypeptide encoded by a nucleic acid of the invention; (b) providing a composition comprising a starch; and (c) contacting the polypeptide of step (a) and the fabric of step (b) under conditions wherein the polypeptide of step (a) can liquefy the composition of step (b) thereby producing a soluble starch hydrolysate and saccharify the soluble starch hydrolysate thereby producing the syrup. In one aspect, the starch can be from rice, corn, barley, wheat, legumes, potato, or sweet potato.

The invention provides methods for improving the flow of the starch-containing production fluids comprising the following steps: (a) providing a polypeptide having an amylase activity, wherein the polypeptide comprises a polypeptide of the invention or a polypeptide encoded by a nucleic acid of the invention; (b) providing production fluid; and (c) contacting the polypeptide of step (a) and the production fluid of step (b) under conditions wherein the amylase can hydrolyze the starch in the production fluid thereby improving its flow by decreasing its density. In one aspect, the production fluid can be from a subterranean formation.

The invention provides anti-staling compositions comprising a polypeptide of the invention or a polypeptide encoded by a nucleic acid of the invention. The invention provides methods for preventing staling of the baked products comprising the following steps: (a) providing a polypeptide having an amylase activity, wherein the polypeptide comprises a polypeptide of the invention or a polypeptide encoded by a nucleic acid of the invention; (b) providing a composition containing starch used for baking; (c) combining the polypeptide of step (a) with the composition of the step (b) under conditions wherein the polypeptide can hydrolyze the starch in the composition used for baking thereby preventing staling of the baked product. In one aspect, the baked product can be bread.

The invention provides methods for using amylase in brewing or alcohol production comprising the following steps: (a) providing a polypeptide having an amylase activity, wherein the polypeptide comprises a polypeptide of the invention or a polypeptide encoded by a nucleic acid of the invention; (b) providing a composition containing starch and used for brewing or in alcohol production; (c) combining the polypeptide of step (a) with the composition of the step (b) under conditions wherein the polypeptide can hydrolyze the starch in the composition used for brewing or in alcohol production. In one aspect, the composition containing starch can be beer.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The following drawings are illustrative of embodiments of the invention and are not meant to limit the scope of the invention as encompassed by the claims.

Like reference symbols in the various drawings indicate like elements.

DETAILED DESCRIPTION

Figure 1:
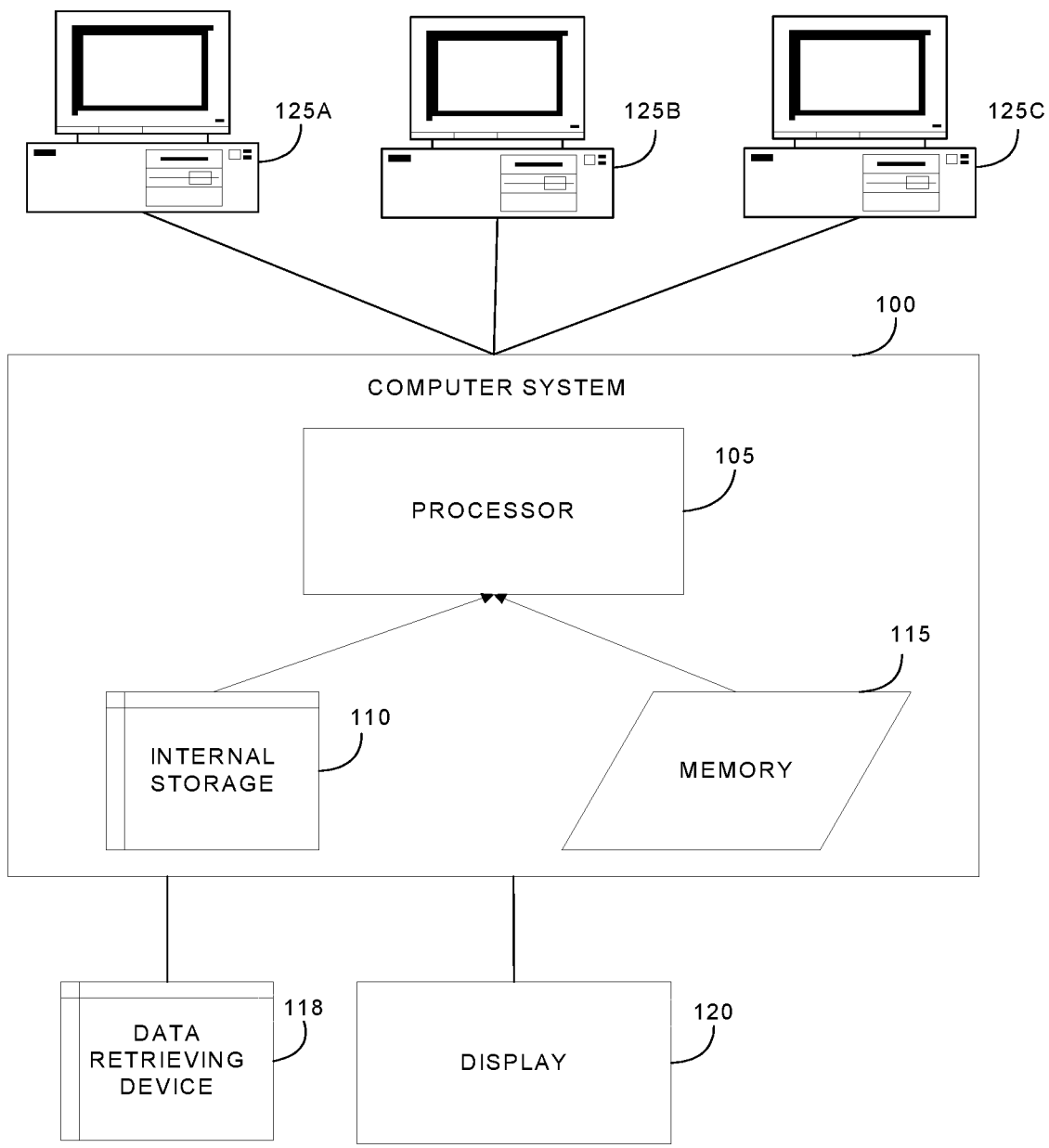
FIG. 1 is a block diagram of a computer system.

The invention provides amylase enzymes, polynucleotides encoding the enzymes, methods of making and using these polynucleotides and polypeptides. The invention is directed to novel polypeptides having an amylase activity, nucleic acids encoding them and antibodies that bind to them. The polypeptides of the invention can be used in a variety of diagnostic, therapeutic, and industrial contexts. The polypeptides of the invention can be used as, e.g., an additive for a detergent, for processing foods and for chemical synthesis utilizing a reverse reaction. Additionally, the polypeptides of the invention can be used in fabric treatment, alcohol production, and as additives to food or animal feed.

In one aspect, the amylases of the invention are active at a high and/or at a low temperature, or, over a wide range of temperature. For example, they can be active in the temperatures ranging between 20° C. to 90° C., between 30° C. to 80° C., or between 40° C. to 70° C. The invention also provides amylases that have activity at alkaline pHs or at acidic pHs, e.g., low water acidity. In alternative aspects, the amylases of the invention can have activity in acidic pHs as low as pH 5.0, pH 4.5, pH 4.0, and pH 3.5. In alternative aspects, the amylases of the invention can have activity in alkaline pHs as high as pH 9.5, pH 10, pH 10.5, and pH 11. In one aspect, the amylases of the invention are active in the temperature range of between about 40° C. to about 70° C. under conditions of low water activity (low water content).

The invention also provides methods for further modifying the exemplary amylases of the invention to generate proteins with desirable properties. For example, amylases generated by the methods of the invention can have altered enzymatic activity, thermal stability, pH/activity profile, pH/stability profile (such as increased stability at low, e.g. pH<6 or pH<5, or high, e.g. pH>9, pH values), stability towards oxidation, Ca' dependency, specific activity and the like. The invention provides for altering any property of interest. For instance, the alteration may result in a variant which, as compared to a parent enzyme, has altered enzymatic activity, or, pH or temperature activity profiles.

Definitions

The term "amylase" includes all polypeptides, e.g., enzymes or antibodies, that catalyze the hydrolysis of starches. For example, the term amylase, and the amylases of the invention, include polypeptides having glucoamylase activity, such as the ability to catalyze the hydrolysis of glucose polymers, e.g., glucose polymers linked by α-1,4- and/or α-1,6-glucosidic bonds. In one aspect, the polypeptides of the invention have glucoamylase activity, hydrolyzing internal α-1,4-glucosidic linkages to yield smaller molecular weight malto-dextrins. An amylase activity of the invention also includes α-amylase activity, including the ability to hydrolyze internal alpha-1,4-glucosidic linkages in starch to produce smaller molecular weight malto-dextrins. In one aspect, the α-amylase activity of the invention includes hydrolyzing internal alphα-1,4-glucosidic linkages in starch at random. An amylase activity of the invention also includes glucan 1,4-α-glucosidase activity, or, 1,4-α-D-glucan glucohydrolase, commonly called glucoamylase but also called amyloglucosidase and γ-amylase that, in one aspect, releases β-D-glucose from 1,4-α-, 1,6-α- and 1,3-α-linked glucans. An amylase activity of the invention also includes exo-amylase activity. An amylase activity of the invention also includes hydrolyzing starch at high temperatures, low temperatures, alkaline pHs and at acidic pHs.

An "amylase variant" comprises an amino acid sequence which is derived from the amino acid sequence of a "precursor amylase". The precursor amylase can include naturally-occurring amylases and recombinant amylases. The amino acid sequence of the amylase variant can be "derived" from the precursor amylase amino acid sequence by the substitution, deletion or insertion of one or more amino acids of the precursor amino acid sequence. Such modification can be of the "precursor DNA sequence" which encodes the amino acid sequence of the precursor amylase rather than manipulation of the precursor amylase enzyme per se. Suitable methods for manipulation of the precursor DNA sequence include methods disclosed herein, as well as methods known to those skilled in the art.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The term "expression cassette" as used herein refers to a nucleotide sequence which is capable of affecting expression of a structural gene (i.e., a protein coding sequence, such as an amylase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like.

"Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" includes nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 10%, 15%, 20%, 30%, 40%, 50%, 60%, 70%, 80%, 90%, 95%, 98% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence can be "operably linked to" a coding sequence when RNA polymerase which initiates transcription at the promoter will transcribe the coding sequence into mRNA, as discussed further, below.

"Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

The phrase "substantially identical" in the context of two nucleic acids or polypeptides, can refer to two or more sequences that have, e.g., at least about 50%, 55%, 60%, 65%, 70%, 75%, 80%, 85%, 90%, 95%, 98% or 99% or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, over a region of at least about 10, 20, 30, 40, 50, 100, 150, 200, 250, 300, 350, 400, 450, 500, 550, 600, 650, 700, 750, 800, 850, 900, 950, 1000 or more residues, or a region ranging from between about 50 residues to the full length of the nucleic acid or polypeptide. Nucleic acid sequences of the invention can be substantially identical over the entire length of a polypeptide coding region.

A "substantially identical" amino acid sequence also can include a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an amylase, resulting in modification of the structure of the polypeptide, without significantly altering its biological activity. For example, amino- or carboxyl-terminal amino acids that are not required for amylase activity can be removed.

"Hybridization" includes the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

"Variant" includes polynucleotides or polypeptides of the invention modified at one or more base pairs, codons, introns, exons, or amino acid residues (respectively) yet still retain the biological activity of an amylase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant amylase having activity at a pH or temperature, for example, that is different from a wild-type amylase, are included herein.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides nucleic acids, including expression cassettes such as expression vectors, encoding the polypeptides of the invention. The invention also includes methods for discovering new amylase sequences using the nucleic acids of the invention. The invention also includes methods for inhibiting the expression of amylase genes, transcripts and polypeptides using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lad, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express an amylase of the invention in a tissue-specific manner. The invention also provides plants or seeds that express an amylase of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) *Plant Mol. Biol.* 33:125-139); Cat3 from *Arabidopsis* (GenBank No. U43147, Zhong (1996) *Mol. Gen. Genet.* 251:196-203); the gene encoding stearoyl-acyl carrier protein desaturase from *Brassica napus* (Genbank No. X74782, Solocombe (1994) *Plant Physiol.* 104:1167-1176); GPc1 from maize (GenBank No. X15596; Martinez (1989) *J. Mol. Blot* 208:551-565); the Gpc2 from maize (GenBank No. U45855, Manjunath (1997) *Plant Mol. Biol.* 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of amylase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fbl2A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements El promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the amylase-producing nucleic acids of the invention will allow the grower to select plants with the optimal starch/sugar ratio. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

If proper polypeptide expression is desired, a polyadenylation region at the 3'-end of the coding region should be included. The polyadenylation region can be derived from the natural gene, from a variety of other plant genes, or from genes in the Agrobacterial T-DNA.

Expression Vectors and Cloning Vehicles

The invention provides expression vectors and cloning vehicles comprising nucleic acids of the invention, e.g., sequences encoding the amylases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements. In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173: 69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Host Cells and Transformed Cells

The invention also provides a transformed cell comprising a nucleic acid sequence of the invention, e.g., a sequence encoding an amylase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477, U.S. Pat. No. 5,750, 870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Amplification of Nucleic Acids

In practicing the invention, nucleic acids of the invention and nucleic acids encoding the polypeptides of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. In alternative aspects, where the primer pairs are capable of amplifying nucleic acid sequences including the exemplary SEQ ID NO:1, or a subsequence thereof; a sequence as set forth in SEQ ID NO:3, or a subsequence thereof; a sequence as set forth in SEQ ID NO:5, or a subsequence thereof; a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof. One of skill in the art can design amplification primer sequence pairs for any part of or the full length of these sequences; for example:

The exemplary SEQ ID NO:1 is

```
atgagagttt cctccatagg aaatggcaga atgctgataa actttgatga gaaaggaaga     60
atagtcgata tttattatcc ttatatagga atggagaacc agacttctgg aaacccaatt    120
aggttagcta tttgggacaa agataagaaa gtggcatctc tagatgagga ttgggaaact    180
actgtattat atatagatga agctaatatg gttgagatta ggagtgatgt taaggagtta    240
ggactttctc ttctctctta taactttcta gattctgatg atccgatata tatgtctatt    300
gtaaaaatag caaataacga aaataatagc agaaatataa aagtattttt tatacatgat    360
ataaatttat attcaaaccc ttttggggac actgcattct atgatcccct accccttca    420 attatacatt ataagtctaa acgatattta gcctttaaag tgtttaccac ggtatcgaca    480 cttctgagt ataacatagg caaaggtgac ttaattggag atatttatga tggcaattta    540
ggacttaatg gtatagaaaa tggtgatgta aattcaagta tgggtataga gataaatata    600
gatcctaatt cctatttgaa attatactac gtaatagtcg cagatagaaa cttggaaggc    660
ttaaggcaaa aaataaggaa aataaacttt gcaaacgtag agacatcgtt tacgttaacc    720
tatatgtttt ggcggaattg gttaaagaaa aataaactct tcagaaataa tttaatgcag    780
gatattaaga gagtctatga tgtgagtctt tttgtgataa gaaatcacat ggacgttaac    840
gggtcaataa tagcttcctc agacttctcc ttcgtcaaga tttatgggga ctcatatcag    900
tattgttggc ctagagatgc ggcaattgca gcttatgctc tagatctagc tggctataag    960
gaactagcat taaaacactt ccagttcatt tctaatattg caaattctga aggcttccta   1020
tatcataaat ataatccaaa tacaactcta gctagttctt ggcatccttg gtattataaa   1080
ggtaaaagga tatcccaat tcaaggggat gagacggcat tagaagtatg ggcaatagct   1140
agtcattacg aaaaatatga agatattgac gaaatacttc cattatataa gaagttcgtg   1200
aagccagcct taaaatttat gatgtctttt atggaagaag gattgccaaa accttctttt   1260
```

-continued

```
gacctatggg aagaaaggta tggtatacat atttacacag tatctacggt ttacggcgca  1320
ttaacaaagg gagcaaagtt agcttatgat gtaggtgatg aaatattaag tgaagattta  1380
agtgatacat cgggtttatt aaaaggaatg gttttgaaaa gaatgactta taatggaaga  1440
tttgttagaa gaatagacga ggaaaataac caagatctaa ctgtggactc aagtctctat  1500
gctccattct tctttggtct tgttaatgca aatgacaaaa tcatgataaa taccattaac  1560
gagattgaaa gcagattaac tgtgaatggc gggataataa ggtatgagaa tgatatgtat  1620
cagaggagga aaaacaacc aaacccttgg ataattacga cattatggct atctgaatat  1680
tatgcaacaa ttaacgataa aaataaggca aacgagtaca taaaatgggt aattaataggg  1740 gcattaccaa ccggcttttt accagaacaa gttgatccag aaactttga gccaacttca  1800 gttacacctt tggtatggtc tcatgctgaa ttcataatag caattaataa catt         1854
```

Thus, an exemplary amplification primer sequence pair is residues 1 to 21 of SEQ ID NO:1 (i.e., atgagagtttcctc-catagga) and the complementary strand of the last 21 residues of SEQ ID NO:1 (i.e., the complementary strand of ataatagcaattaataacatt).

The exemplary SEQ ID NO:3 is

```
atggttaggt atacaccgct tggcaatggg cggttgctta tagcttttga tactgattac    60
aggattgttg attttactat ttcaaagttt gcctccgaaa atcattcgtc tggtcatcca   120
ttctactttg gtgtttccgt ggatggcaat ttcaactgga tagacagaaa tgcaatcaag   180
cacatggact actacgacca caccatggtc tctgtcgtca actacacgca taacggtatt   240
gatttcgaga cagggatat ggttgacata tacaaggaca tctttattag gcgggtggtt   300
gctgaaaaca agaccggtaa ggatgtaaac ctgaagatct tctttcacca gaatttctac   360
atatatggca atgacatagg ggataccgct gcttactttc ctgaataccg cggtgtgatc   420
cattataagg gagggagata ctttctcgca tccactcttg atgagagcgg taatttctgc   480
gatcaatatg ccacaggggt taaggatgtg ggtgagctga agggcacatg gaaggatgcc   540
gaggacaatg aattatcaat gaacccggtg gcaataggtt cggtggattc tgtcataagg   600
cattccacga ctctgaaggc cggttcaaag ttcacgctct attatttcat catagcggga   660
agaaacatca acgatataga gagcgaatat tcaaatgtga atgtccagta cctccaaaag   720
cttctgagga gaacaacaaa ctactgggag ctctggtctt cgaaggtgac tcccagcctg   780
gattcagaca caacagcgct ttaccgcaga tcgctcttcg tgactaagag ccacgcaaac   840
gatcttgggg ccatagccgc atcctgcgac agcgatatac tgaagctgag ccatgacgga   900
tactactacg tctggcccag ggatgcctcc atggctgcat acgccttgag catatccggg   960
cacagcgaaa ccgccagacg cttctttgcc ctgatggaag attcactttc agaagaggga  1020
tacctgtacc acaaatacaa cgtcgacggc aagatcgcca gcagctggtt accgcacgtc  1080
atgaatggca atccatata tccaatacag gaggatgaaa cagctctggt ggtctgggca  1140
ctctgggaat actttaggaa gtacaatgat atcggcttca ccgcaccgta ttatgaacgc  1200
cttataacca gggcagcaga ctttatgacc aattttgttg acaacaacgg ccttcccaag  1260
ccatcctttg atctgtggga agagcgctat ggaatccatg cctacactgt tgctacggtt  1320
tatgccgccc tgaaagcagc ttcaaacttt gcaaacgttt tcggcgatcc tgatctatcg  1380
gaaaaatacg aaaatgctgc ggaaaggat taccatgcgt tcgatgaaag gttctattct  1440
gaggatacgg gatactatgc aagggccatc atagacggaa agccggactt caccgtggac  1500
```

```
agcgccctca cctcactggt gctctttgga atgaaggatg cggacgatcc aaaggttatt   1560
tctaccatgc agaggatatc tgaagaccta tgggtgaatg gcgttggagg catagcgcgc   1620
taccagaacg acagatacat gagggtgaag gacgatccaa gcgttcctgg aaatccctgg   1680
ataataacca cgctgtggat ggcaagatac tatatgcgtt ttggtgattt tgaaaaggcc   1740   1572
```

Thus, an exemplary amplification primer sequence pair is residues 1 to 21 of SEQ ID NO:3 (i.e., atggttaggt atacac-cgctt) and the complementary strand of the last 21 residues of SEQ ID NO:3 (i.e., the complementary strand of tttggt-gattttgaaaaggcc).

The exemplary SEQ ID NO:5 is

```
atgatttata tgggcggaat aattggaaat aacaacctat tagtaaaaat cggagattat     60
ggggaaatta gttatgtttt ctatcctcat gtgggttatg aaacccattt cttcgattct    120
gcattggcag tgtatgataa aaaagtaaaa tggcattggg atgatgattg ggacatctct    180 caaaatata ttgaagaaac aaatatattc aaaactatac tggaagacga taaaataata    240
ttgacaatta aagattttgt tccagtttcg cacaatgtaa tcattagaag gttgcatata    300
aaaaataaac tcgataaaaa attgaatttt aagctatttt tttatgaaaa tttaaggatt    360
ggggagtatc ctacagaaaa tgccgtaaga ttttagagg atgagggatg tatcgttaaa    420
tataacgaaa aatatgtttt ctgcattgga agtaataaaa agatagattc gttccagtgt    480
ggaaacagat acagcaaaaa cagtgcatac gtagatattg aaaacggatt gttgatggaa    540
cataaagaaa gccatggact gatgacagat agtgcaatat cgtggaatat agagattgat    600
aaaggaaaga gcttagcgtt taatatctat atacttctac aaaaatttga tggagattta    660
tcaataataa ccgagcagtt aaagattata atgaacaata ctgtacatat caaagacctt    720
tcaatgaact attggaaaaa tagcattgga aatataaaag aacatatcca tcctcaattt    780
cattcagata aagaaatatg tcctatagct aaaagggctt taatggttct tctaatgctt    840
tgtgataaag atgggggggat tatagccgct ccttcactac atccagacta taggtatgtt    900
tggggagggg atgggctta tatagcaatt gcattagatt tatttggaat tagaggaatt    960
cccgatagat tctttgaatt catgtctaaa attcaaaatg atgatggttc atggctacaa   1020
aactactaca caaatggaaa accgagatta acagcgatgc agattgacca aattggctct   1080
atactgtggg ctatggatgt gcattataga ttaactggaa atagaaagtt tgttgagagg   1140
tattggaata ctatagaaaa agctggaaat tatctaactt ctgccgcttt aaacttcaca   1200
ccatgctttg atttatggga agaaaagttt ggagtttttg catatactat gggagcaatc   1260
tatgcgggat taaagctgc ttatagtatg agtaaagctg ttgatatgag ggataaggtt   1320
aaacattggg aaaaagctat tgaattttg aaaaaggaag ttccaaggag attttattta   1380
gaagatgagg aaagatttgc taaatcaata aatccattgg ataaggagat agacgctagc   1440
atattgggat tgagctatcc atttaactta attgatgttg atgatgaaag gatgataaaa   1500
acagctgagg ctattgaaaa tgcatttaac tacaaagttg gtgggattgg gagatatcct   1560
aatgatgttt attttggagg gaacccatgg attataacga cattgtggat ttctttatat   1620
tatagaaggt tatccaaggt tttaaaagag aaaaataaaa atgatatggc agagaaatat   1680
ttaaaaaaat ctaaaaaatt gtttgattgg gcagttaaat acagctttaa cggtttgttt   1740
ccagagcaga tacataagga cctcggcatt ccaatgtctg caatgccttt gggctggagc   1800
aatgcaatgt tttaatcta cctatataag gatgacaatg tcataattcc ataa          1854
```

Thus, an exemplary amplification primer sequence pair is residues 1 to 21 of SEQ ID NO:5 (i.e., atgatttatatgggcggaata) and the complementary strand of the last 21 residues of SEQ ID NO:5 (i.e., the complementary strand of gacaatgtcataat-tccataa).

The exemplary SEQ ID NO:7 is

```
atggcaggga ttattggaaa tggaaaccta ctggcaaaaa ttgatgactt ggggtctata    60
gaatatatat ttttcccaca tttgggttac gaaacacata ttctcgatac atcatttgct   120
atatactaca acaacaaaat aaaatggcat tgggatcata gttgggacgt tagtcagaac   180
tatctcaaag attccaacat attaaaaaca acttatgaaa atgatgactt cttaatatat   240
tctaaggatt gtgtatccat atctcacaac cttattgtta acaactttc tataataaac     300 aagaccaatt cagaaaagga cataaaatta ttttttttatg aaaatttgag aataggtgaa   360
acgccgagta aaagcactgt aaaatttgtt aagaaaaaa actgcctaat taaacatgac    420
aaaaattata ttttctgtat tggcagtaat aaaaaagtat cctcttacca atgtgggatt   480
aaatactctg agagtagtgc tttaagggac attgaaaatg gagtactgaa agagcagagt   540
tccgccacag gattaatcac agacagtgcc ctttgctggg aattcaaaat caaacctaac   600
caaaaataca ctctttcaat actcatactt cctgaaaagt atgatggtga ttataataaa   660
accctaaact aatggatac tctacacatg gtaaaagaca acctcaaaga cctatataac    720\ ctcacaagaa atttctggaa aagtagagta gatagcatgg taaataagtg gggaatctta   780
aagttggaag aatataaaga atgcatagat atatgcaaaa gatctctact aaccctatta   840
cttctctgcg attataaggg gggaataatt gcttctcctt ctttacatcc agattatagg   900
tatgtctggt gtagggatgc agggtatatg gcagttgcgt tggatttgtg tgggcagcat   960
gaaatgagtg agaaatactt tgagtggtgc aagacaacac aaaacagtga cggttcttgg  1020
gttcaaaatt actatgtgga ggggtatcca agattcacag ccatccaaat agatcaggtg  1080
ggtactacca tttgggcact tcttgtgcac tatagaataa ctggagacaa acatttttta  1140 aaagaaatt gggaaatggt caaaaaagca ggggactatt tgagcagagc tgctgaccaa   1200 ttaatacccct gctatgactt atgggaagaa aagtttgggg tctttgcata taccctcgga  1260
gcaatatatg ggggttgaa atcaggttat ttaattggaa aagaacttga caagaagaa    1320 gaaatacagc attggaaaaa aagcatgaac ttccttaaaa atgaagtggt aaatagactc  1380
tacttaaaaa atgagaagag gtttgcaaaa tcattaaaac cattagataa aaccatagat  1440
acgagtattt tagggttaag tttcccctat ggacttgtgt cagtcgatga cccaagaata  1500
atatcaactg caaatcagat tgaaaaagcc ttcaactaca agttggtgg tgttggtaga   1560 tatccagagg acatatactt tggaggaaat ccttggataa taacaaccct atggctctat  1620
atgtattata aaaagttagt tgatacatta tcaaaaaaag gaaaattcca agagtccata  1680
attgataatt acaataaaaa atgttacaac ttgcttaaat ggattctaaa acatcaattc  1740
aatggtatgt ttccagaaca agtccataaa gatttgggaa ttccaatatc tgcaattccc  1800
cttggctggt cacatgccat ggttataatc gctattcatg gtgattacga catcctaata  1860
ccctaa                                                             1866
```

Thus, an exemplary amplification primer sequence pair is residues 1 to 21 of SEQ ID NO:7 (i.e., atggcagggattattggaaat) and the complementary strand of the last 21 residues of SEQ ID NO:7 (i.e., the complementary strand of a tacgacatcctaataccctaa).

The exemplary SEQ ID NO:9 is

```
atgatttata tgggtggaat cgttggaaac aatagtttat tagccaaaat tggagattat    60
ggggaaattg aatacctttt ttatccccaa gttggttatg aaactcattt ctttgactct   120
gcattggcag tttatgataa aaaagtaaag tggcattggg atgatgattg ggatataacc   180
caaaaataca ttgaggaaac gaacatattt aaaactatct tagaagatga taagattata   240
ttaaccatta aagattttgt gccagtatct cacaacgtgc ttataagaag agtgtatata   300
aaaaataaac tcgataaaaa attaaatttt aagctctttt tttacgaaaa tttgagaatt   360
ggtgaaaacc caataacaaa tacagttaaa ttcttagaag atggttgtat cgttaaatat   420
aatggaaaat atattttttg cattggaagt gataaaagaa tagattcatt tcagtgtgga   480
aatagataca gtaaaacaag tgcttacata gacatagaaa atgggatatt gaaggagcat   540
aaagagagtt ctggattatt aaccgatagt gcaatatcat ggaatataaa gattgatgaa   600 aaagaagtt tggcattcaa catctacata cttccacaaa gattcgatgg agattttca   660 ataataactg aacaactaaa gattataatg aataacagtg aaaacattaa aaatctctca   720
atgaattatt ggaaacatat tataggggag ataaatagat ttatacatcc tgagcttagg   780
caaaataata agatttattc tataactaaa agggctttaa tgacactttt aatgttatgt   840
gataaggaag gagggattat agcggctcca tctctacatc cagattatag atacgtgtgg   900
ggaagagatg gaagttatat ctcaattgct ttggacttat ttggcataag gaacattcca   960
gacagatttt ttgaattcat gtctaagata caaaatgcag acggttcatg gctacaaaat  1020
tattatgtta atggaaaacc acgattaact gcaatacaga ctgaccaaat tggttccata  1080
ttatgggcaa tggatgtgca ttacagatta actggggata gaaagttcgt tgagagatac  1140
tggaacacta tagagaaagc tgctaattat ttaaggttgg tagctttaaa ctttactcca  1200
tgcttcgatt tgtgggaaga gaggtttgga gtatttgctt atacaatggg agctacttac  1260
gctggattga aatgtgcata cagcatgagt aaggcagtga ataaaaggga taaagttaag  1320
gattggggaa aaaccataga attttaaaa catgaggttc caaagagatt ttatttggaa  1380
gatgaggaaa gatttgctaa atcaataaat cctttagaca agacgataga cacaagcata  1440
ttgggtttaa gttaccctttt caatttgatt gatgttgatg atgagagaat gataaaaaca  1500
gccgaagcaa ttgaaaaagc tttcaaatat aaggttggag ggattgggag atatccagaa  1560
gacatttact ttggaggcaa tccatggatt ataaccacat tatggctttc tttgtattat  1620
agaaggttat acaaggtttt aaaagaaaaa gatgataatg gggcagatat ttatctacaa  1680
aaatctaaga agttgtttaa ttgggtgatg aaatacagct tgatgggct gtttccagag  1740 caaattcata aagaattagg tgtgccaatg tccgctatgc ctttaggctg gagcaatgca  1800
atgttcctca tttatgtgta tgagaatgat aaggtcataa taccataa                1848
```

Thus, an exemplary amplification primer sequence pair is residues 1 to 21 of SEQ ID NO:9 (i.e., atgatttatatgggtggaatc) and the complementary strand of the last 21 residues of SEQ ID NO:9 (i.e., the complementary strand of gataaggt-cataataccataa).

The exemplary SEQ ID NO:11 is

```
gtggttagca tggtaggaat tattgggaat gggaaaatcc tcgcaaagat tgatgactca    60
ggctctttgg aatacatatt ttttccacat ttggggcatg agaaacatat ttttgattca   120
tcatttgcca tattttatga taataagttg aaatggaatt gggacaattc ctgggatatt   180
aatcagaact atttaaaaga tacaaacata ttgaaaacat catatgaaaa cgaggatttt   240
ctaatagaat caaaggacta cgtgcctata tcccataact cgataattaa gcaaatatca   300
atattaaaca aatccagcga aaaaagaat ttaaaactgt ttttttatga aaatttaaga   360
atgggagaaa ttcctgaagt aagtactgta aagtatagaa agaacaggga gtgcattatt   420
aaatacgata agaattatgt tttttgtatc ggcagtaata aaaaagtatc ttcataccaa   480
tgtggtgtta ggtcatccga gagtagtgcc ctaaatgatc tcaaaaatgg tattttaaag   540
gaatacgata gtgctgaagg cctaatcaca gatagcgcac tgggttggga ccttgagttg   600
agtccaaatc aggaacagaa agtctcaata tttatatttg cagataagta tggtggggat   660
tataccaaaa ttatgaattt attggataca ctaaatatag ttataaccaa tcacgcagac   720
atatatgatc ttacaatggc atactggaag aacatgattg aaaccactgc gaatagtcta   780
tgcaattcaa atcaagtctt taaagattta acacatataa aagacgacgc aaatatttca   840
aatttaaaaa gaataaaaca gtatgaagct atttgtaaaa gatccctatt aaccatttta   900
ctcctttgtg atcataatgg tggaataatt gcatcaccat cactctatcc agattataga   960
tatgtatggt gtagggacgc aggttatatg gccgtcgcac ttgacctatg tggtcagcat  1020
ggaataagcg aaaaatactt tgaatggtgc aaaaaaacac aaaatagtga tggctcatgg  1080
gttcaaaact actacgtaga aggaaatcca aggcttacgg caattcaaat tgaccaagtt  1140
ggtactacaa tctgggccgc acttgtacat tatagaataa ctaggacaa attatttctg  1200
aacagatatt gggaaatgat taaaaaagca ggggattatt taagtagtgt tgccaatcca  1260
ccatcaccaa gctatgattt atgggaagaa aaatatggtg tattcgcata cacacttggc  1320
gcaatttatg gaggattaaa atctgcctac aacatttgta aaatactggg caaggaagaa  1380
cacgatatcc aaaattggaa agagagcatg gacttcctta aaaacgaaat ggtagatagg  1440
ctttatttaa aagatgaaaa tagatttgca aaatcattgg atccattgga caaagctcta  1500
gatgctagta ttttagggct cagttttcca tataatttgg tacctgttga tgaccctaga  1560
atgattagca ccgccaacca aattgaaaat gcgtttaagt ataaggttgg aggtatagga  1620
aggtaccctg aagatgttta tttcggaggg aatccttgga taataaccac aatatggctc  1680
catatgtact atgaaaactt gattaaatca ttatctaaac atggtaaaaa tgccatacat  1740
tctgatcaaa tccctgattc ttcaggggac cttaaggatt ttgtctcaat tatagggtcc  1800
attgaaaacc atggtgaaaa gtcagatgaa acccctagtt ccgacacact ccttacttat  1860
gcccaaaaat gtaacaattt gtttgattgg actttaaagt ataactttaa tgaactattt  1920
ccagaacagg ttcacaaaga tcttggagct ccgatatctg caattccact tgggtggtca  1980
catgcaatgg tcataattgc catccatggt aactttgata tattaatacc ttaa         2034
```

Thus, an exemplary amplification primer sequence pair is residues 1 to 21 of SEQ ID NO:11 (i.e., gtggttagcatggtaggaatt) and the complementary strand of the last 21 residues of SEQ ID NO:11 (i.e., the complementary strand of tttgatatattaataccttaa).

The exemplary SEQ ID NO:13 is

```
atgattgttg gtaataatag ctttttatgt aagataggggg atcatggaga aattgaatat    60
gcattctacc cccatgttgg ttatgaacta cattttttg atagttcttt agctatatat    120
gataaagaaa ttatgtggat atgggataaa gagtggagtg tatatcagaa atatattgag    180
gacactaata tattcaaaac tactttagaa aatgagaata tcatatttgt tataaaagat    240
ttagtcccaa tttcacataa tgtattaatt aggagagttt tcattaaaaa taaacttcca    300
tataattata attttaaact attttctat gaaaatctta gaattggaga acatccttca    360
gaaaatacag ttaagttttt agatgattgt atagttaaat ttaatggcaa atatacttt    420
tgtataagca gtgataaaaa aataaattca tatcagtgtg gaaatagata tagtgaaaaa    480
tctgcttata aagatattga aaatggttta ttatctgaaa atcctgaaag tgttggagtt    540
ctaactgaca gtgctattga atgggatata gatttaaaac cacatggaaa agtagcatt    600
aacatctaca tctttcctca tattggaaat aatatagaga ttataaaaaa tcagttaaat    660
attattaaaa atctctcttc tgaaataaaa aatatatctc taaattattg gaagagttct    720
tttgatataa aaggttatct atttaatgaa aaatatttaa aattagcaaa aagggcttta    780
atgatactaa caatgctttc tgacaaaaat ggaggaatta tagcctctcc atctattcat    840
cctgattata gatatgtttg gggtagagat ggaagttata tggctgtggc attatccatt    900
tatggaataa aaaacattcc atggaggttc ttccatttca tgtctaaagt ccagaatctt    960
gatggttcat ggttacaaaa ctattataca gatggtaaac caagattaac tgctttacaa   1020
atagatcaaa taggttcagt tctttgggct atggaagttt attatagaac tacaggtgat   1080
agagagtttg ttaaaaaatt ctgggaaact attgagaaag ctggaaattt cttatataat   1140
gcttcattat ctttaatgcc atgttttgat ctttgggaag aaaaatatgg ggtattttca   1200
tatactttag gagcaatgta tggaggatta agggcaggat gtagtttagc taaagctata   1260
gaagagaaaa aagaagattg gaaaaaggct ttagataaat taaagaagga tgttgattta   1320
ttatattaa gtgatgaaga aagatttgtt aaatctatta acccattgaa caaagagatt   1380
gatacaagta tattagggct tagctatcca tttggactag ttaaagttaa tgatgaaaga   1440
atgataaaaa ctgctgaagc catagaaaaa gcttttaaat acaaagttgg aggtattggg   1500
agatatccat ctgatgttta ttttggagga atccttgga ttataacaac actttggtta   1560
gctttatatt atagaagact atttattact acaaatgata gaaatatttt agaaaaatca   1620
aaaaagctat ttaattgggt tattaaccat atctatctat tccctgaaca gatacataaa   1680
gaattagcta ttcctgtatc agctatgcct ttaggttgga gttgtgctat gctgttattc   1740
tatctatata aaaatgatga cataatagtg ataaaatga                          1779
```

Thus, an exemplary amplification primer sequence pair is residues 1 to 21 of SEQ ID NO:13 (i.e., atgattgttggtaataatagc) and the complementary strand of the last 21 residues of SEQ ID NO:13 (i.e., the complementary strand of gacataatagtgataaaatga). The exemplary SEQ ID NO:15 is

```
atgaaattga atagaaaact tataaaatat ttacccgtac tatttcttgc gtccagtgtg    60
ctaagtggat gcgctaacaa taatatatca aacattaaaa ttgagagatt gaataatgta   120
```

```
caagcagtaa atggccctgg agaggctgat acttgggcta aagctcagaa acaaggtgta    180
gggactgcaa acaactatac ttccaaagta tggtttacca ttgcagacgg ggggatatct    240
gaggtttact atccgactat agatactgct gatgtaaagg atattaaatt ttttgtgaca    300
gatggaaaaa cgtttgtctc agatgagaca aaagacacaa taaccaaagt cgaaaagttt    360
actgaaaaat cgttggggta taaaatcatt aacacagata agaagggag atataagata    420 actaaagaaa tatttacgga tgtaaagagg aattctctcg taattaaaac gaagtttgaa    480
gccttaaaag gcaatgttga tgattacagg ctttacgtaa tgtgtgatcc tcatgtaaaa    540
aatcagggca aatataatga aggatatgca gttaaggcaa atggcaatgt tgcgctaatt    600
gctgaaagag atggaattta cactgcattg tcatctgaca taggatggaa aaagtattcg    660 ataggtatt ataaagtaaa tgacattgag accgatcttt ataaaaatat gcaaatgact    720
tacaattacg acagtgcaag aggcaacatc atagaaggtg ctgagataga tcttaagaaa    780
aacaggcaat ttgaaatcgt tctgtctttc ggacagagtg aagacgaggc agtaaaaaca    840
aacatggaaa ctttaaatga taattatgac agcttaaaga aagcgtatat agaccaatgg    900
gagaagtatt gcgatagcct taatgacttt ggaggaaaag caaattcact gtattttaac    960
agtatgatga tattaaaggc cagtgaagac aagacaaaca aaggtgctta tatagcatcg   1020
ctatctattc cgtggggtga tggccaagaa gatgacaata ttggtggcta ccatctcgta   1080
tggtcaagag atctgtacca tgtagcgaat gcatttattg ttgctggtga tactgattcg   1140
gcaaatagag cactggatta tttagacaaa gtagtgaaag acaatggaat gattcctcaa   1200
aatacatgga taaatggaag gccttattgg acaggcatac agcttgatga gcaggcggat   1260
ccaataatat taagctatag gttgaaaaga tacgatctct atgaaagtct tgttaagcct   1320
ttggcggatt tcatcatgaa aataggccct aagacgggac aagaaagatg ggaagaaata   1380
ggtggatatt cgccagcaac attggcttca gaagtagctg gacttacatg tgctgcgtat   1440
atagctgaac aaaataagga ctttgaatct gctaaaaaat atcaagaaaa ggcggataat   1500
tggcaaaggc ttattgacaa cctaacttac acagaaaaag gcccattggg agatggtcac   1560
tattatataa ggatagcagg gcttccagat ccaaatgccg atttcatgat aagcatagcg   1620
aatggcggtg gtgtatacga ccaaaaagaa atcgtggatc caagttttct ggaacttgta   1680
aggcttggag taaaatcagc agatgaccct aaaatactaa atacgctgaa agtcgtggat   1740
gaaacaataa aagtcgatac accgaaagga ccatcatggt ataggtataa tcatgatgga   1800
tatggtgaga tgtctaagac agaactatat catgggacag gaaaaggaag attgtggcca   1860
ctgcttacag gtgagagagg catgtacgaa attgctgcag agtatgatga tgtaataatt   1920
ataaagacaa gaataggttt attgaaaggc tcaaggataa gatttgagta cgatatagtg   1980
aaagaagatg aaaataagct tttagcacaa ggtatgacag aacacccatt tacgacactt   2040
gacagaaaac ctgtaaatat aaaaaagatt ttgcctcatg tttatgaaat gttgaacaaa   2100
tgctatgatg atggtgttta g                                             2121
```

Thus, an exemplary amplification primer sequence pair is residues 1 to 21 of SEQ ID NO:15 (i.e., atgaaattgaata-gaaaactt) and the complementary strand of the last 21 residues of SEQ ID NO:15 (i.e., the complementary strand of tgctatgatgatggtgtttag).

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample.

In one aspect of the invention, message isolated from a cell or a cDNA library are amplified.

The skilled artisan can select and design suitable oligo-nucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids having at least 90% sequence identity to SEQ ID NO:5, nucleic acids having at least 60% sequence identity to SEQ ID NO:7, nucleic acids having at least 50% sequence identity to SEQ ID NO:11, nucleic acids having at least 70% sequence identity to SEQ ID NO:13, nucleic acids having at least 80% sequence identity to SEQ ID NO:15. In one aspect, the invention provides nucleic acids and polypeptides having at least 99%, 98%, 97%, 96%, 95%, 90%, 85%, 80%, 75%, 70%, 65%, 60%, 55% or 50% sequence identity (homology) to SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, or SEQ ID NO:16. In one aspect, the invention provides nucleic acids and polypeptide having sequence as set forth in SEQ ID NO:1, SEQ ID NO:2, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, or SEQ ID NO:16. In alternative aspects, the sequence identity can be over a region of at least about 5, 10, 20, 30, 40, 50, 100, 150, 200, 250, 300, 350, 400, 450, 500, 550, 600, 650, 700, 750, 800, 850, 900, 950, 1000, or more consecutive residues, or the full length of the nucleic acid or polypeptide. The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (a sequence of the invention, e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, e.g., 50%, 55%, 60%, 65%, 70%, 75%, 80%, 90% or 95% sequence identity to a sequence of the invention (including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16), that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., M. genitalium (Fraser et al., 1995), M. jannaschii (Bult et al., 1996), H. influenzae (Fleischmann et al., 1995), E. coli (Blattner et al., 1997), and yeast (S. cerevisiae) (Mewes et al., 1997), and D. melanogaster (Adams et al., 2000). Significant progress has also been made in sequencing the genomes of model organism, such as mouse, C. elegans, and Arabadopsis sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "−F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs: Existence:11
Extension:1"

Other default settings can be: filter for low complexity OFF, word size of 3 for protein, BLOSUM62 matrix, gap existence penalty of −11 and a gap extension penalty of −1. An exemplary NCBI BLAST 2.2.2 program setting has the "−W" option default to 0. This means that, if not set, the word size defaults to 3 for proteins and 11 for nucleotides.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence (s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 2:
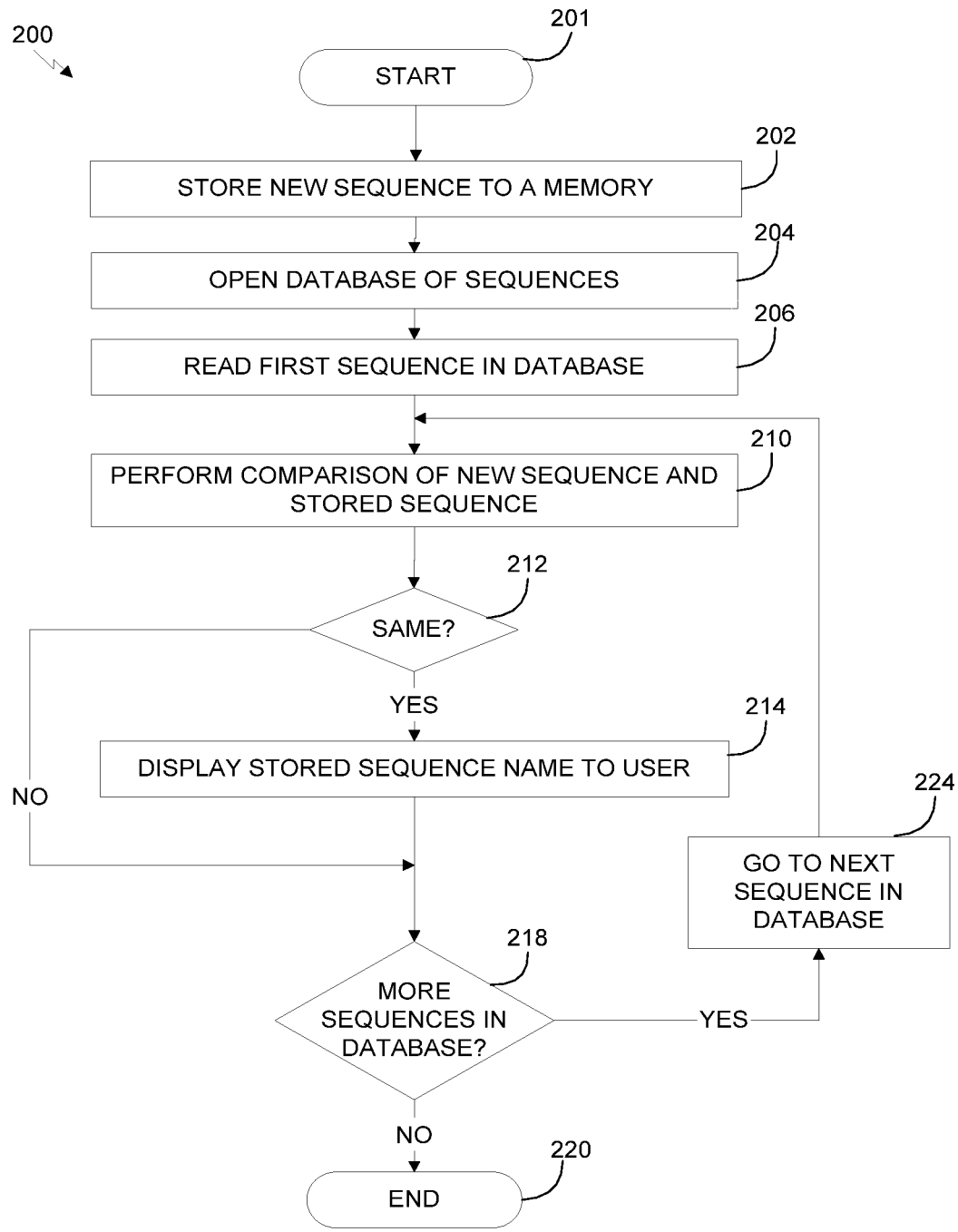
FIG. 2 is a flow diagram illustrating one aspect of a process for comparing a new nucleotide or protein sequence with a database of sequences in order to determine the homology levels between the new sequence and the sequences in the database.
Figure 3:
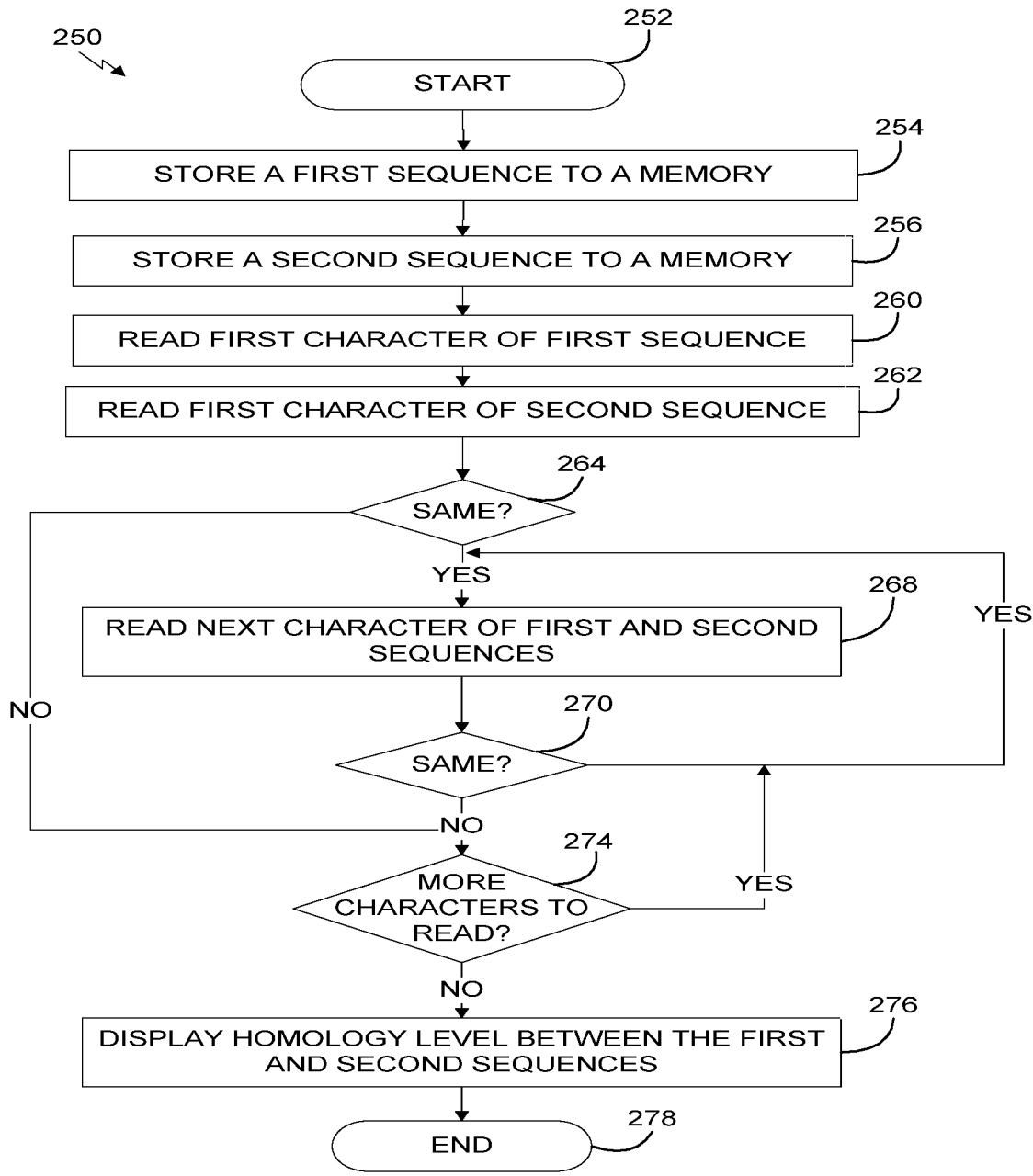
FIG. 3 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GEN-BANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
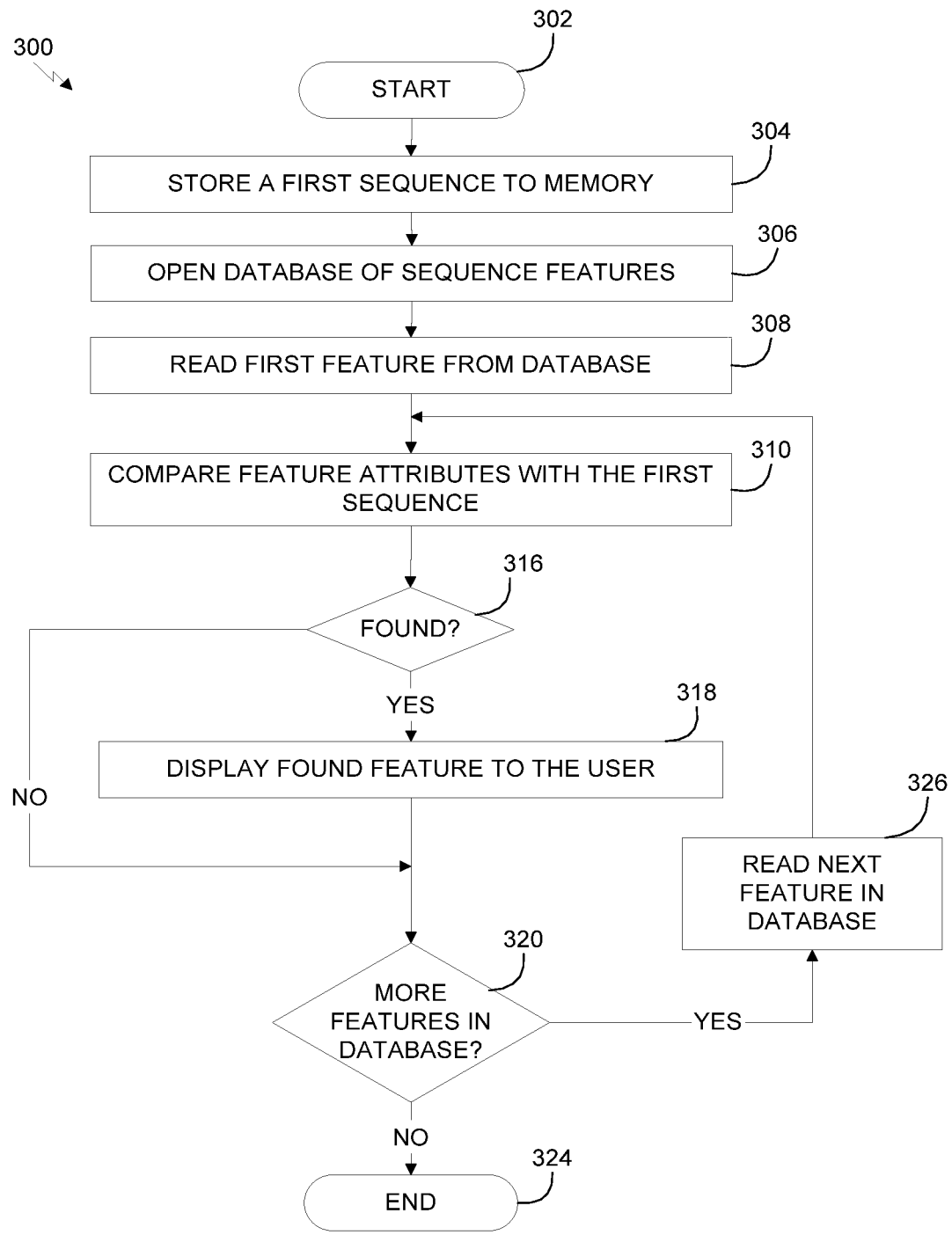
FIG. 4 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention can be stored and manipulated in a variety of data processor programs in a variety of formats. For example, a sequence can be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/

SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, or a nucleic acid that encodes a polypeptide of the invention. The stringent conditions can be highly stringent conditions, medium stringent conditions, low stringent conditions, including the high and reduced stringency conditions described herein. In one aspect, it is the stringency of the wash conditions that set forth the conditions which determine whether a nucleic acid is within the scope of the invention, as discussed below.

In alternative embodiments, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68°

C. for 15 minutes; or, equivalent conditions. See Sambrook, Tijssen and Ausubel for a description of SSC buffer and equivalent conditions.

These methods may be used to isolate nucleic acids of the invention.

Oligonucleotides Probes and Methods for Using them

The invention also provides nucleic acid probes that can be used, e.g., for identifying nucleic acids encoding a polypeptide with an amylase activity or fragments thereof or for identifying amylase genes. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency can vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization can be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2\times10^7$ cpm (specific activity $4-9\times10^8$ cpm/ug) of $^{32}P$ end-labeled oligonucleotide probe can then added to the solution. After 12-16 hours of incubation, the membrane is washed for 30 minutes at room temperature (RT) in 1×SET (150 mM NaCl, 20 mM Tris hydrochloride, pH 7.8, 1 mM $Na_2EDTA$) containing 0.5% SDS, followed by a 30 minute wash in fresh 1×SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+

0.41(fraction G+C)−(600/N) where N is the length of the probe. If the hybridization is carried out in a solution containing formamide, the melting temperature may be calculated using the equation: Tm=81.5+16.6(log [Na+])+ 0.41(fraction G+C)−(0.63% formamide)−(600/N) where N is the length of the probe. Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention can be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids, as determined using a sequence alignment algorithm (e.g., such as the FASTA version 3.0t78 algorithm with the default parameters, or a BLAST 2.2.2 program with exemplary settings as set forth herein).

Inhibiting Expression of Amylase

The invention provides nucleic acids complementary to (e.g., antisense sequences to) the nucleic acid sequences of the invention. Antisense sequences are capable of inhibiting the transport, splicing or transcription of amylase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind amylase gene or message, in either case preventing or inhibiting the production or function of amylase. The association can be through sequence specific hybridization. Another useful class of inhibitors includes oligonucleotides which cause inactivation or cleavage of amylase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of protease expression on a nucleic acid and/or protein level, e.g., antisense, iRNA and ribozymes comprising protease sequences of the invention and the anti-protease antibodies of the invention.

Inhibition of amylase expression can have a variety of industrial applications. For example, inhibition of amylase expression can slow or prevent spoilage. Spoilage can occur when polysaccharides, e.g., structural polysaccharides, are enzymatically degraded. This can lead to the deterioration, or rot, of fruits and vegetables. In one aspect, use of compositions of the invention that inhibit the expression and/or activity of amylases, e.g., antibodies, antisense oligonucleotides, ribozymes and RNAi, are used to slow or prevent spoilage. Thus, in one aspect, the invention provides methods and compositions comprising application onto a plant or plant product (e.g., a fruit, seed, root, leaf, etc.) antibodies, antisense oligonucleotides, ribozymes and RNAi of the invention to slow or prevent spoilage. These compositions also can be expressed by the plant (e.g., a transgenic plant) or another organism (e.g., a bacterium or other microorganism transformed with an amylase gene of the invention).

The compositions of the invention for the inhibition of amylase expression (e.g., antisense, iRNA, ribozymes, antibodies) can be used as pharmaceutical compositions, e.g., as anti-pathogen agents or in other therapies, e.g., anti-inflammatory or skin or digestive aid treatments.

Antisense Oligonucleotides

The invention provides antisense oligonucleotides capable of binding amylase message which can inhibit proteolytic activity by targeting mRNA. Strategies for designing antisense oligonucleotides are well described in the scientific and patent literature, and the skilled artisan can design such amylase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense amylase sequences of the invention (see, e.g., Gold (1995) J. of Biol. Chem. 270:13581-13584).

Inhibitory Ribozymes

The invention provides ribozymes capable of binding amylase message. These ribozymes can inhibit amylase activity by, e.g., targeting mRNA. Strategies for designing ribozymes and selecting the amylase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA interference (RNAi)

In one aspect, the invention provides an RNA inhibitory molecule, a so-called "RNAi" molecule, comprising an amylase sequence of the invention. The RNAi molecule comprises a double-stranded RNA (dsRNA) molecule. The RNAi can inhibit expression of an amylase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding am amylase. These methods can be repeated or used in various combinations to generate amylases having an altered or different activity or an altered or different stability from that of an amylase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dime'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154: 350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410. Non-stochastic, or "directed evolution," methods include, e.g., saturation mutagenesis (GSSM), synthetic ligation reassembly (SLR), or a combination thereof are used to modify the nucleic acids of the invention to generate amylases with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation mutagenesis, or, GSSM

In one aspect, codon primers containing a degenerate N,N,G/T sequence are used to introduce point mutations into a polynucleotide, e.g., an amylase or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence (s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., amylases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate polypeptides, e.g., amylases or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over 10100 different chimeras. SLR can be used to generate libraries comprised of over 101000 different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences.

Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing. Optimized Directed Evolution System The invention provides a non-stochastic gene modification system termed "optimized directed evolution system" to generate polypeptides, e.g., amylases or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, 1013 chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLABâ. (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new amylase phenotype is identified, re-isolated, again modified, re-tested for activity. This process can be iteratively repeated until a desired phenotype is engineered. For example, an entire biochemical anabolic or catabolic pathway can be engineered into a cell, including, e.g., starch hydrolysis activity.

Similarly, if it is determined that a particular oligonucleotide has no affect at all on the desired trait (e.g., a new amylase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, amylases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide (e.g., an amylase of the invention) and a second polynucleotide (e.g., an enzyme, such as an amylase of the invention or any other amylase, or, a tag or an epitope). The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides additional methods for making sequence variants of the nucleic acid (e.g., amylase) sequences of the invention. The invention also provides additional methods for isolating amylases using the nucleic acids and polypeptides of the invention. In one aspect, the invention provides for variants of an amylase coding sequence (e.g., a gene, cDNA or message) of the invention, which can be altered by any means, including, e.g., random or stochastic methods, or, non-stochastic, or "directed evolution," methods, as described above. The isolated variants may be naturally occurring. Variant can also be created in vitro.

Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250 (see also discussion, above).

The invention also provides variants of polypeptides of the invention (e.g., amylases) comprising sequences in which one or more of the amino acid residues (e.g., of an exemplary polypeptide, such as SEQ ID NO:2; SEQ ID NO:4; SEQ ID NO:6; SEQ ID NO:8; SEQ ID NO:10; SEQ ID NO:12) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary SEQ ID NO:2; SEQ ID NO:4; SEQ ID NO:6; SEQ ID NO:8; SEQ ID NO:10; SEQ ID NO:12, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., amylase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying amylase-encoding nucleic acids to modify codon usage. In one aspect, the invention provides methods for modifying codons in a nucleic acid encoding an amylase to increase or decrease its expression in a host cell. The invention also provides nucleic acids encoding an amylase modified to increase its expression in a host cell, amylase so modified, and methods of making the modified amylases. The method comprises identifying a "non-preferred" or a "less preferred" codon in amylase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an amylase isolated from a bacterial cell are modified such that the nucleic acid is optimally expressed in a bacterial cell different from the bacteria from which the amylase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in E. coli; Humphreys (2000) Protein Expr. Purif. 20:252-264, describing optimizing codon usage that affects secretion in E. coli.

Transgenic Non-Human Animals

The invention provides transgenic non-human animals comprising a nucleic acid, a polypeptide, an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study amylase activity, or, as models to screen for agents that change the amylase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing an amylase of the invention, or, a fusion protein comprising an amylase of the invention.

Transgenic Plants and Seeds

The invention provides transgenic plants and seeds comprising a nucleic acid, a polypeptide, an expression cassette or vector or a transfected or transformed cell of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's α-amylase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, wheat, rice, barley, and the like. Nucleic acids of the invention can be used to manipulate metabolic pathways of a plant in order to optimize or alter host's expression of α-amylase. The can change the ratio of starch/sugar conversion in a plant. This can facilitate industrial processing of a plant. Alternatively, alpha-amylases of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, Poa), forage grass such as *festuca, lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malta, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea*.

In alternative embodiments, the nucleic acids of the invention are expressed in plants which contain fiber cells, including, e.g., cotton, silk cotton tree (Kapok, *Ceiba pentandra*), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense,* and *G. hirsutum*.

The invention also provides for transgenic plants to be used for producing large amounts of the polypeptides of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

The invention provides isolated or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:2; SEQ ID NO:6; SEQ ID NO:8, SEQ ID NO:12, SEQ ID NO:14, or SEQ ID NO:16. As discussed above, the identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides (e.g., SEQ ID NO:2; SEQ ID NO:6; SEQ ID NO:8, SEQ ID NO:10, SEQ ID NO:12, SEQ ID NO:14, or SEQ ID NO:16). In alternative aspects, the invention provides polypeptides (peptides, fragments) ranging in size between about 5 and the full length of a polypeptide, e.g., an enzyme, such as an amylase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary amylase of the invention. Peptides of the invention can be useful as, e.g., labeling probes, antigens, toleragens, motifs, amylase active sites.

The polypeptides of the invention include amylases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include proteases inactive for other reasons, e.g., before "activation" by a post-translational processing event, e.g., an endo- or exo-peptidase or proteinase action, a phosphorylation event, an amidation, a glycosylation or a sulfation, a dimerization event, and the like.

The polypeptides of the invention include all active forms, including active subsequences, e.g., catalytic domains or active sites, of amylases of the invention. In one aspect, the invention provides catalytic domains or active sites as determined by a software paradigm, e.g., Pfam. In one aspect, the invention provides a peptide or polypeptide comprising or consisting of an active site domain as predicted through use of a database, e.g., Pfam, which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002).

Methods for identifying "prepro" domain sequences and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form.

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated or recombinant signal sequences, prepro sequences and catalytic domains (e.g., "active sites") comprising sequences of the invention.

The percent sequence identity can be over the full length of the polypeptide, or, the identity can be over a region of at least about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as a protease; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary amylase of the invention.

Peptides of the invention (e.g., a subsequence of an exemplary polypeptide of the invention) can be useful as, e.g., labeling probes, antigens, toleragens, motifs, amylase active sites (e.g., "catalytic domains"), signal sequences and/or prepro domains.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an amylase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431 A™ automated peptide synthesizer. Such equipment provides ready access to the peptides of the invention, either by direct synthesis or by synthesis of a series of fragments that can be coupled using other known techniques.

The invention provides novel amylases, including the exemplary enzymes having sequences as set forth in SEQ ID NO:2; SEQ ID NO:6; SEQ ID NO:8, SEQ ID NO:10, SEQ ID NO:12, SEQ ID NO:14 and SEQ ID NO:16, nucleic acids encoding them, antibodies that bind them, and methods for making and using them. In one aspect, the polypeptides of the invention have an amylase activity, as described herein, including, e.g., the ability to hydrolyze starches into sugars. In alternative aspects, the amylases of the invention have activities that have been modified from those of the exemplary amylases described herein. The invention includes amylases with and without signal sequences and the signal sequences themselves. The invention includes immobilized amylases, anti-amylase antibodies and fragments thereof. The invention provides methods for inhibiting amylase activity, e.g, using dominant negative mutants or anti-amylase antibodies of the invention. The invention includes heterocomplexes, e.g., fusion proteins, heterodimers, etc., comprising the amylases of the invention.

In one aspect, amylases of the invention hydrolyze internal $\alpha$-1,4- and 1,6-glucosidic bonds in starch to produce smaller molecular weight maltodextrines. In one aspect, this hydrolysis is largely at random. Thus, the invention provides methods for producing smaller molecular weight maltodextrines.

Amylases of the invention can be used in laboratory and industrial settings to hydrolyze starch or any maltodextrine-comprising compound for a variety of purposes. These amylases can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical or industrial samples.

For example, the amylases of the present invention can be formulated in laundry detergents to aid in the removal of starch-containing stains. Amylases of the invention can be used as cleaning agents in detergent matrices (see industrial applications below). The amylases of the present invention can be used in the initial stages (liquefaction) of starch processing, in wet corn milling, in alcohol production, in the textile industry for starch desizing, in baking applications, in the beverage industry, in oilfields in drilling processes; in inking of recycled paper; and in animal feed.

Amylases of the invention can have an amylase activity under various conditions, e.g., extremes in pH and/or temperature, oxidizing agents, and the like. The invention provides methods leading to alternative amylase preparations with different catalytic efficiencies and stabilities, e.g., towards temperature, oxidizing agents and changing wash conditions. In one aspect, amylase variants can be produced using techniques of site-directed mutagenesis and/or random mutagenesis. In one aspect, directed evolution can be used to produce a great variety of amylase variants with alternative specificities and stability.

The proteins of the invention are also useful as research reagents to identify amylase modulators, e.g., activators or inhibitors of amylase activity. Briefly, test samples (compounds, broths, extracts, and the like) are added to amylase assays to determine their ability to inhibit substrate cleavage. Inhibitors identified in this way can be used in industry and research to reduce or prevent undesired proteolysis. As with amylases, inhibitors can be combined to increase the spectrum of activity.

The invention also provides methods of discovering new amylases using the nucleic acids, polypeptides and antibodies of the invention. In one aspect, lambda phage libraries are screened for expression-based discovery of amylases. In one aspect, the invention uses lambda phage libraries in screening to allow detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening. The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

The present invention includes amylase enzymes which are non-naturally occurring carbonyl hydrolase variants (e.g., amylase variants) having a different proteolytic activity, stability, substrate specificity, pH profile and/or performance characteristic as compared to the precursor carbonyl hydrolase from which the amino acid sequence of the variant is derived. Specifically, such amylase variants have an amino acid sequence not found in nature, which is derived by substitution of a plurality of amino acid residues of a precursor amylase with different amino acids. The precursor amylase may be a naturally-occurring amylase or a recombinant amylase. The useful amylase variants encompass the substitution of any of the naturally occurring L-amino acids at the designated amino acid residue positions.

```
Exemplary SEQ ID NO: 2 has the sequence:
Met Arg Val Ser Ser Ile Gly Asn Gly Arg Met Leu Ile Asn Phe Asp Glu Lys Gly Arg Ile Val Asp Ile Tyr Tyr Pro Tyr Ile Gly Met Glu Asn Gln
```

```
-continued
Thr Ser Gly Asn Pro Ile Arg Leu Ala Ile Trp

Asp Lys Asp Lys Lys Val Ala Ser Leu Asp Glu Asp

Trp Glu Thr Thr Val Leu Tyr Ile Asp Glu

Ala Asn Met Val Glu Ile Arg Ser Asp Val Lys Glu

Leu Gly Leu Ser Leu Leu Ser Tyr Asn Phe

Leu Asp Ser Asp Asp Pro Ile Tyr Met Ser Ile Val

Lys Ile Ala Asn Asn Glu Asn Asn Ser Arg Asn

Ile Lys Val Phe Phe Ile His Asp Ile Asn Leu Tyr

Ser Asn Pro Phe Gly Asp Thr Ala Phe Tyr Asp

Pro Leu Pro Leu Ser Ile Ile His Tyr Lys Ser Lys

Arg Tyr Leu Ala Phe Lys Val Phe Thr Thr Val

Ser Thr Leu Ser Glu Tyr Asn Ile Gly Lys Gly Asp

Leu Ile Gly Asp Ile Tyr Asp Gly Asn Leu Gly

Leu Asn Gly Ile Glu Asn Gly Asp Val Asn Ser Ser

Met Gly Ile Glu Ile Asn Ile Asp Pro Asn Ser

Tyr Leu Lys Leu Tyr Tyr Val Ile Val Ala Asp Arg

Asn Leu Glu Gly Leu Arg Gln Lys Ile Arg

Lys Ile Asn Phe Ala Asn Val Glu Thr Ser Phe Thr

Leu Thr Tyr Met Phe Trp Arg Asn Trp Leu

Lys Lys Asn Lys Leu Phe Arg Asn Asn Leu Met Gln

Asp Ile Lys Arg Val Tyr Asp Val Ser Leu

Phe Val Ile Arg Asn His Met Asp Val Asn Gly Ser

Ile Ile Ala Ser Ser Asp Phe Ser Phe Val Lys

Ile Tyr Gly Asp Ser Tyr Gln Tyr Cys Trp Pro Arg

Asp Ala Ala Ile Ala Ala Tyr Ala Leu Asp Leu

Ala Gly Tyr Lys Glu Leu Ala Leu Lys His Phe Gln

Phe Ile Ser Asn Ile Ala Asn Ser Glu Gly Phe

Leu Tyr His Lys Tyr Asn Pro Asn Thr Thr Leu Ala

Ser Ser Trp His Pro Trp Tyr Tyr Lys Gly

Lys Arg Ile Tyr Pro Ile Gln Gly Asp Glu Thr Ala

Leu Glu Val Trp Ala Ile Ala Ser His Tyr Glu

Lys Tyr Glu Asp Ile Asp Glu Ile Leu Pro Leu Tyr

Lys Lys Phe Val Lys Pro Ala Leu Lys Phe

Met Met Ser Phe Met Glu Glu Gly Leu Pro Lys Pro

Ser Phe Asp Leu Trp Glu Glu Arg Tyr Gly

Ile His Ile Tyr Thr Val Ser Thr Val Tyr Gly Ala

Leu Thr Lys Gly Ala Lys Leu Ala Tyr Asp Val

Gly Asp Glu Ile Leu Ser Glu Asp Leu Ser Asp Thr

Ser Gly Leu Leu Lys Gly Met Val Leu Lys

Arg Met Thr Tyr Asn Gly Arg Phe Val Arg Arg Ile

Asp Glu Glu Asn Asn Gln Asp Leu Thr Val
```

Asp Ser Ser Leu Tyr Ala Pro Phe Phe Gly Leu

Val Asn Ala Asn Asp Lys Ile Met Ile Asn

Thr Ile Asn Glu Ile Glu Ser Arg Leu Thr Val Asn

Gly Gly Ile Ile Arg Tyr Glu Asn Asp Met Tyr

Gln Arg Arg Lys Lys Gln Pro Asn Pro Trp Ile Ile

Thr Thr Leu Trp Leu Ser Glu Tyr Tyr Ala Thr

Ile Asn Asp Lys Asn Lys Ala Asn Glu Tyr Ile Lys

Trp Val Ile Asn Arg Ala Leu Pro Thr Gly Phe

Leu Pro Glu Gln Val Asp Pro Glu Thr Phe Glu Pro

Thr Ser Val Thr Pro Leu Val Trp Ser His Ala

Glu Phe Ile Ile Ala Ile Asn Asn Ile

Exemplary SEQ ID NO: 4 has the sequence
Met Val Arg Tyr Thr Pro Leu Gly Asn Gly Arg Leu Leu Ile Ala Phe Asp Thr Asp Tyr Arg Ile Val Asp Phe Tyr Tyr Ser Lys Phe Ala Ser Glu Asn His Ser Ser Gly His Pro Phe Tyr Phe Gly Val Ser Val Asp Gly Asn Phe Asn Trp Ile Asp Arg Asn Ala Ile Lys His Met Asp Tyr Tyr Asp His Thr Met Val Ser Val Val Asn Tyr Thr His Asn Gly Ile Asp Phe Glu Asn Arg Asp Met Val Asp Ile Tyr Lys Asp Ile Phe Ile Arg Arg Val Val Ala Glu Asn Lys Thr Gly Lys Asp Val Asn Leu Lys Ile Phe Phe His Gln Asn Phe Tyr Ile Tyr Gly Asn Asp Ile Gly Asp Thr Ala Ala Tyr Phe Pro Glu Tyr Arg Gly Val Ile His Tyr Lys Gly Gly Arg Tyr Phe Leu Ala Ser Thr Leu Asp Glu Ser Gly Asn Phe Cys Asp Gln Tyr Ala Thr Gly Val Lys Asp Val Gly Glu Leu Lys Gly Thr Trp Lys Asp Ala Glu Asp Asn Glu Leu Ser Met Asn Pro Val Ala Ile Gly Ser Val Asp Ser Val Ile Arg His Ser Thr Thr Leu Lys Ala Gly Ser Lys Phe Thr Leu Tyr Tyr Phe Ile Ile Ala Gly Arg Asn Ile Asn Asp Ile Glu Ser Glu Tyr Ser Asn Val Asn Val Gln Tyr Leu Gln Lys Leu Leu Arg Arg Thr Thr Asn Tyr Trp Glu Leu Trp Ser Ser Lys Val Thr Pro Ser Leu Asp Ser Asp Thr Thr Ala Leu Tyr Arg Arg Ser Leu Phe Val Thr Lys Ser His Ala Asn Asp Leu Gly Ala Ile Ala Ala Ser Cys Asp Ser Asp Ile Leu Lys Leu Ser His Asp Gly Tyr Tyr Tyr Val Trp Pro Arg Asp Ala Ser Met Ala Ala Tyr Ala Leu Ser Ile Ser Gly His Ser Glu Thr Ala Arg Arg Phe Phe Ala Leu Met Glu Asp Ser Leu Ser Glu Glu Gly Tyr Leu Tyr His Lys Tyr Asn Val Asp Gly Lys Ile Ala Ser Ser Trp Leu Pro His Val Met Asn Gly Lys Ser Ile Tyr Pro Ile Gln Glu Asp Glu Thr Ala Leu Val Val Trp Ala Leu Trp Glu Tyr Phe Arg Lys Tyr Asn Asp Ile Gly Phe Thr Ala Pro Tyr Tyr Glu Arg Leu Ile Thr Arg Ala Ala Asp Phe Met Thr Asn Phe Val Asp Asn Asn Gly Leu Pro Lys Pro Ser Phe Asp Leu Trp Glu Glu Arg Tyr Gly Ile His Ala Tyr Thr Val Ala Thr Val Tyr Ala Ala Leu Lys Ala Ala Ser Asn Phe Ala Asn Val Phe Gly Asp Pro Asp Leu Ser Glu Lys Tyr Glu Asn Ala Ala Glu Arg Met Tyr His Ala Phe Asp Glu Arg Phe Tyr Ser Glu Asp Thr Gly Tyr Tyr Ala Arg Ala Ile Ile Asp Gly Lys Pro Asp Phe Thr Val Asp Ser Ala Leu Thr Ser Leu Val Leu Phe Gly Met Lys Asp Ala Asp Asp Pro Lys Val Ile Ser Thr Met Gln Arg Ile Ser Glu Asp Leu Trp Val Asn Gly Val Gly Gly Ile Ala Arg Tyr Gln Asn Asp Arg Tyr Met Arg Val Lys Asp Asp Pro Ser Val Pro Gly Asn Pro Trp Ile Ile Thr Thr Leu Trp Met Ala Arg Tyr Tyr Met Arg Phe Gly Asp Phe Glu Lys Ala Trp Asn Leu Ile Gln Trp Val Lys Ser His Arg Gln Lys Ser Gly Ile Phe Ser Glu Gln Ile Asn Pro Tyr Asn Gly Glu Pro Leu Ser Val Ser Pro Leu Val Trp Ser His Ser Glu Phe Ile Ile Ser Leu Leu Glu Tyr Ser Asp Leu Ile Arg Asn Arg Ser Exemplary SEQ ID NO: 6 has the sequence:
Met Ile Tyr Met Gly Gly Ile Ile Gly Asn Asn Asn Leu Leu Val Lys Ile Gly Asp Tyr Gly Glu Ile Ser Tyr Val Phe Tyr Pro His Val Gly Tyr Glu Thr His Phe Phe Asp Ser Ala Leu Ala Val Tyr Asp Lys Lys Val Lys Trp His Trp Asp Asp Asp Trp Asp Ile Ser Gln Lys Tyr Ile Glu Glu Thr Asn Ile Phe Lys Thr Ile Leu Glu Asp Asp Lys Ile Ile Leu Thr Ile Lys Asp Phe Val Pro Val Ser His Asn Val Ile Ile Arg Arg Leu His Ile Lys Asn Lys Leu Asp Lys Lys Leu Asn Phe Lys Leu Phe Phe Tyr Glu Asn Leu Arg Ile Gly Glu Tyr Pro Thr Glu Asn Ala Val Arg Phe Leu Glu Asp Glu Gly Cys Ile Val Lys Tyr Asn Glu Lys Tyr Val
Phe Cys Ile Gly Ser Asn Lys Lys Ile Asp Ser
Phe Gln Cys Gly Asn Arg Tyr Ser Lys Asn Ser Ala
Tyr Val Asp Ile Glu Asn Gly Leu Leu Met
Glu His Lys Glu Ser His Gly Leu Met Thr Asp Ser
Ala Ile Ser Trp Asn Ile Glu Ile Asp Lys Gly
Lys Ser Leu Ala Phe Asn Ile Tyr Ile Leu Leu Gln
Lys Phe Asp Gly Asp Leu Ser Ile Ile Thr Glu
Gln Leu Lys Ile Ile Met Asn Asn Thr Val His Ile
Lys Asp Leu Ser Met Asn Tyr Trp Lys Asn Ser
Ile Gly Asn Ile Lys Glu His Ile His Pro Gln Phe
His Ser Asp Lys Glu Ile Cys Pro Ile Ala Lys Arg
Ala Leu Met Val Leu Leu Met Leu Cys Asp Lys Asp
Gly Gly Ile Ile Ala Ala Pro Ser Leu His
Pro Asp Tyr Arg Tyr Val Trp Gly Arg Asp Gly Ala
Tyr Ile Ala Ile Ala Leu Asp Leu Phe Gly Ile
Arg Gly Ile Pro Asp Arg Phe Phe Glu Phe Met Ser
Lys Ile Gln Asn Asp Asp Gly Ser Trp Leu
Gln Asn Tyr Tyr Thr Asn Gly Lys Pro Arg Leu Thr
Ala Met Gln Ile Asp Gln Ile Gly Ser Ile Leu
Trp Ala Met Asp Val His Tyr Arg Leu Thr Gly Asn
Arg Lys Phe Val Glu Arg Tyr Trp Asn Thr
Ile Glu Lys Ala Gly Asn Tyr Leu Thr Ser Ala Ala
Leu Asn Phe Thr Pro Cys Phe Asp Leu Trp
Glu Glu Lys Phe Gly Val Phe Ala Tyr Thr Met Gly
Ala Ile Tyr Ala Gly Leu Lys Ala Ala Tyr Ser
Met Ser Lys Ala Val Asp Met Arg Asp Lys Val Lys
His Trp Glu Lys Ala Ile Glu Phe Leu Lys
Lys Glu Val Pro Arg Arg Phe Tyr Leu Glu Asp Glu
Glu Arg Phe Ala Lys Ser Ile Asn Pro Leu
Asp Lys Glu Ile Asp Ala Ser Ile Leu Gly Leu Ser
Tyr Pro Phe Asn Leu Ile Asp Val Asp Asp Glu
Arg Met Ile Lys Thr Ala Glu Ala Ile Glu Asn Ala
Phe Asn Tyr Lys Val Gly Gly Ile Gly Arg Tyr
Pro Asn Asp Val Tyr Phe Gly Gly Asn Pro Trp Ile
Ile Thr Thr Leu Trp Ile Ser Leu Tyr Tyr Arg
Arg Leu Ser Lys Val Leu Lys Glu Lys Asn Lys Asn
Asp Met Ala Glu Lys Tyr Leu Lys Lys Ser
Lys Lys Leu Phe Asp Trp Ala Val Lys Tyr Ser Phe
Asn Gly Leu Phe Pro Glu Gln Ile His Lys Asp Leu Gly Ile Pro Met Ser Ala Met Pro Leu Gly
Trp Ser Asn Ala Met Phe Leu Ile Tyr Leu
Tyr Lys Asp Asp Asn Val

```
Ala Ile Tyr Gly Gly Leu Lys Ser Gly Tyr

Leu Ile Gly Lys Glu Leu Asp Lys Glu Glu Ile

Gln His Trp Lys Lys Ser Met Asn Phe Leu

Lys Asn Glu Val Val Asn Arg Leu Tyr Leu Lys Asn

Glu Lys Arg Phe Ala Lys Ser Leu Lys Pro

Leu Asp Lys Thr Ile Asp Thr Ser Ile Leu Gly Leu

Ser Phe Pro Tyr Gly Leu Val Ser Val Asp

Asp Pro Arg Ile Ile Ser Thr Ala Asn Gln Ile Glu

Lys Ala Phe Asn Tyr Lys Val Gly Gly Val Gly

Arg Tyr Pro Glu Asp Ile Tyr Phe Gly Gly Asn Pro

Trp Ile Ile Thr Thr Leu Trp Leu Tyr Met Tyr

Tyr Lys Lys Leu Val Asp Thr Leu Ser Lys Lys Gly

Lys Phe Gln Glu Ser Ile Ile Asp Asn Tyr

Asn Lys Lys Cys Tyr Asn Leu Leu Lys Trp Ile Leu

Lys His Gln Phe Asn Gly Met Phe Pro Glu

Gln Val His Lys Asp Leu Gly Ile Pro Ile Ser Ala

Ile Pro Leu Gly Trp Ser His Ala Met Val Ile Ile

Ala Ile His Gly Asp Tyr Asp Ile Leu Ile Pro

Exemplary SEQ ID NO: 10 has the sequence
Met Ile Tyr Met Gly Gly Ile Val Gly Asn Asn Ser Leu Leu Ala Lys Ile Gly Asp Tyr Gly Glu Ile Glu Tyr Leu Phe Tyr Pro Gln Val Gly Tyr Glu Thr His Phe Phe Asp Ser Ala Leu Ala Val Tyr Asp Lys Lys Val Lys Trp His Trp Asp Asp Trp Asp Ile Thr Gln Lys Tyr Ile Glu Glu Thr Asn Ile Phe Lys Thr Ile Leu Glu Asp Asp Lys Ile Ile Leu Thr Ile Lys Asp Phe Val Pro Val Ser His Asn Val Leu Ile Arg Arg Val Tyr Ile Lys Asn Lys Leu Asp Lys Lys Leu Asn Phe Lys Leu Phe Phe Tyr Glu Asn Leu Arg Ile Gly Glu Asn Pro Ile Thr Asn Thr Val Lys Phe Leu Glu Asp Gly Cys Ile Val Lys Tyr Asn Gly Lys Tyr Ile Phe Cys Ile Gly Ser Asp Lys Arg Ile Asp Ser Phe Gln Cys Gly Asn Arg Tyr Ser Lys Thr Ser Ala Tyr Ile Asp Ile Glu Asn Gly Ile Leu Lys Glu His Lys Glu Ser Ser Gly Leu Leu Thr Asp Ser Ala Ile Ser Trp Asn Ile Lys Ile Asp Glu Lys Arg Ser Leu Ala Phe Asn Ile Tyr Ile Leu Pro Gln Arg Phe Asp Gly Asp Phe Ser Ile Ile Thr Glu Gln Leu Lys Ile Ile Met Asn Asn Ser Glu Asn Ile Lys Asn Leu Ser Met Asn Tyr Trp Lys His Ile Ile Gly Glu Ile Asn Arg Phe Ile His Pro Glu Leu Arg Gln Asn Asn Lys Ile Tyr Ser Ile Thr Lys Arg Ala Leu Met Thr Leu Leu Met Leu Cys Asp Lys Glu Gly Gly Ile Ile Ala Ala Pro Ser Leu His Pro Asp Tyr Arg Tyr Val Trp Gly Arg Asp Gly Ser Tyr Ile Ser Ile Ala Leu Asp Leu Phe Gly Ile Arg Asn Ile Pro Asp Arg Phe Phe Glu Phe Met Ser Lys Ile Gln Asn Ala Asp Gly Ser Trp Leu Gln Asn Tyr Tyr Val Asn Gly Lys Pro Arg Leu Thr Ala Ile Gln Thr Asp Gln Ile Gly Ser Ile Leu Trp Ala Met Asp Val His Tyr Arg Leu Thr Gly Asp Arg Lys Phe Val Glu Arg Tyr Trp Asn Thr Ile Glu Lys Ala Ala Asn Tyr Leu Arg Leu Val Ala Leu Asn Phe Thr Pro Cys Phe Asp Leu Trp Glu Glu Arg Phe Gly Val Phe Ala Tyr Thr Met Gly Ala Thr Tyr Ala Gly Leu Lys Cys Ala Tyr Ser Met Ser Lys Ala Val Asn Lys Arg Asp Lys Val Lys Asp Trp Gly Lys Thr Ile Glu Phe Leu Lys His Glu Val Pro Lys Arg Phe Tyr Leu Glu Asp Glu Glu Arg Phe Ala Lys Ser Ile Asn Pro Leu Asp Lys Thr Ile Asp Thr Ser Ile Leu Gly Leu Ser Tyr Pro Phe Asn Leu Ile Asp Val Asp Asp Glu Arg Met Ile Lys Thr Ala Glu Ala Ile Glu Lys Ala Phe Lys Tyr Lys Val Gly Gly Ile Gly Arg Tyr Pro Glu Asp Ile Tyr Phe Gly Gly Asn Pro Trp Ile Ile Thr Thr Leu Trp Leu Ser Leu Tyr Tyr Arg Arg Leu Tyr Lys Val Leu Lys Glu Lys Asp Asp Asn Gly Ala Asp Ile Tyr Leu Gln Leu Phe Pro Glu Gln Ile His Lys Glu Leu Gly Val Pro Met Ser Ala Met Pro Leu Gly Trp Ser Asn Ala Met Phe Leu Ile Tyr Val Tyr Glu Asn Asp Lys Val Ile Ile Pro Exemplary SEQ ID NO: 12 has the sequence
Met Val Ser Met Val Gly Ile Ile Gly Asn Gly Lys Ile Leu Ala Lys Ile Asp Asp Ser Gly Ser Leu Glu Tyr Ile Phe Phe Pro His Leu Gly His Glu Lys His Ile Phe Asp Ser Ser Phe Ala Ile Phe Tyr Asp Asn Lys Leu Lys Trp Asn Trp Asp Asn Ser Trp Asp Ile Asn Gln Asn Tyr Leu Lys Asp Thr Asn Ile Leu Lys Thr Ser Tyr Glu Asn Glu Asp Phe Leu Ile Glu Ser Lys Asp Tyr Val Pro Ile Ser
```

-continued

His Asn Ser Ile Ile Lys Gln Ile Ser Ile Leu Asn

Lys Ser Ser Glu Lys Lys Asn Leu Lys Leu Phe

Phe Tyr Glu Asn Leu Arg Met Gly Glu Ile Pro Glu

Val Ser Thr Val Lys Tyr Arg Lys Asn Arg

Glu Cys Ile Ile Lys Tyr Asp Lys Asn Tyr Val Phe

Cys Ile Gly Ser Asn Lys Lys Val Ser Ser Tyr

Gln Cys Gly Val Arg Ser Ser Glu Ser Ser Ala Leu

Asn Asp Leu Lys Asn Gly Ile Leu Lys Glu

Tyr Asp Ser Ala Glu Gly Leu Ile Thr Asp Ser Ala

Leu Gly Trp Asp Leu Glu Leu Ser Pro Asn

Gln Glu Gln Lys Val Ser Ile Phe Ile Phe Ala Asp
Lys Tyr Gly Gly Asp Tyr Thr Lys Ile Met Asn
Leu Leu Asp Thr Leu Asn Ile Val Ile Thr Asn His
Ala Asp Ile Tyr Asp Leu Thr Met Ala Tyr Trp
Lys Asn Met Ile Glu Thr Thr Ala Asn Ser Leu Cys
Asn Ser Asn Gln Val Phe Lys Asp Leu Thr
His Ile Lys Asp Asp Ala Asn Ile Ser Asn Leu Lys
Arg Ile Lys Gln Tyr Glu Ala Ile Cys Lys Arg
Ser Leu Leu Thr Ile Leu Leu Leu Cys Asp His Asn
Gly Gly Ile Ile Ala Ser Pro Ser Leu Tyr Pro
Asp Tyr Arg Tyr Val Trp Cys Arg Asp Ala Gly Tyr
Met Ala Val Ala Leu Asp Leu Cys Gly Gln
His Gly Ile Ser Glu Lys Tyr Phe Glu Trp Cys Lys
Lys Thr Gln Asn Ser Asp Gly Ser Trp Val Gln
Asn Tyr Tyr Val Glu Gly Asn Pro Arg Leu Thr Ala
Ile Gln Ile Asp Gln Val Gly Thr Thr Ile Trp
Ala Ala Leu Val His Tyr Arg Ile Thr Arg Asp Lys
Leu Phe Leu Asn Arg Tyr Trp Glu Met Ile
Lys Lys Ala Gly Asp Tyr Leu Ser Ser Val Ala Asn
Pro Pro Ser Pro Ser Tyr Asp Leu Trp Glu
Glu Lys Tyr Gly Val Phe Ala Tyr Thr Leu Gly Ala
Ile Tyr Gly Gly Leu Lys Ser Ala Tyr Asn Ile
Cys Lys Ile Leu Gly Lys Glu Glu His Asp Ile Gln
Asn Trp Lys Glu Ser Met Asp Phe Leu Lys
Asn Glu Met Val Asp Arg Leu Tyr Leu Lys Asp Glu
Asn Arg Phe Ala Lys Ser Leu Asp Pro Leu
Asp Lys Ala Leu Asp Ala Ser Ile Leu Gly Leu Ser
Phe Pro Tyr Asn Leu Val Pro Val Asp Asp
Pro Arg Met Ile Ser Thr Ala Asn Gln Ile Glu Asn
Ala Phe Lys Tyr Lys Val Gly Gly Ile Gly Arg
Tyr Pro Glu Asp Val Tyr Phe Gly Gly Asn Pro Trp

-continued

Ile Ile Thr Thr Ile Trp Leu His Met Tyr Tyr
Glu Asn Leu Ile Lys Ser Leu Ser Lys His Gly Lys
Asn Ala Ile His Ser Asp Gln Ile Pro Asp Ser
Ser Gly Asp Leu Lys Asp Phe Val Ser Ile Ile Gly
Ser Ile Glu Asn His Gly Glu Lys Ser Asp Glu
Thr Pro Ser Ser Asp Thr Leu Leu Thr Tyr Ala Gln
Lys Cys Asn Asn Leu Phe Asp Trp Thr Leu
Lys Tyr Asn Phe Asn Glu Leu Phe Pro Glu Gln Val
His Lys Asp Leu Gly Ala Pro Ile Ser Ala Ile
Pro Leu Gly Trp Ser His Ala Met Val Ile Ile Ala
Ile His Gly Asn Phe Asp Ile Leu Ile Pro

Exemplary SEQ ID NO: 14 has the sequence:

Met Ile Val Gly Asn Asn Ser Phe Leu Cys Lys Ile
Gly Asp His Gly Glu Ile Glu Tyr Ala Phe Tyr
Pro His Val Gly Tyr Glu Leu His Phe Phe Asp Ser
Ser Leu Ala Ile Tyr Asp Lys Glu Ile Met Trp
Ile Trp Asp Lys Glu Trp Ser Val Tyr Gln Lys Tyr
Ile Glu Asp Thr Asn Ile Phe Lys Thr Thr Leu
Glu Asn Glu Asn Ile Ile Phe Val Ile Lys Asp Leu
Val Pro Ile Ser His Asn Val Leu Ile Arg Arg
Val Phe Ile Lys Asn Lys Leu Pro Tyr Asn Tyr Asn
Phe Lys Leu Phe Phe Tyr Glu Asn Leu Arg
Ile Gly Glu His Pro Ser Glu Asn Thr Val Lys Phe
Leu Asp Asp Cys Ile Val Lys Phe Asn Gly
Lys Tyr Thr Phe Cys Ile Ser Ser Asp Lys Lys Ile
Asn Ser Tyr Gln Cys Gly Asn Arg Tyr Ser Glu
Lys Ser Ala Tyr Lys Asp Ile Glu Asn Gly Leu Leu
Ser Glu Asn Pro Glu Ser Val Gly Val Leu
Thr Asp Ser Ala Ile Glu Trp Asp Ile Asp Leu Lys
Pro His Gly Lys Val Ala Phe Asn Ile Tyr Ile
Phe Pro His Ile Gly Asn Asn Ile Glu Ile Ile Lys
Asn Gln Leu Asn Ile Ile Lys Asn Leu Ser Ser
Glu Ile Lys Asn Ile Ser Leu Asn Tyr Trp Lys Ser
Ser Phe Asp Ile Lys Gly Tyr Leu Phe Asn Glu
Lys Tyr Leu Lys Leu Ala Lys Arg Ala Leu Met Ile
Leu Thr Met Leu Ser Asp Lys Asn Gly Gly
Ile Ile Ala Ser Pro Ser Ile His Pro Asp Tyr Arg
Tyr Val Trp Gly Arg Asp Gly Ser Tyr Met Ala
Val Ala Leu Ser Ile Tyr Gly Ile Lys Asn Ile Pro
Trp Arg Phe Phe His Phe Met Ser Lys Val Gln
Asn Leu Asp Gly Ser Trp Leu Gln Asn Tyr Tyr Thr

```
Asp Gly Lys Pro Arg Leu Thr Ala Leu Gln
Ile Asp Gln Ile Gly Ser Val Leu Trp Ala Met Glu
Val Tyr Tyr Arg Thr Thr Gly Asp Arg Glu Phe
Val Lys Lys Phe Trp Glu Thr Ile Glu Lys Ala Gly
Asn Phe Leu Tyr Asn Ala Ser Leu Ser Leu
Met Pro Cys Phe Asp Leu Trp Glu Glu Lys Tyr Gly
Val Phe Ser Tyr Thr Leu Gly Ala Met Tyr
Gly Gly Leu Arg Ala Gly Cys Ser Leu Ala Lys Ala
Ile Glu Glu Lys Lys Glu Asp Trp Lys Lys
Ala Leu Asp Lys Leu Lys Lys Asp Val Asp Leu Leu
Tyr Leu Ser Asp Glu Glu Arg Phe Val Lys
Ser Ile Asn Pro Leu Asn Lys Glu Ile Asp Thr Ser
Ile Leu Gly Leu Ser Tyr Pro Phe Gly Leu Val
Lys Val Asn Asp Glu Arg Met Ile Lys Thr Ala Glu
Ala Ile Glu Lys Ala Phe Lys Tyr Lys Val
Gly Gly Ile Gly Arg Tyr Pro Ser Asp Val Tyr Phe
Gly Gly Asn Pro Trp Ile Ile Thr Thr Leu Trp
Leu Ala Leu Tyr Tyr Arg Arg Leu Phe Ile Thr Thr
Asn Asp Arg Lys Tyr Leu Glu Lys Ser Lys
Lys Leu Phe Asn Trp Val Ile Asn His Ile Tyr Leu
Ph

-continued

```
Gly Met Tyr Glu Ile Ala Ala Glu Tyr Asp Asp Val

Ile Ile Ile Lys Thr Arg Ile Gly Leu Leu Lys

Gly Ser Arg Ile Arg Phe Glu Tyr Asp Ile Val Lys

Glu Asp Glu Asn Lys Leu Leu Ala Gln Gly

Met Thr Glu His Pro Phe Thr Thr Leu Asp Arg Lys

Pro Val Asn Ile Lys Lys Ile Leu Pro His Val

Tyr Glu Met Leu Asn Lys Cys Tyr Asp Asp Gly Val
```

Amylase Signal Sequences

The invention also provides amylase-encoding nucleic acids comprising signal sequences. In one aspect, the signal sequences of the invention are identified following identification of novel amylase polypeptides.

The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The sequences vary in length from 13 to 36 amino acid residues. Various methods of recognition of signal sequences are known to those of skill in the art. For example, in one aspect, novel amylase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects amylases of the invention may not have signal sequences. It may be desirable to include a nucleic acid sequence encoding a signal sequence from one amylase operably linked to a nucleic acid sequence of a different amylase or, optionally, a signal sequence from a non-amylase protein may be desired. Table 3 shows signal sequences of the invention.

Amylase Signal Sequences, Prepro and Catalytic Domains

The invention provides amylase signal sequences (e.g., signal peptides (SPs)), prepro domains and catalytic domains (CDs). The SPs, prepro domains and/or CDs of the invention can be isolated or recombinant peptides or can be part of a fusion protein, e.g., as a heterologous domain in a chimeric protein. The invention provides nucleic acids encoding these catalytic domains (CDs), prepro domains and signal sequences (SPs, e.g., a peptide having a sequence comprising/consisting of amino terminal residues of a polypeptide of the invention).

In one aspect, the invention provides a signal sequence comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 (or a longer peptide) of a polypeptide of the invention.

The amylase signal sequences (SPs) and/or prepro sequences of the invention can be isolated peptides, or, sequences joined to another protease or a non-protease polypeptide, e.g., as a fusion (chimeric) protein. In one aspect, the invention provides polypeptides comprising amylase signal sequences of the invention. In one aspect, polypeptides comprising amylase signal sequences SPs and/or prepro of the invention comprise sequences heterologous to an amylase of the invention (e.g., a fusion protein comprising an SP and/or prepro of the invention and sequences from another amylase or a non-amylase protein). In one aspect, the invention provides amylases of the invention with heterologous SPs and/or prepro sequences, e.g., sequences with a yeast signal sequence. An amylase of the invention can comprise a heterologous SP and/or prepro in a vector, e.g., a pPIC series vector (Invitrogen, Carlsbad, Calif.).

In one aspect, SPs and/or prepro sequences of the invention are identified following identification of novel amylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence.

This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from 13 to 36 or more amino acid residues. Various methods of recognition of signal sequences are known to those of skill in the art. For example, in one aspect, novel amylase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects amylases of the invention may not have SPs and/or prepro sequences, or "domains." In one aspect, the invention provides the amylases of the invention lacking all or part of an SP and/or a prepro domain. In one aspect, the invention provides a nucleic acid sequence encoding a signal sequence (SP) and/or prepro from one amylase operably linked to a nucleic acid sequence of a different amylase or, optionally, a signal sequence (SPs) and/or prepro domain from a non-amylases protein may be desired.

The invention also provides isolated or recombinant polypeptides comprising signal sequences (SPs), prepro domain and/or catalytic domains (CDs) of the invention and heterologous sequences. The heterologous sequences are sequences not naturally associated (e.g., to an amylase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., an amylase sequence). Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Hybrid Amylases and Peptide Libraries

In one aspect, the invention provides hybrid amylases and fusion proteins, including peptide libraries, comprising sequences of the invention. The peptide libraries of the invention can be used to isolate peptide modulators (e.g., activators or inhibitors) of targets, such as amylase substrates, receptors, enzymes. The peptide libraries of the invention can be used to identify formal binding partners of targets, such as ligands, e.g., cytokines, hormones and the like.

In one aspect, the fusion proteins of the invention (e.g., the peptide moiety) are conformationally stabilized (relative to linear peptides) to allow a higher binding affinity for targets. The invention provides fusions of amylases of the invention and other peptides, including known and random peptides. They can be fused in such a manner that the structure of the amylases is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g, an allelic or interspecies variation of an amylase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed amylase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using assays of proteolytic activities. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides amylases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. amylase activity) although variants can be selected to modify the characteristics of the amylases as needed.

In one aspect, amylases of the invention comprise epitopes or purification tags, signal sequences or other fusion sequences, etc. In one aspect, the amylases of the invention can be fused to a random peptide to form a fusion polypeptide. By "fused" or "operably linked" herein is meant that the random peptide and the amylase are linked together, in such a manner as to minimize the disruption to the stability of the amylase structure, e.g., it retains amylase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for amylase activity, to screen compounds as potential modulators, e.g., activators or inhibitors, of an amylase activity, for antibodies that bind to a polypeptide of the invention, for nucleic acids that hybridize to a nucleic acid of the invention, to screen for cells expressing a polypeptide of the invention and the like.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of an amylase gene. One or more, or all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277, 489; 6,261,776; 6,258,606; 6,054,270; 6,048,695; 6,045, 996; 6,022,963; 6,013,440; 5,965,452; 5,959,098; 5,856, 174; 5,830,645; 5,770,456; 5,632,957; 5,556,752; 5,143, 854; 5,807,522; 5,800,992; 5,744,305; 5,700,637; 5,556, 752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to an amylase of the invention. These antibodies can be used to isolate, identify or quantify the amylases of the invention or related polypeptides. These antibodies can be used to isolate other polypeptides within the scope the invention or other related amylases. The antibodies can be designed to bind to an active site of an amylase. Thus, the invention provides methods of inhibiting amylases using the antibodies of the invention.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies which bind specifically to the polypeptides, e.g., the amylases, of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides (e.g., amylases) from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, transgenic seeds or plants or plant parts, polypeptides (e.g., amylases) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new cell strain having a new phenotype, e.g., a new or modified amylase activity, by modifying the genetic composition of the cell. The genetic composition can be modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the amylases of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., an amylase message) or generating new (e.g., amylase) transcripts in a cell. This increased or decreased expression can be traced by testing for the presence of an amylase of the invention or by amylase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., an amylase) or generating new polypeptides in a cell. This increased or decreased expression can be traced by determining the amount of amylase present or by amylase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial Applications

Detergent Compositions

The invention provides detergent compositions comprising one or more polypeptides of the invention, and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Amylases of the invention can facilitate the removal of starchy stains by means of catalytic hydrolysis of the starch polysaccharide. Amylases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of amylase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Amylases of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of amylases of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A polypeptide of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations. In alternative aspects, detergent additives and detergent compositions of the invention may comprise one or more other enzymes such as a protease, a lipase, a cutinase, another amylase, a carbohydrase, a cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, amylase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

Treating Fabrics

The invention provides methods of treating fabrics using one or more polypeptides of the invention. The polypeptides of the invention can be used in any fabric-treating method, which are well known in the art, see, e.g., U.S. Pat. No. 6,077,316. For example, in one aspect, the feel and appearance of a fabric is improved by a method comprising contacting the fabric with an amylase of the invention in a solution. In one aspect, the fabric is treated with the solution under pressure.

In one aspect, the enzymes of the invention are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes of the invention can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. The invention provides a method of desizing comprising enzymatic hydrolysis of the size by the action of an enzyme of the invention.

The enzymes of the invention can be used to desize fabrics, including cotton-containing fabrics, as detergent additives, e.g., in aqueous compositions. The invention provides methods for producing a stonewashed look on indigo-dyed denim fabric and garments. For the manufacture of clothes, the fabric can be cut and sewn into clothes or garments, that is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments (e.g., a "bio-stoning process"), enzymatic desizing and providing softness to fabrics using the amylases of the invention. The invention provides methods for quickly softening denim garments in a desizing and/or finishing process.

Foods and Food Processing

The enzymes of the invention have numerous applications in food processing industry. The amylases of the invention are used in starch to fructose processing. Starch to fructose processing can consist of four steps: liquefaction of granular starch, saccharification of the liquefied starch into dextrose, purification, and isomerization to fructose.

The invention provides methods of starch liquefaction using the enzymes of the invention. Concentrated suspensions of starch polymer granules are converted into a solution of soluble shorter chain length dextrins of low viscosity. This step is useful for convenient handling with standard equipment and for efficient conversion to glucose or $10^3$ other sugars. In one aspect, the granular starch is liquefied by gelatinizing the granules by raising the temperature of the granular starch to over about 72° C. The heating process instantaneously disrupts the insoluble starch granules to produce a water soluble starch solution. The solubilized starch solution can then be liquefied by an amylase of the invention. Thus, the invention provides enzymatic starch liquefaction processes using an amylase of the invention.

An exemplary enzymatic liquefaction process involves adjusting the pH of a granular starch slurry to between 6.0 and 6.5 and the addition of calcium hydroxide, sodium hydroxide or sodium carbonate. In one aspect, calcium hydroxide is added. This provides calcium ions to stabilize the glucoamylase of the invention against inactivation. In one aspect, upon addition of amylase, the suspension is pumped through a steam jet to instantaneously raise the temperature to between 80°–115° C. In one aspect, the starch is immediately gelatinized and, due to the presence of amylase, depolymerized through random hydrolysis of $\alpha$-1, 4-glycosidic bonds by amylase to a fluid mass. The fluid mass can be easily pumped.

The invention provides various enzymatic starch liquefaction processes using an amylase of the invention. In one aspect of the liquefaction process of the invention, an amylase is added to the starch suspension and the suspension is held at a temperature of between about 80°–100° C. to partially hydrolyze the starch granules. In one aspect, the partially hydrolyzed starch suspension is pumped through a jet at temperatures in excess of about 105° C. to thoroughly gelatinize any remaining granular structure. In one aspect, after cooling the gelatinized starch, a second addition of amylase is made to further hydrolyze the starch.

The invention provides enzymatic dry milling processes using an amylase of the invention. In dry milling, whole grain is ground and combined with water. The germ is optionally removed by flotation separation or equivalent techniques. The resulting mixture, which contains starch, fiber, protein and other components of the grain, is liquefied using amylase. In one aspect, enzymatic liquefaction is done at lower temperatures than the starch liquification processes discussed above. In one aspect, after gelatinization the starch solution is held at an elevated temperature in the presence of amylase until a DE of 10-20 is achieved. In one aspect, this is a period of about 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The invention provides wet milling processes, e.g., corn wet milling, using an amylase of the invention. Corn wet milling is a process which produces corn oil, gluten meal, gluten feed and starch. Thus, the invention provides methods of making corn oil, gluten meal, gluten feed and starch using an enzyme of the invention. In one aspect, an alkaline-amylase of the invention is used in the liquefaction of starch. In one aspect, glucoamylase is used in saccharification to produce glucose.

In one aspect, corn (a kernel that consists of a outer seed coat (fiber), starch, a combination of starch and glucose and the inner germ), is subjected to a four step process, which results in the production of starch. In one aspect, the corn is steeped, de-germed, de-fibered, and the gluten is separated. In a steeping process the solubles are taken out. The product remaining after removal of the solubles is de-germed, resulting in production of corn oil and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification using polypeptides of the invention to produce glucose.

The invention provides anti-staling processes (e.g., of baked products such as bread) using an amylase of the invention. The invention provides methods to slow the increase of the firmness of the crumb (of the baked product) and a decrease of the elasticity of the crumb using an amylase of the invention. Staling of baked products (such as bread) is more serious as time passes between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. Amylases of the invention are used to retard staling of the bread as described e.g., in U.S. Pat. Nos. 6,197,352; 2,615,810 and 3,026,205; Silberstein (1964) Baker's Digest 38:66-72.

In one aspect, an enzyme of the invention is used to retard the staling of baked products while not hydrolyzing starch into the branched dextrins. Branched dextrins are formed by cleaving off the branched chains of the dextrins generated by α-amylase hydrolysis which cannot be degraded further by the α-amylase. This can produce a gummy crumb in the resulting bread. Accordingly, the invention provides a process for retarding the staling of baked products (e.g., leavened baked products) comprising adding an enzyme of the invention comprising exoamylase activity to a flour or a dough used for producing a baked product. Exoamylases of the invention can have glucoamylase, β-amylase (which releases maltose in the beta-configuration) and/or maltogenic amylase activity.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase.

The invention also provides a high yield process for producing high quality corn fiber gum by treatment of corn fiber with an enzyme of the invention followed by hydrogen peroxide treatment to obtain an extract of milled corn fiber. See, e.g., U.S. Pat. No. 6,147,206.

Animal Feeds and Additives

The invention provides methods for treating animal feeds and additives using amylase enzymes of the invention. The invention provides animal feeds and additives comprising amylases of the invention. In one aspect, treating animal feeds and additives using amylase enzymes of the invention can help in the availability of starch in the animal feed or additive. This can result in release of readily digestible and easily absorbed sugars.

Use of an amylase of the invention can increase the digestive capacity of animals and birds. Use of an amylase of the invention can ensure availability of an adequate nutrient supply for better growth and performance. In one aspect, the enzymes of the invention can be added as feed additives for animals. In another aspect, the animal feed can be treated with amylases prior to animal consumption. In another aspect, the amylases may be supplied by expressing the enzymes directly in transgenic feed crops (as, e.g., transgenic plants, seeds and the like), such as corn. As discussed above, the invention provides transgenic plants, plant parts and plant cells comprising a nucleic acid sequence encoding a polypeptide of the invention. In one aspect, the nucleic acid is expressed such that the amylase is produced in recoverable quantities. The amylase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

Paper or Pulp Treatment

The enzymes of the invention can be in paper or pulp treatment or paper deinking. For example, in one aspect, the invention provides a paper treatment process using amylases of the invention. In one aspect, the enzymes of the invention can be used to modify starch in the paper thereby converting it into a liquefied form. In another aspect, paper components of recycled photocopied paper during chemical and enzymatic deinking processes. In one aspect, amylases of the invention can be used in combination with cellulases. The paper can be treated by the following three processes: 1) disintegration in the presence of an enzyme of the invention, 2) disintegration with a deinking chemical and an enzyme of the invention, and/or 3) disintegration after soaking with an enzyme of the invention. The recycled paper treated with amylase can have a higher brightness due to removal of toner particles as compared to the paper treated with just cellulase. While the invention is not limited by any particular mechanism, the effect of an amylase of the invention may be due to its behavior as surface-active agents in pulp suspension.

The invention provides methods of treating paper and paper pulp using one or more polypeptides of the invention. The polypeptides of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of an enzyme of the invention (other enzymes can also be added). In another aspect, the invention provides a method for enhancing the freeness of pulp, e.g., pulp made from secondary fiber, by adding an enzymatic mixture comprising an enzyme of the invention (can also include other enzymes, e.g., pectinase enzymes) to the pulp and treating under conditions to cause a reaction to produce an enzymatically treated pulp. The freeness of the enzymatically treated pulp is increased from the initial freeness of the secondary fiber pulp without a loss in brightness.

Repulping: Treatment of Lignocellulosic Materials

The invention also provides a method for the treatment of lignocellulosic fibers, wherein the fibers are treated with a polypeptide of the invention, in an amount which is efficient for improving the fiber properties. The amylases of the invention may also be used in the production of lignocellulosic materials such as pulp, paper and cardboard, from starch reinforced waste paper and cardboard, especially where repulping occurs at pH above 7 and where amylases can facilitate the disintegration of the waste material through degradation of the reinforcing starch. The amylases of the invention can be useful in a process for producing a papermaking pulp from starch-coated printed paper. The process may be performed as described in, e.g., WO 95/14807.

An exemplary process comprises disintegrating the paper to produce a pulp, treating with a starch-degrading enzyme before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein the polypeptide is applied in an amount which is efficient for effective de-inking of the fiber surface.

Waste Treatment

The enzymes of the invention can be used in a variety of other industrial applications, e.g., in waste treatment. For example, in one aspect, the invention provides a solid waste digestion process using enzymes of the invention. The methods can comprise reducing the mass and volume of substantially untreated solid waste. Solid waste can be treated with an enzymatic digestive process in the presence of an enzymatic solution (including an enzyme of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

Oral Care Products

The invention provides oral care product comprising an amylase of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

Brewing and Fermenting

The invention provides methods of brewing (e.g., fermenting) beer comprising an amylase of the invention. In one exemplary process, starch-containing raw materials are disintegrated and processed to form a malt. An amylase of the invention is used at any point in the fermentation process. For example, amylases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15-25° C. for 3 to 6 days when enzyme synthesis is stimulated under the control of gibberellins. During this time amylase levels rise significantly. In one aspect, amylases of the invention are added at this (or any other) stage of the process. The action of the amylase results in an increase in fermentable reducing sugars. This can be expressed as the diastatic power, DP, which can rise from around 80 to 190 in 5 days at 12° C.

Amylases of the invention can be used in any beer producing process, as described, e.g., in U.S. Pat. Nos. 5,762,991; 5,536,650; 5,405,624; 5,021,246; 4,788,066.

Other Industrial Applications

The invention also includes a method of increasing the flow of production fluids from a subterranean formation by removing a viscous, starch-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

In summary, the invention provides enzymes and processes for hydrolyzing liquid (liquefied) and granular starch. Such starch can be derived from any source, e.g., corn, wheat, milo, sorghum, rye or bulgher. The invention applies to any grain starch source which is useful in liquefaction, e.g., any other grain or vegetable source known to produce starch suitable for liquefaction. The methods of the invention comprise liquefying starch from any natural material, such as rice, germinated rice, corn, barley, milo, wheat, legumes and sweet potato. The liquefying process can substantially hydrolyze the starch to produce a syrup. The temperature range of the liquefaction can be any liquefaction temperature which is known to be effective in liquefying starch. For example, the temperature of the starch can be between about 80° C. to about 115° C., between about 100° C. to about 110° C., and from about 105° C. to about 108° C.

In other aspects, amylases of the invention can be used in biodefense (e.g., destruction of spores or bacteria). Use of amylases in biodefense applications offer a significant benefit, in that they can be very rapidly developed against any currently unknown biological warfare agents of the future. In addition, amylases of the invention can be used for decontamination of affected environments. Additionally, amylases of the invention can be used in biofilm degradation, in biomass conversion to ethanol, and/or in the personal care and cosmetic industry.

EXAMPLES

Example 1: Exemplary Protocol for Liquefying Starch and Measuring Results

The following example described and exemplary protocol for liquefying starch using selected amylases of the invention.

Amylases having a sequence as set forth in SEQ ID NO:10 and SEQ ID NO:4 demonstrated activity on liquefied starch at pH 4.5 or 6.5 using the reaction conditions show below.

Reaction Conditions: 100 mM $PO_4$ pH 6.5, 1% (w/w) liquefied starch DE 12 at 55° C. Both TLC and HPLC assays were done to verify activity. The data from both assays showed that the clones were active.

pH profiles for the amylases having a sequence as set forth in SEQ ID NO:4 and SEQ ID NO:10 were run using phosphate buffer pHed from 3.0-6.5, at 55° C. From the amount of observable hydrolysis, it could be visually said that the clones were more active at certain pH values than at other values at the above indicated reaction conditions:

SEQ ID NO:4—active from pH 5.0-6.5
SEQ ID NO:10—active from pH 4.5-6.5
An exemplary protocol for the saccharification of liquefied starch at pH 6.5:
  Adjust the pH of the liquefied starch to the pH at which the saccharification(s) will be performed. Liquefy starch in 100 mM sodium acetate buffer, pH 4.5 with 100 mM sodium phosphate salts added so that before saccharification, the pH could be adjusted to pH 6.5.
  Weigh 5 gram samples of liquefied starch into tared bottles.
  Use 0.04% (w/w) Optidex L-400 or approximately 400 mL of 1-10 diluted stock Optidex L-400 per 100 grams of liquefied starch.
  Calculate the milligrams of Optidex L-400 contained in the 400 mL of 1-10 diluted stock Optidex L-400. Next, calculate the volume of lysates needed to give the same concentration of enzyme as the Optidex L-400.
  Add enzymes to liquefied starch samples and incubate at desired temperature) (50 C.°). After 18 hours determine DE and prepare a sample for HPLC analysis.
An exemplary DE Determination:
Exemplary Neocuproine Assay:
A 100 ml sample was added to 2.0 ml of neocuproine solution A (40 g/L sodium carbonate, 16 g/L glycine, 0.45 g/L copper sulfate). To this was added 2.0 ml of neocuproine solution B (1.2 g/L neocuproine hydrochloride-Sigma N-1626). The tubes were mixed and heated in a boiling water bath for 12 minutes; cooled, diluted to 10 ml volume with DI water and the OD read at 450 nm on the spectrophotometer. The glucose equivalent in the sample was extrapolated from the response of a 0.2 mg/ml glucose standard run simultaneously.

Exemplary HPLC Analysis:
Saccharification carbohydrate profiles are measured by HPLC (Bio-Rad Aminex HPX-87A column in silver form, 80° C.) using refractive index detection. Mobile phase is filtered Millipore water used at a flow rate of 0.7 ml/min. Saccharification samples are diluted 1-10 with acidified DI water (5 drops of 6 M HCl into 200 mL DI water) then filtered through a 0.45 mm syringe filter. Injection volume is 20 uL.

Exemplary TLC:
Reaction products were w/d at hourly timepoints and spotted and dried on a TLC plate. The Plate was then developed in 10:90 water:isopropanol and visualized with either a vanillin stain or CAM stain and then heated to show reducible sugars. The liquefied starch was partially hydrolyzed to glucose in cases where activity was observed.

A number of embodiments of the invention have been described. Nevertheless, it will be understood that various modifications may be made without departing from the spirit and scope of the invention. Accordingly, other embodiments are within the scope of the following claims.

SEQUENCE LISTING

```
<160> NUMBER OF SEQ ID NOS: 16

<210> SEQ ID NO 1
<211> LENGTH: 1854
<212> TYPE: DNA
<213> ORGANISM: Unknown
<220> FEATURE:
<223> OTHER INFORMATION: DNA derived from Archaea

<400> SEQUENCE: 1
atgagagttt cctccatagg aaatggcaga atgctgataa actttgatga gaaaggaaga      60
atagtcgata tttattatcc ttatatagga atggagaacc agacttctgg aaacccaatt     120
aggttagcta tttgggacaa agataagaaa gtggcatctc tagatgagga ttgggaaact     180
actgtattat atatagatga agctaatatg gttgagatta ggagtgatgt taaggagtta     240
ggactttctc ttctctctta aactttcta gattctgatg atccgatata tatgtctatt      300
gtaaaaatag caaataacga aaataatagc agaaatataa aagtattttt tatacatgat     360
ataaatttat attcaaaccc ttttggggac actgcattct atgatcccct acccctttca     420
attatacatt ataagtctaa acgatattta gcctttaaag tgtttaccac ggtatcgaca     480
ctttctgagt ataacatagg caaaggtgac ttaattggag atatttatga tggcaattta     540
ggacttaatg gtatagaaaa tggtgatgta aattcaagta tgggtataga gataaatata     600
gatcctaatt cctatttgaa attatactac gtaatagtcg cagatagaaa cttggaaggc     660
ttaaggcaaa aaataaggaa aataaacttt gcaaacgtag agacatcgtt tacgttaacc     720
tatatgtttt ggcggaattg gttaagaaaa aataaactct tcagaaataa tttaatgcag     780
gatattaaga gagtctatga tgtgagtctt tttgtgataa gaaatcacat ggacgttaac     840
gggtcaataa tagcttcctc agacttctcc ttcgtcaaga tttatgggga ctcatatcag     900
tattgttggc ctagagatgc ggcaattgca gcttatgctc tagatctagc tggctataag     960
```

-continued

```
gaactagcat taaaacactt ccagttcatt tctaatattg caaattctga aggcttccta    1020
tatcataaat ataatccaaa tacaactcta gctagttctt ggcatccttg gtattataaa    1080
ggtaaaagga tatacccaat tcaaggggat gagacggcat tagaagtatg ggcaatagct    1140
agtcattacg aaaaatatga agatattgac gaaatacttc cattatataa gaagttcgtg    1200
aagccagcct taaaatttat gatgtctttt atggaagaag gattgccaaa accttctttt    1260
gacctatggg aagaaggta tggtatacat atttacacag tatctacggt ttacggcgca    1320
ttaacaaagg gagcaaagtt agcttatgat gtaggtgatg aaatattaag tgaagattta    1380
agtgatacat cgggtttatt aaaaggaatg gttttgaaaa gaatgactta taatggaaga    1440
tttgttagaa gaatagacga ggaaaataac caagatctaa ctgtggactc aagtctctat    1500
gctccattct tctttggtct tgttaatgca aatgacaaaa tcatgataaa taccattaac    1560
gagattgaaa gcagattaac tgtgaatggc gggataataa ggtatgagaa tgatatgtat    1620
cagaggagga aaaacaacc aaaccccttgg ataattacga cattatggct atctgaatat    1680
tatgcaacaa ttaacgataa aaataaggca aacgagtaca taaaatgggt aattaatagg    1740
gcattaccaa ccggcttttt accagaacaa gttgatccag aaactttga gccaacttca    1800 gttacaccct tggtatggtc tcatgctgaa ttcataatag caattaataa catt          1854
```

<210> SEQ ID NO 2
<211> LENGTH: 618
<212> TYPE: PRT
<213> ORGANISM: Unknown
<220> FEATURE:
<223> OTHER INFORMATION: Protein derived from Archaea

<400> SEQUENCE: 2

```
Met Arg Val Ser Ser Ile Gly Asn Gly Arg Met Leu Ile Asn Phe Asp
1               5                   10                  15

Glu Lys Gly Arg Ile Val Asp Ile Tyr Tyr Pro Tyr Ile Gly Met Glu
                20                  25                  30

Asn Gln Thr Ser Gly Asn Pro Ile Arg Leu Ala Ile Trp Asp Lys Asp
            35                  40                  45

Lys Lys Val Ala Ser Leu Asp Glu Asp Trp Glu Thr Thr Val Leu Tyr
        50                  55                  60

Ile Asp Glu Ala Asn Met Val Glu Ile Arg Ser Asp Val Lys Glu Leu
65                  70                  75                  80

Gly Leu Ser Leu Leu Ser Tyr Asn Phe Leu Asp Ser Asp Pro Ile
                85                  90                  95

Tyr Met Ser Ile Val Lys Ile Ala Asn Asn Glu Asn Asn Ser Arg Asn
                100                 105                 110

Ile Lys Val Phe Phe Ile His Asp Ile Asn Leu Tyr Ser Asn Pro Phe
            115                 120                 125

Gly Asp Thr Ala Phe Tyr Asp Pro Leu Pro Leu Ser Ile Ile His Tyr
        130                 135                 140

Lys Ser Lys Arg Tyr Leu Ala Phe Lys Val Phe Thr Thr Val Ser Thr
145                 150                 155                 160

Leu Ser Glu Tyr Asn Ile Gly Lys Gly Asp Leu Ile Gly Asp Ile Tyr
                165                 170                 175

Asp Gly Asn Leu Gly Leu Asn Gly Ile Glu Asn Gly Asp Val Asn Ser
            180                 185                 190

Ser Met Gly Ile Glu Ile Asn Ile Asp Pro Asn Ser Tyr Leu Lys Leu
        195                 200                 205
```

-continued

```
Tyr Tyr Val Ile Val Ala Asp Arg Asn Leu Glu Gly Leu Arg Gln Lys
    210                 215                 220
Ile Arg Lys Ile Asn Phe Ala Asn Val Glu Thr Ser Phe Thr Leu Thr
225                 230                 235                 240
Tyr Met Phe Trp Arg Asn Trp Leu Lys Lys Asn Lys Leu Phe Arg Asn
                245                 250                 255
Asn Leu Met Gln Asp Ile Lys Arg Val Tyr Asp Val Ser Leu Phe Val
            260                 265                 270
Ile Arg Asn His Met Asp Val Asn Gly Ser Ile Ile Ala Ser Ser Asp
        275                 280                 285
Phe Ser Phe Val Lys Ile Tyr Gly Asp Ser Tyr Gln Tyr Cys Trp Pro
    290                 295                 300
Arg Asp Ala Ala Ile Ala Ala Tyr Ala Leu Asp Leu Ala Gly Tyr Lys
305                 310                 315                 320
Glu Leu Ala Leu Lys His Phe Gln Phe Ile Ser Asn Ile Ala Asn Ser
                325                 330                 335
Glu Gly Phe Leu Tyr His Lys Tyr Asn Pro Asn Thr Thr Leu Ala Ser
            340                 345                 350
Ser Trp His Pro Trp Tyr Tyr Lys Gly Lys Arg Ile Tyr Pro Ile Gln
        355                 360                 365
Gly Asp Glu Thr Ala Leu Glu Val Trp Ala Ile Ala Ser His Tyr Glu
370                 375                 380
Lys Tyr Glu Asp Ile Asp Glu Ile Leu Pro Leu Tyr Lys Lys Phe Val
385                 390                 395                 400
Lys Pro Ala Leu Lys Phe Met Met Ser Phe Met Glu Glu Gly Leu Pro
                405                 410                 415
Lys Pro Ser Phe Asp Leu Trp Glu Glu Arg Tyr Gly Ile His Ile Tyr
            420                 425                 430
Thr Val Ser Thr Val Tyr Gly Ala Leu Thr Lys Gly Ala Lys Leu Ala
        435                 440                 445
Tyr Asp Val Gly Asp Glu Ile Leu Ser Glu Asp Leu Ser Asp Thr Ser
    450                 455                 460
Gly Leu Leu Lys Gly Met Val Leu Lys Arg Met Thr Tyr Asn Gly Arg
465                 470                 475                 480
Phe Val Arg Arg Ile Asp Glu Glu Asn Asn Gln Asp Leu Thr Val Asp
                485                 490                 495
Ser Ser Leu Tyr Ala Pro Phe Phe Gly Leu Val Asn Ala Asn Asp
            500                 505                 510
Lys Ile Met Ile Asn Thr Ile Asn Glu Ile Glu Ser Arg Leu Thr Val
        515                 520                 525
Asn Gly Gly Ile Ile Arg Tyr Glu Asn Asp Met Tyr Gln Arg Arg Lys
530                 535                 540
Lys Gln Pro Asn Pro Trp Ile Ile Thr Thr Leu Trp Leu Ser Glu Tyr
545                 550                 555                 560
Tyr Ala Thr Ile Asn Asp Lys Asn Lys Ala Asn Glu Tyr Ile Lys Trp
                565                 570                 575
Val Ile Asn Arg Ala Leu Pro Thr Gly Phe Leu Pro Glu Gln Val Asp
            580                 585                 590
Pro Glu Thr Phe Glu Pro Thr Ser Val Thr Pro Leu Val Trp Ser His
        595                 600                 605
Ala Glu Phe Ile Ile Ala Ile Asn Asn Ile
    610                 615
```

<210> SEQ ID NO 3
<211> LENGTH: 1911
<212> TYPE: DNA
<213> ORGANISM: Unknown
<220> FEATURE:
<223> OTHER INFORMATION: DNA derived from Archaea

<400> SEQUENCE: 3

```
atggttaggt atacaccgct tggcaatggg cggttgctta tagctttga tactgattac      60
aggattgttg atttttacta ttcaaagttt gcctccgaaa atcattcgtc tggtcatcca    120
ttctactttg gtgtttccgt ggatggcaat ttcaactgga tagacagaaa tgcaatcaag    180
cacatggact actacgacca caccatggtc tctgtcgtca actacacgca taacggtatt    240
gatttcgaga cagggatat ggttgacata taaggaca tctttattag gcgggtggtt       300
gctgaaaaca agaccggtaa ggatgtaaac ctgaagatct tctttcacca gaatttctac    360
atatatggca atgacatagg ggataccgct gcttactttc ctgaataccg cggtgtgatc    420
cattataagg gagggagata ctttctcgca tccactcttg atgagagcgg taatttctgc    480
gatcaatatg ccacagggt taaggatgtg ggtgagctga agggcacatg gaaggatgcc    540
gaggacaatg aattatcaat gaacccggtg gcaataggtt cggtggattc tgtcataagg    600
cattccacga ctctgaaggc cggttcaaag ttcacgctct attatttcat catagcggga    660
agaaacatca acgatataga gagcgaatat tcaaatgtga atgtccagta cctccaaaag    720
cttctgagga gaacaacaaa ctactgggag ctctggtctt cgaaggtgac tcccagcctg    780
gattcagaca aacagcgct ttaccgcaga tcgctcttcg tgactaagag ccacgcaaac    840
gatcttgggg ccatagccgc atcctgcgac agcgatatac tgaagctgag ccatgacgga    900
tactactacg tctggcccag ggatgcctcc atggctgcat acgccttgag catatccggg    960
cacagcgaaa ccgccagacg cttctttgcc ctgatggaag attcactttc agaagaggga   1020
tacctgtacc acaaatacaa cgtcgacggc aagatcgcca gcagctggtt accgcacgtc   1080
atgaatggca aatccatata tccaatacag gaggatgaaa cagctctggt ggtctgggca   1140
ctctgggaat actttaggaa gtacaatgat atcggcttca ccgcaccgta ttatgaacgc   1200
cttataacca gggcagcaga ctttatgacc aattttgttg acaacaacgg ccttcccaag   1260
ccatcctttg atctgtggga agagcgctat ggaatccatg cctacactgt tgctacggtt   1320
tatgccgccc tgaaagcagc ttcaaacttt gcaaacgttt tcggcgatcc tgatctatcg   1380
gaaaaatacg aaaatgctgc ggaaaggatg taccatgcgt tcgatgaaag gttctattct   1440
gaggatacgg gatactatgc aagggccatc atagacggaa agccggactt caccgtggac   1500
agcgccctca cctcactggt gctctttgga atgaaggatg cggacgatcc aaaggttatt   1560
tctaccatgc agaggatatc tgaagaccta tgggtgaatg gcgttggagg catagcgcgc   1620
taccagaacg acagatacat gagggtgaag gacgatccaa gcgttcctgg aaatccctgg   1680
ataataacca cgctgtggat ggcaagatac tatatgcgtt ttggtgattt tgaaaaggcc   1740
tggaacctca tacagtgggt caagtcacac agacagaaat ccggaatatt tcggagcag    1800
ataaatccat acaatggcga accttatcc gtatctcctc tggtatggag tcattctgaa   1860
tttataatat cgcttcttga atattcggat ctaataagaa acaggtcatg a            1911
```

<210> SEQ ID NO 4
<211> LENGTH: 636
<212> TYPE: PRT
<213> ORGANISM: Unknown
<220> FEATURE:

<223> OTHER INFORMATION: Protein derived from Archaea

<400> SEQUENCE: 4

Met Val Arg Tyr Thr Pro Leu Gly Asn Gly Arg Leu Leu Ile Ala Phe
1               5                   10                  15

Asp Thr Asp Tyr Arg Ile Val Asp Phe Tyr Tyr Ser Lys Phe Ala Ser
                20                  25                  30

Glu Asn His Ser Ser Gly His Pro Phe Tyr Phe Gly Val Ser Val Asp
            35                  40                  45

Gly Asn Phe Asn Trp Ile Asp Arg Asn Ala Ile Lys His Met Asp Tyr
        50                  55                  60

Tyr Asp His Thr Met Val Ser Val Val Asn Tyr Thr His Asn Gly Ile
65                  70                  75                  80

Asp Phe Glu Asn Arg Asp Met Val Asp Ile Tyr Lys Asp Ile Phe Ile
                85                  90                  95

Arg Arg Val Val Ala Glu Asn Lys Thr Gly Lys Asp Val Asn Leu Lys
            100                 105                 110

Ile Phe Phe His Gln Asn Phe Tyr Ile Tyr Gly Asn Asp Ile Gly Asp
        115                 120                 125

Thr Ala Ala Tyr Phe Pro Glu Tyr Arg Gly Val Ile His Tyr Lys Gly
130                 135                 140

Gly Arg Tyr Phe Leu Ala Ser Thr Leu Asp Glu Ser Gly Asn Phe Cys
145                 150                 155                 160

Asp Gln Tyr Ala Thr Gly Val Lys Asp Val Gly Glu Leu Lys Gly Thr
                165                 170                 175

Trp Lys Asp Ala Glu Asp Asn Glu Leu Ser Met Asn Pro Val Ala Ile
            180                 185                 190

Gly Ser Val Asp Ser Val Ile Arg His Ser Thr Thr Leu Lys Ala Gly
        195                 200                 205

Ser Lys Phe Thr Leu Tyr Tyr Phe Ile Ile Ala Gly Arg Asn Ile Asn
210                 215                 220

Asp Ile Glu Ser Glu Tyr Ser Asn Val Asn Val Gln Tyr Leu Gln Lys
225                 230                 235                 240

Leu Leu Arg Arg Thr Thr Asn Tyr Trp Glu Leu Trp Ser Ser Lys Val
                245                 250                 255

Thr Pro Ser Leu Asp Ser Asp Thr Thr Ala Leu Tyr Arg Arg Ser Leu
            260                 265                 270

Phe Val Thr Lys Ser His Ala Asn Asp Leu Gly Ala Ile Ala Ala Ser
        275                 280                 285

Cys Asp Ser Asp Ile Leu Lys Leu Ser His Asp Gly Tyr Tyr Tyr Val
290                 295                 300

Trp Pro Arg Asp Ala Ser Met Ala Ala Tyr Ala Leu Ser Ile Ser Gly
305                 310                 315                 320

His Ser Glu Thr Ala Arg Arg Phe Phe Ala Leu Met Glu Asp Ser Leu
                325                 330                 335

Ser Glu Glu Gly Tyr Leu Tyr His Lys Tyr Asn Val Asp Gly Lys Ile
            340                 345                 350

Ala Ser Ser Trp Leu Pro His Val Met Asn Gly Lys Ser Ile Tyr Pro
        355                 360                 365

Ile Gln Glu Asp Glu Thr Ala Leu Val Val Trp Ala Leu Trp Glu Tyr
370                 375                 380

Phe Arg Lys Tyr Asn Asp Ile Gly Phe Thr Ala Pro Tyr Tyr Glu Arg
385                 390                 395                 400

Leu Ile Thr Arg Ala Ala Asp Phe Met Thr Asn Phe Val Asp Asn Asn
                405                 410                 415

Gly Leu Pro Lys Pro Ser Phe Asp Leu Trp Glu Glu Arg Tyr Gly Ile
            420                 425                 430

His Ala Tyr Thr Val Ala Thr Val Tyr Ala Ala Leu Lys Ala Ala Ser
        435                 440                 445

Asn Phe Ala Asn Val Phe Gly Asp Pro Asp Leu Ser Glu Lys Tyr Glu
    450                 455                 460

Asn Ala Ala Glu Arg Met Tyr His Ala Phe Asp Glu Arg Phe Tyr Ser
465                 470                 475                 480

Glu Asp Thr Gly Tyr Tyr Ala Arg Ala Ile Ile Asp Gly Lys Pro Asp
                485                 490                 495

Phe Thr Val Asp Ser Ala Leu Thr Ser Leu Val Leu Phe Gly Met Lys
            500                 505                 510

Asp Ala Asp Asp Pro Lys Val Ile Ser Thr Met Gln Arg Ile Ser Glu
        515                 520                 525

Asp Leu Trp Val Asn Gly Val Gly Gly Ile Ala Arg Tyr Gln Asn Asp
    530                 535                 540

Arg Tyr Met Arg Val Lys Asp Asp Pro Ser Val Pro Gly Asn Pro Trp
545                 550                 555                 560

Ile Ile Thr Thr Leu Trp Met Ala Arg Tyr Tyr Met Arg Phe Gly Asp
                565                 570                 575

Phe Glu Lys Ala Trp Asn Leu Ile Gln Trp Val Lys Ser His Arg Gln
            580                 585                 590

Lys Ser Gly Ile Phe Ser Glu Gln Ile Asn Pro Tyr Asn Gly Glu Pro
        595                 600                 605

Leu Ser Val Ser Pro Leu Val Trp Ser His Ser Glu Phe Ile Ile Ser
    610                 615                 620

Leu Leu Glu Tyr Ser Asp Leu Ile Arg Asn Arg Ser
625                 630                 635

<210> SEQ ID NO 5
<211> LENGTH: 1854
<212> TYPE: DNA
<213> ORGANISM: Unknown
<220> FEATURE:
<223> OTHER INFORMATION: DNA derived from Archaea

<400> SEQUENCE: 5
atgatttata tgggcggaat aattggaaat aacaacctat tagtaaaaat cggagattat      60
ggggaaatta gttatgtttt ctatcctcat gtgggttatg aaacccattt cttcgattct     120
gcattggcag tgtatgataa aaaagtaaaa tggcattggg atgatgattg ggacatctct     180
caaaaatata ttgaagaaac aaatatattc aaaactatac tggaagacga taaaataata     240
ttgacaatta agattttgt tccagtttcg cacaatgtaa tcattagaag gttgcatata     300
aaaaataaac tcgataaaaa attgaatttt aagctatttt tttatgaaaa tttaaggatt     360
ggggagtatc ctacagaaaa tgccgtaaga ttttagagg atgagggatg tatcgttaaa     420
tataacgaaa aatatgtttt ctgcattgga agtaataaaa agatagattc gttccagtgt     480
ggaaacagat acagcaaaaa cagtgcatac gtagatattg aaaacggatt gttgatggaa     540 cataagaaa gccatggact gatgacagat agtgcaatat cgtggaatat agagattgat     600
aaaggaaaga gcttagcgtt taatatctat atacttctac aaaaatttga tggagattta     660
tcaataataa ccgagcagtt aaagattata atgaacaata ctgtacatat caaagacctt     720

-continued

```
tcaatgaact attggaaaaa tagcattgga aatataaaag aacatatcca tcctcaattt    780
cattcagata aagaaatatg tcctatagct aaaagggctt taatggttct tctaatgctt    840
tgtgataaag atggggggat tatagccgct ccttcactac atccagacta taggtatgtt    900
tgggggaggg atgggcctta tatagcaatt gcattagatt tatttggaat tagaggaatt    960
cccgatagat tctttgaatt catgtctaaa attcaaaatg atgatggttc atggctacaa   1020
aactactaca caaatggaaa accgagatta acagcgatgc agattgacca aattggctct   1080
atactgtggg ctatggatgt gcattataga ttaactggaa atagaaagtt tgttgagagg   1140
tattggaata ctatagaaaa agctggaaat tatctaactt ctgccgcttt aaacttcaca   1200
ccatgctttg atttatggga agaaaagttt ggagttttttg catatactat gggagcaatc   1260
tatgcgggat aaaagctgc ttatagtatg agtaaagctg ttgatatgag ggataaggtt   1320
aaacattggg aaaaagctat tgaattttttg aaaaaggaag ttccaaggag atttttattta   1380
gaagatgagg aaagatttgc taaatcaata aatccattgg ataaggagat agacgctagc   1440
atattgggat tgagctatcc atttaactta attgatgttg atgatgaaag gatgataaaa   1500
acagctgagg ctattgaaaa tgcatttaac tacaaagttg gtgggattgg gagatatcct   1560
aatgatgttt attttggagg gaacccatgg attataacga cattgtggat ttctttatat   1620
tatagaaggt tatccaaggt tttaaaagag aaaaataaaa atgatatggc agagaaatat   1680
ttaaaaaaat ctaaaaaatt gtttgattgg gcagttaaat acagctttaa cggtttgttt   1740
ccagagcaga tacataagga cctcggcatt ccaatgtctg caatgccttt gggctggagc   1800
aatgcaatgt ttttaatcta cctatataag gatgacaatg tcataattcc ataa         1854
```

<210> SEQ ID NO 6
<211> LENGTH: 617
<212> TYPE: PRT
<213> ORGANISM: Unknown
<220> FEATURE:
<223> OTHER INFORMATION: Protein derived from Archaea

<400> SEQUENCE: 6

```
Met Ile Tyr Met Gly Gly Ile Ile Gly Asn Asn Asn Leu Leu Val Lys
1               5                   10                  15

Ile Gly Asp Tyr Gly Glu Ile Ser Tyr Val Phe Tyr Pro His Val Gly
            20                  25                  30

Tyr Glu Thr His Phe Phe Asp Ser Ala Leu Ala Val Tyr Asp Lys Lys
        35                  40                  45

Val Lys Trp His Trp Asp Asp Trp Asp Ile Ser Gln Lys Tyr Ile
    50                  55                  60

Glu Glu Thr Asn Ile Phe Lys Thr Ile Leu Glu Asp Lys Ile Ile
65                  70                  75                  80

Leu Thr Ile Lys Asp Phe Val Pro Val Ser His Asn Val Ile Ile Arg
                85                  90                  95

Arg Leu His Ile Lys Asn Lys Leu Asp Lys Leu Asn Phe Lys Leu
            100                 105                 110

Phe Phe Tyr Glu Asn Leu Arg Ile Gly Glu Tyr Pro Thr Glu Asn Ala
        115                 120                 125

Val Arg Phe Leu Glu Asp Gly Cys Ile Val Lys Tyr Asn Glu Lys
    130                 135                 140

Tyr Val Phe Cys Ile Gly Ser Asn Lys Lys Ile Asp Ser Phe Gln Cys
145                 150                 155                 160

Gly Asn Arg Tyr Ser Lys Asn Ser Ala Tyr Val Asp Ile Glu Asn Gly
```

```
            165                 170                 175
Leu Leu Met Glu His Lys Glu Ser His Gly Leu Met Thr Asp Ser Ala
                180                 185                 190

Ile Ser Trp Asn Ile Glu Ile Asp Lys Gly Lys Ser Leu Ala Phe Asn
                195                 200                 205

Ile Tyr Ile Leu Leu Gln Lys Phe Asp Gly Asp Leu Ser Ile Ile Thr
210                 215                 220

Glu Gln Leu Lys Ile Ile Met Asn Asn Thr Val His Ile Lys Asp Leu
225                 230                 235                 240

Ser Met Asn Tyr Trp Lys Asn Ser Ile Gly Asn Ile Lys Glu His Ile
                245                 250                 255

His Pro Gln Phe His Ser Asp Lys Glu Ile Cys Pro Ile Ala Lys Arg
                260                 265                 270

Ala Leu Met Val Leu Leu Met Leu Cys Asp Lys Asp Gly Gly Ile Ile
                275                 280                 285

Ala Ala Pro Ser Leu His Pro Asp Tyr Arg Tyr Val Trp Gly Arg Asp
                290                 295                 300

Gly Ala Tyr Ile Ala Ile Ala Leu Asp Leu Phe Gly Ile Arg Gly Ile
305                 310                 315                 320

Pro Asp Arg Phe Phe Glu Phe Met Ser Lys Ile Gln Asn Asp Asp Gly
                325                 330                 335

Ser Trp Leu Gln Asn Tyr Tyr Thr Asn Gly Lys Pro Arg Leu Thr Ala
                340                 345                 350

Met Gln Ile Asp Gln Ile Gly Ser Ile Leu Trp Ala Met Asp Val His
                355                 360                 365

Tyr Arg Leu Thr Gly Asn Arg Lys Phe Val Glu Arg Tyr Trp Asn Thr
370                 375                 380

Ile Glu Lys Ala Gly Asn Tyr Leu Thr Ser Ala Ala Leu Asn Phe Thr
385                 390                 395                 400

Pro Cys Phe Asp Leu Trp Glu Glu Lys Phe Gly Val Phe Ala Tyr Thr
                405                 410                 415

Met Gly Ala Ile Tyr Ala Gly Leu Lys Ala Ala Tyr Ser Met Ser Lys
                420                 425                 430

Ala Val Asp Met Arg Asp Lys Val Lys His Trp Glu Lys Ala Ile Glu
                435                 440                 445

Phe Leu Lys Lys Glu Val Pro Arg Arg Phe Tyr Leu Glu Asp Glu Glu
                450                 455                 460

Arg Phe Ala Lys Ser Ile Asn Pro Leu Asp Lys Glu Ile Asp Ala Ser
465                 470                 475                 480

Ile Leu Gly Leu Ser Tyr Pro Phe Asn Leu Ile Asp Val Asp Asp Glu
                485                 490                 495

Arg Met Ile Lys Thr Ala Glu Ala Ile Glu Asn Ala Phe Asn Tyr Lys
                500                 505                 510

Val Gly Gly Ile Gly Arg Tyr Pro Asn Asp Val Tyr Phe Gly Gly Asn
                515                 520                 525

Pro Trp Ile Ile Thr Thr Leu Trp Ile Ser Leu Tyr Tyr Arg Arg Leu
                530                 535                 540

Ser Lys Val Leu Lys Glu Lys Asn Lys Asn Asp Met Ala Glu Lys Tyr
545                 550                 555                 560

Leu Lys Lys Ser Lys Lys Leu Phe Asp Trp Ala Val Lys Tyr Ser Phe
                565                 570                 575

Asn Gly Leu Phe Pro Glu Gln Ile His Lys Asp Leu Gly Ile Pro Met
                580                 585                 590
```

Ser Ala Met Pro Leu Gly Trp Ser Asn Ala Met Phe Leu Ile Tyr Leu
        595                 600                 605

Tyr Lys Asp Asp Asn Val Ile Ile Pro
        610                 615

<210> SEQ ID NO 7
<211> LENGTH: 1866
<212> TYPE: DNA
<213> ORGANISM: Unknown
<220> FEATURE:
<223> OTHER INFORMATION: DNA derived from Archaea

<400> SEQUENCE: 7

| | |
|---|---|
| atggcaggga ttattggaaa tggaaaccta ctggcaaaaa ttgatgactt ggggtctata | 60 |
| gaatatatat ttttcccaca tttgggttac gaaacacata ttctcgatac atcatttgct | 120 |
| atatactaca acaacaaaat aaaatggcat tgggatcata gttgggacgt tagtcagaac | 180 |
| tatctcaaag attccaacat attaaaaaca acttatgaaa atgatgactt cttaatatat | 240 |
| tctaaggatt gtgtatccat atctcacaac cttattgtta acaactttc tataataaac | 300 |
| aagaccaatt cagaaaagga cataaaatta ttttttttatg aaaatttgag ataggtgaa | 360 |
| acgccgagta aaagcactgt aaaatttgtt aaagaaaaaa actgcctaat taaacatgac | 420 |
| aaaaattata ttttctgtat tggcagtaat aaaaaagtat cctcttacca atgtgggatt | 480 |
| aaatactctg agagtagtgc tttaagggac attgaaaatg gagtactgaa agagcagagt | 540 |
| tccgccacag gattaatcac agacagtgcc ctttgctggg aattcaaaat caaacctaac | 600 |
| caaaaataca ctctttcaat actcatactt cctgaaaagt atgatggtga ttataataaa | 660 |
| accctaaact taatggatac tctacacatg gtaaaagaca acctcaaaga cctatataac | 720 |
| ctcacaagaa atttctggaa aagtagagta gatagcatgg taaataagtg gggaatctta | 780 |
| aagttggaag aatataaaga atgcatagat atatgcaaaa gatctctact aaccctatta | 840 |
| cttctctgcg attataaggg gggaataatt gcttctcctt ctttacatcc agattatagg | 900 |
| tatgtctggt gtagggatgc agggtatatg gcagttgcgt tggatttgtg tgggcagcat | 960 |
| gaaatgagtg agaaatactt tgagtggtgc aagacaacac aaaacagtga cggttcttgg | 1020 |
| gttcaaaatt actatgtgga ggggtatcca agattcacag ccatccaaat agatcaggtg | 1080 |
| ggtactacca tttgggcact tcttgtgcac tatagaataa ctggagacaa acatttttta | 1140 |
| aaaagaaatt gggaaatggt caaaaagca ggggactatt tgagcagagc tgctgaccaa | 1200 |
| ttaatacccc gctatgactt atgggaagaa agtttgggg tctttgcata taccctcgga | 1260 |
| gcaatatatg gggggttgaa atcaggttat ttaattggaa agaacttga caagaagaa | 1320 |
| gaaatacagc attggaaaaa aagcatgaac ttccttaaaa atgaagtggt aaatagactc | 1380 |
| tacttaaaaa atgagaagag gtttgcaaaa tcattaaaac cattagataa aaccatagat | 1440 |
| acgagtattt tagggttaag tttcccctat ggacttgtgt cagtcgatga cccaagaata | 1500 |
| atatcaactg caaatcagat tgaaaaagcc ttcaactaca aagttggtgg tgttggtaga | 1560 |
| tatccagagg acatatactt tggaggaaat ccttggataa taacaaccct atggctctat | 1620 |
| atgtattata aaaagttagt tgatacatta tcaaaaaaag gaaaattcca agagtccata | 1680 |
| attgataatt acaataaaaa atgttacaac ttgcttaaat ggattctaaa acatcaattc | 1740 |
| aatggtatgt ttccagaaca agtccataaa gatttgggaa ttccaatatc tgcaattccc | 1800 |
| cttggctggt cacatgccat ggttataatc gctattcatg gtgattacga catcctaata | 1860 |

-continued ccctaa 1866

<210> SEQ ID NO 8
<211> LENGTH: 621
<212> TYPE: PRT
<213> ORGANISM: Unknown
<220> FEATURE:
<223> OTHER INFORMATION: Protein derived from Archaea

<400> SEQUENCE: 8

```
Met Ala Gly Ile Ile Gly Asn Gly Asn Leu Leu Ala Lys Ile Asp Asp
1               5                   10                  15

Leu Gly Ser Ile Glu Tyr Ile Phe Phe Pro His Leu Gly Tyr Glu Thr
            20                  25                  30

His Ile Leu Asp Thr Ser Phe Ala Ile Tyr Tyr Asn Asn Lys Ile Lys
        35                  40                  45

Trp His Trp Asp His Ser Trp Asp Val Ser Gln Asn Tyr Leu Lys Asp
    50                  55                  60

Ser Asn Ile Leu Lys Thr Thr Tyr Glu Asn Asp Asp Phe Leu Ile Tyr
65                  70                  75                  80

Ser Lys Asp Cys Val Ser Ile Ser His Asn Leu Ile Val Lys Gln Leu
                85                  90                  95

Ser Ile Ile Asn Lys Thr Asn Ser Glu Lys Asp Ile Lys Leu Phe Phe
            100                 105                 110

Tyr Glu Asn Leu Arg Ile Gly Glu Thr Pro Ser Lys Ser Thr Val Lys
        115                 120                 125

Phe Val Lys Glu Lys Asn Cys Leu Ile Lys His Asp Lys Asn Tyr Ile
    130                 135                 140

Phe Cys Ile Gly Ser Asn Lys Lys Val Ser Ser Tyr Gln Cys Gly Ile
145                 150                 155                 160

Lys Tyr Ser Glu Ser Ser Ala Leu Arg Asp Ile Glu Asn Gly Val Leu
                165                 170                 175

Lys Glu Gln Ser Ser Ala Thr Gly Leu Ile Thr Asp Ser Ala Leu Cys
            180                 185                 190

Trp Glu Phe Lys Ile Lys Pro Asn Gln Lys Tyr Thr Leu Ser Ile Leu
        195                 200                 205

Ile Leu Pro Glu Lys Tyr Asp Gly Asp Tyr Asn Lys Thr Leu Asn Leu
    210                 215                 220

Met Asp Thr Leu His Met Val Lys Asp Asn Leu Lys Asp Leu Tyr Asn
225                 230                 235                 240

Leu Thr Arg Asn Phe Trp Lys Ser Arg Val Asp Ser Met Val Asn Lys
                245                 250                 255

Trp Gly Ile Leu Lys Leu Glu Glu Tyr Lys Glu Cys Ile Asp Ile Cys
            260                 265                 270

Lys Arg Ser Leu Leu Thr Leu Leu Leu Cys Asp Tyr Lys Gly Gly
        275                 280                 285

Ile Ile Ala Ser Pro Ser Leu His Pro Asp Tyr Arg Tyr Val Trp Cys
    290                 295                 300

Arg Asp Ala Gly Tyr Met Ala Val Ala Leu Asp Leu Cys Gly Gln His
305                 310                 315                 320

Glu Met Ser Glu Lys Tyr Phe Glu Trp Cys Lys Thr Thr Gln Asn Ser
                325                 330                 335

Asp Gly Ser Trp Val Gln Asn Tyr Tyr Val Glu Gly Tyr Pro Arg Phe
            340                 345                 350

Thr Ala Ile Gln Ile Asp Gln Val Gly Thr Thr Ile Trp Ala Leu Leu
```

```
                355                 360                 365
Val His Tyr Arg Ile Thr Gly Asp Lys His Phe Leu Lys Arg Asn Trp
        370                 375                 380

Glu Met Val Lys Lys Ala Gly Asp Tyr Leu Ser Arg Ala Ala Asp Gln
385                 390                 395                 400

Leu Ile Pro Cys Tyr Asp Leu Trp Glu Lys Phe Gly Val Phe Ala
            405                 410                 415

Tyr Thr Leu Gly Ala Ile Tyr Gly Leu Lys Ser Gly Tyr Leu Ile
        420                 425                 430

Gly Lys Glu Leu Asp Lys Glu Glu Ile Gln His Trp Lys Lys Ser
        435                 440                 445

Met Asn Phe Leu Lys Asn Glu Val Val Asn Arg Leu Tyr Leu Lys Asn
        450                 455                 460

Glu Lys Arg Phe Ala Lys Ser Leu Lys Pro Leu Asp Lys Thr Ile Asp
465                 470                 475                 480

Thr Ser Ile Leu Gly Leu Ser Phe Pro Tyr Gly Leu Val Ser Val Asp
                485                 490                 495

Asp Pro Arg Ile Ile Ser Thr Ala Asn Gln Ile Glu Lys Ala Phe Asn
            500                 505                 510

Tyr Lys Val Gly Gly Val Gly Arg Tyr Pro Glu Asp Ile Tyr Phe Gly
        515                 520                 525

Gly Asn Pro Trp Ile Ile Thr Thr Leu Trp Leu Tyr Met Tyr Tyr Lys
        530                 535                 540

Lys Leu Val Asp Thr Leu Ser Lys Lys Gly Lys Phe Gln Glu Ser Ile
545                 550                 555                 560

Ile Asp Asn Tyr Asn Lys Lys Cys Tyr Asn Leu Leu Lys Trp Ile Leu
                565                 570                 575

Lys His Gln Phe Asn Gly Met Phe Pro Glu Gln Val His Lys Asp Leu
            580                 585                 590

Gly Ile Pro Ile Ser Ala Ile Pro Leu Gly Trp Ser His Ala Met Val
        595                 600                 605

Ile Ile Ala Ile His Gly Asp Tyr Asp Ile Leu Ile Pro
610                 615                 620

<210> SEQ ID NO 9
<211> LENGTH: 1848
<212> TYPE: DNA
<213> ORGANISM: Unknown
<220> FEATURE:
<223> OTHER INFORMATION: DNA derived from Archaea

<400> SEQUENCE: 9
atgatttata tgggtggaat cgttggaaac aatagtttat tagccaaaat tggagattat      60
ggggaaattg ataccttttt ttatccccaa gttggttatg aaactcattt ctttgactct     120
gcattggcag tttatgataa aaaagtaaag tggcattggg atgatgattg ggatataacc     180 caaaataca ttgaggaaac gaacatattt aaaactatct tagaagatga aagattata      240 ttaaccatta aagattttgt gccagtatct cacaacgtgc ttataagaag agtgtatata     300
aaaaataaac tcgataaaaa attaaatttt aagctctttt tttacgaaaa tttgagaatt     360
ggtgaaaacc caataacaaa tacagttaaa ttcttagaag atggttgtat cgttaaatat     420
aatggaaaat atatttttg cattggaagt gataaaagaa tagattcatt tcagtgtgga     480
aatagataca gtaaaacaag tgcttacata gacatagaaa atgggatatt gaaggagcat     540
aaagagagtt ctggattatt aaccgatagt gcaatatcat ggaatataaa gattgatgaa     600
```

```
aaaagaagtt tggcattcaa catctacata cttccacaaa gattcgatgg agattttca      660 ataataactg aacaactaaa gattataatg aataacagtg aaaacattaa aaatctctca     720
atgaattatt ggaaacatat tataggggag ataaatagat ttatacatcc tgagcttagg     780
caaaataata gatttattc tataactaaa agggctttaa tgacactttt aatgttatgt     840
gataaggaag gagggattat agcggctcca tctctacatc cagattatag atacgtgtgg    900
ggaagagatg gaagttatat ctcaattgct tggacttat ttggcataag gaacattcca    960
gacagatttt ttgaattcat gtctaagata caaaatgcag acggttcatg gctacaaaat   1020
tattatgtta atggaaaacc acgattaact gcaatacaga ctgaccaaat tggttccata    1080
ttatgggcaa tggatgtgca ttacagatta actggggata gaaagttcgt tgagagatac   1140
tggaacacta tagagaaagc tgctaattat ttaaggttgg tagctttaaa ctttactcca    1200
tgcttcgatt tgtgggaaga gaggtttgga gtatttgctt atacaatggg agctacttac    1260
gctggattga atgtgcata cagcatgagt aaggcagtga ataaaaggga taaagttaag    1320
gattggggaa aaccataga attttaaaa catgaggttc caagagatt ttatttggaa     1380 gatgaggaaa gatttgctaa atcaataaat cctttagaca agacgataga cacaagcata    1440
ttgggtttaa gttacccttt caatttgatt gatgttgatg atgagagaat gataaaaaca   1500
gccgaagcaa ttgaaaaagc tttcaaatat aaggttggag ggattgggag atatccagaa   1560
gacatttact ttggaggcaa tccatggatt ataaccacat tatggctttc tttgtattat   1620
agaaggttat acaaggtttt aaaagaaaaa gatgataatg gggcagatat ttatctacaa    1680
aaatctaaga agttgtttaa ttgggtgatg aaatacagct ttgatgggct gtttccagag    1740
caaattcata aagaattagg tgtgccaatg tccgctatgc ctttaggctg gagcaatgca    1800
atgttcctca tttatgtgta tgagaatgat aaggtcataa taccataa                1848
```

<210> SEQ ID NO 10
<211> LENGTH: 615
<212> TYPE: PRT
<213> ORGANISM: Unknown
<220> FEATURE:
<223> OTHER INFORMATION: Protein derived from Archaea

<400> SEQUENCE: 10

```
Met Ile Tyr Met Gly Gly Ile Val Gly Asn Asn Ser Leu Leu Ala Lys
1               5                   10                  15

Ile Gly Asp Tyr Gly Glu Ile Glu Tyr Leu Phe Tyr Pro Gln Val Gly
            20                  25                  30

Tyr Glu Thr His Phe Phe Asp Ser Ala Leu Ala Val Tyr Asp Lys Lys
        35                  40                  45

Val Lys Trp His Trp Asp Asp Asp Trp Asp Ile Thr Gln Lys Tyr Ile
    50                  55                  60

Glu Glu Thr Asn Ile Phe Lys Thr Ile Leu Glu Asp Asp Lys Ile Ile
65                  70                  75                  80

Leu Thr Ile Lys Asp Phe Val Pro Val Ser His Asn Val Leu Ile Arg
                85                  90                  95

Arg Val Tyr Ile Lys Asn Lys Leu Asp Lys Leu Asn Phe Lys Leu
            100                 105                 110

Phe Phe Tyr Glu Asn Leu Arg Ile Gly Glu Asn Pro Ile Thr Asn Thr
        115                 120                 125

Val Lys Phe Leu Glu Asp Gly Cys Ile Val Lys Tyr Asn Gly Lys Tyr
    130                 135                 140
```

```
Ile Phe Cys Ile Gly Ser Asp Lys Arg Ile Asp Ser Phe Gln Cys Gly
145                 150                 155                 160

Asn Arg Tyr Ser Lys Thr Ser Ala Tyr Ile Asp Ile Glu Asn Gly Ile
            165                 170                 175

Leu Lys Glu His Lys Glu Ser Ser Gly Leu Leu Thr Asp Ser Ala Ile
        180                 185                 190

Ser Trp Asn Ile Lys Ile Asp Glu Lys Arg Ser Leu Ala Phe Asn Ile
        195                 200                 205

Tyr Ile Leu Pro Gln Arg Phe Asp Gly Asp Phe Ser Ile Ile Thr Glu
210                 215                 220

Gln Leu Lys Ile Ile Met Asn Asn Ser Glu Asn Ile Lys Asn Leu Ser
225                 230                 235                 240

Met Asn Tyr Trp Lys His Ile Ile Gly Glu Ile Asn Arg Phe Ile His
            245                 250                 255

Pro Glu Leu Arg Gln Asn Asn Lys Ile Tyr Ser Ile Thr Lys Arg Ala
            260                 265                 270

Leu Met Thr Leu Leu Met Leu Cys Asp Lys Glu Gly Ile Ile Ala
        275                 280                 285

Ala Pro Ser Leu His Pro Asp Tyr Arg Tyr Val Trp Gly Arg Asp Gly
290                 295                 300

Ser Tyr Ile Ser Ile Ala Leu Asp Leu Phe Gly Ile Arg Asn Ile Pro
305                 310                 315                 320

Asp Arg Phe Phe Glu Phe Met Ser Lys Ile Gln Asn Ala Asp Gly Ser
            325                 330                 335

Trp Leu Gln Asn Tyr Tyr Val Asn Gly Lys Pro Arg Leu Thr Ala Ile
            340                 345                 350

Gln Thr Asp Gln Ile Gly Ser Ile Leu Trp Ala Met Asp Val His Tyr
        355                 360                 365

Arg Leu Thr Gly Asp Arg Lys Phe Val Glu Arg Tyr Trp Asn Thr Ile
370                 375                 380

Glu Lys Ala Ala Asn Tyr Leu Arg Leu Val Ala Leu Asn Phe Thr Pro
385                 390                 395                 400

Cys Phe Asp Leu Trp Glu Glu Arg Phe Gly Val Phe Ala Tyr Thr Met
            405                 410                 415

Gly Ala Thr Tyr Ala Gly Leu Lys Cys Ala Tyr Ser Met Ser Lys Ala
            420                 425                 430

Val Asn Lys Arg Asp Lys Val Lys Asp Trp Gly Lys Thr Ile Glu Phe
        435                 440                 445

Leu Lys His Glu Val Pro Lys Arg Phe Tyr Leu Glu Asp Glu Arg
    450                 455                 460

Phe Ala Lys Ser Ile Asn Pro Leu Asp Lys Thr Ile Asp Thr Ser Ile
465                 470                 475                 480

Leu Gly Leu Ser Tyr Pro Phe Asn Leu Ile Asp Val Asp Asp Glu Arg
            485                 490                 495

Met Ile Lys Thr Ala Glu Ala Ile Glu Lys Ala Phe Lys Tyr Lys Val
        500                 505                 510

Gly Gly Ile Gly Arg Tyr Pro Glu Asp Ile Tyr Phe Gly Gly Asn Pro
        515                 520                 525

Trp Ile Ile Thr Thr Leu Trp Leu Ser Leu Tyr Tyr Arg Arg Leu Tyr
        530                 535                 540

Lys Val Leu Lys Glu Lys Asp Asp Asn Gly Ala Asp Ile Tyr Leu Gln
545                 550                 555                 560
```

```
Lys Ser Lys Lys Leu Phe Asn Trp Val Met Lys Tyr Ser Phe Asp Gly
            565                 570                 575

Leu Phe Pro Glu Gln Ile His Lys Glu Leu Gly Val Pro Met Ser Ala
        580                 585                 590

Met Pro Leu Gly Trp Ser Asn Ala Met Phe Leu Ile Tyr Val Tyr Glu
            595                 600                 605

Asn Asp Lys Val Ile Ile Pro
        610                 615

<210> SEQ ID NO 11
<211> LENGTH: 2034
<212> TYPE: DNA
<213> ORGANISM: Unknown
<220> FEATURE:
<223> OTHER INFORMATION: DNA derived from Archaea

<400> SEQUENCE: 11
gtggttagca tggtaggaat tattgggaat gggaaaatcc tcgcaaagat tgatgactca      60
ggctctttgg aatacatatt ttttccacat ttggggcatg agaaacatat ttttgattca     120
tcatttgcca tattttatga taataagttg aaatggaatt gggacaattc ctgggatatt     180
aatcagaact atttaaaaga tacaaacata ttgaaaacat catatgaaaa cgaggatttt     240
ctaatagaat caaggactac cgtgcctata tcccataact cgataattaa gcaaatatca     300
atattaaaca aatccagcga aaaaagaat ttaaaactgt tttttatga aatttaaga       360 atgggagaaa ttcctgaagt aagtactgta agtatagaa agaacaggga gtgcattatt      420
aaatacgata agaattatgt tttttgtatc ggcagtaata aaaaagtatc ttcataccaa     480
tgtggtgtta ggtcatccga gagtagtgcc ctaaatgatc tcaaaaatgg tattttaaag    540
gaatacgata gtgctgaagg cctaatcaca gatagcgcac tgggttggga ccttgagttg    600
agtccaaatc aggaacagaa agtctcaata tttatatttg cagataagta tggtggggat    660
tataccaaaa ttatgaattt attggataca ctaaatatag ttataaccaa tcacgcagac    720
atatatgatc ttacaatggc atactggaag aacatgattg aaaccactgc gaatagtcta    780
tgcaattcaa atcaagtctt taagatttta acacatataa aagacgacgc aaatatttca    840
aatttaaaaa gaataaaaca gtatgaagct atttgtaaaa gatccctatt aaccatttta    900
ctcctttgtg atcataatgg tggaataatt gcatcaccat cactctatcc agattataga    960
tatgtatggt gtagggacgc aggttatatg gccgtcgcac ttgacctatg tggtcagcat   1020
ggaataagcg aaaatacttt gaatggtgc aaaaaaacac aaaatagtga tggctcatgg   1080
gttcaaaact actacgtaga aggaaatcca aggcttacgg caattcaaat tgaccaagtt   1140
ggtactacaa tctgggccgc acttgtacat tatagaataa ctagggacaa attatttctg   1200
aacagatatt gggaaatgat taaaaaagca ggggattatt taagtagtgt tgccaatcca   1260
ccatcaccaa gctatgattt atgggaagaa aaatatggtg tattcgcata cacacttggc   1320
gcaatttatg gaggattaaa atctgcctac aacatttgta aaatactggg caaggaagaa   1380
cacgatatcc aaaattggaa agagagcatg gacttcctta aaaacgaaat ggtagatagg   1440 ctttattttaa aagatgaaaa tagatttgca aaatcattgg atccattgga caaagctcta   1500
gatgctagta ttttagggct cagttttcca tataatttgg tacctgttga tgaccctaga   1560
atgattagca ccgccaacca aattgaaaat gcgtttaagt ataaggttgg aggtatagga   1620
aggtaccctg aagatgttta tttcggaggg aatccttgga taataaccac aatatggctc   1680
catatgtact atgaaaactt gattaaatca ttatctaaac atggtaaaaa tgccatacat   1740
```

-continued

```
tctgatcaaa tccctgattc ttcaggggac cttaaggatt ttgtctcaat tatagggtcc    1800
attgaaaacc atggtgaaaa gtcagatgaa acccctagtt ccgacacact ccttacttat    1860
gcccaaaaat gtaacaattt gtttgattgg actttaaagt ataactttaa tgaactattt    1920
ccagaacagg ttcacaaaga tcttggagct ccgatatctg caattccact tgggtggtca    1980
catgcaatgg tcataattgc catccatggt aactttgata tattaatacc ttaa          2034
```

<210> SEQ ID NO 12
<211> LENGTH: 677
<212> TYPE: PRT
<213> ORGANISM: Unknown
<220> FEATURE:
<223> OTHER INFORMATION: Protein derived from Archaea

<400> SEQUENCE: 12

```
Met Val Ser Met Val Gly Ile Ile Gly Asn Gly Lys Ile Leu Ala Lys
1               5                   10                  15

Ile Asp Asp Ser Gly Ser Leu Glu Tyr Ile Phe Phe Pro His Leu Gly
            20                  25                  30

His Glu Lys His Ile Phe Asp Ser Ser Phe Ala Ile Phe Tyr Asp Asn
        35                  40                  45

Lys Leu Lys Trp Asn Trp Asp Asn Ser Trp Asp Ile Asn Gln Asn Tyr
    50                  55                  60

Leu Lys Asp Thr Asn Ile Leu Lys Thr Ser Tyr Glu Asn Glu Asp Phe
65                  70                  75                  80

Leu Ile Glu Ser Lys Asp Tyr Val Pro Ile Ser His Asn Ser Ile Ile
                85                  90                  95

Lys Gln Ile Ser Ile Leu Asn Lys Ser Ser Glu Lys Lys Asn Leu Lys
            100                 105                 110

Leu Phe Phe Tyr Glu Asn Leu Arg Met Gly Glu Ile Pro Glu Val Ser
        115                 120                 125

Thr Val Lys Tyr Arg Lys Asn Arg Glu Cys Ile Ile Lys Tyr Asp Lys
    130                 135                 140

Asn Tyr Val Phe Cys Ile Gly Ser Asn Lys Lys Val Ser Ser Tyr Gln
145                 150                 155                 160

Cys Gly Val Arg Ser Ser Glu Ser Ser Ala Leu Asn Asp Leu Lys Asn
                165                 170                 175

Gly Ile Leu Lys Glu Tyr Asp Ser Ala Glu Gly Leu Ile Thr Asp Ser
            180                 185                 190

Ala Leu Gly Trp Asp Leu Glu Leu Ser Pro Asn Gln Glu Gln Lys Val
        195                 200                 205

Ser Ile Phe Ile Phe Ala Asp Lys Tyr Gly Gly Asp Tyr Thr Lys Ile
    210                 215                 220

Met Asn Leu Leu Asp Thr Leu Asn Ile Val Ile Thr Asn His Ala Asp
225                 230                 235                 240

Ile Tyr Asp Leu Thr Met Ala Tyr Trp Lys Asn Met Ile Glu Thr Thr
                245                 250                 255

Ala Asn Ser Leu Cys Asn Ser Asn Gln Val Phe Lys Asp Leu Thr His
            260                 265                 270

Ile Lys Asp Asp Ala Asn Ile Ser Asn Leu Lys Arg Ile Lys Gln Tyr
        275                 280                 285

Glu Ala Ile Cys Lys Arg Ser Leu Leu Thr Ile Leu Leu Cys Asp
    290                 295                 300

His Asn Gly Gly Ile Ile Ala Ser Pro Ser Leu Tyr Pro Asp Tyr Arg
```

```
            305                 310                 315                 320
Tyr Val Trp Cys Arg Asp Ala Gly Tyr Met Ala Val Ala Leu Asp Leu
                325                 330                 335

Cys Gly Gln His Gly Ile Ser Glu Lys Tyr Phe Glu Trp Cys Lys Lys
                340                 345                 350

Thr Gln Asn Ser Asp Gly Ser Trp Val Gln Asn Tyr Val Glu Gly
                355                 360                 365

Asn Pro Arg Leu Thr Ala Ile Gln Ile Asp Gln Val Gly Thr Thr Ile
370                 375                 380

Trp Ala Ala Leu Val His Tyr Arg Ile Thr Arg Asp Lys Leu Phe Leu
385                 390                 395                 400

Asn Arg Tyr Trp Glu Met Ile Lys Lys Ala Gly Asp Tyr Leu Ser Ser
                405                 410                 415

Val Ala Asn Pro Pro Ser Pro Ser Tyr Asp Leu Trp Glu Glu Lys Tyr
                420                 425                 430

Gly Val Phe Ala Tyr Thr Leu Gly Ala Ile Tyr Gly Gly Leu Lys Ser
                435                 440                 445

Ala Tyr Asn Ile Cys Lys Ile Leu Gly Lys Glu Glu His Asp Ile Gln
                450                 455                 460

Asn Trp Lys Glu Ser Met Asp Phe Leu Lys Asn Glu Met Val Asp Arg
465                 470                 475                 480

Leu Tyr Leu Lys Asp Glu Asn Arg Phe Ala Lys Ser Leu Asp Pro Leu
                485                 490                 495

Asp Lys Ala Leu Asp Ala Ser Ile Leu Gly Leu Ser Phe Pro Tyr Asn
                500                 505                 510

Leu Val Pro Val Asp Asp Pro Arg Met Ile Ser Thr Ala Asn Gln Ile
                515                 520                 525

Glu Asn Ala Phe Lys Tyr Lys Val Gly Ile Gly Arg Tyr Pro Glu
                530                 535                 540

Asp Val Tyr Phe Gly Gly Asn Pro Trp Ile Ile Thr Thr Ile Trp Leu
545                 550                 555                 560

His Met Tyr Tyr Glu Asn Leu Ile Lys Ser Leu Ser Lys His Gly Lys
                565                 570                 575

Asn Ala Ile His Ser Asp Gln Ile Pro Asp Ser Ser Gly Asp Leu Lys
                580                 585                 590

Asp Phe Val Ser Ile Ile Gly Ser Ile Glu Asn His Gly Glu Lys Ser
                595                 600                 605

Asp Glu Thr Pro Ser Ser Asp Thr Leu Leu Thr Tyr Ala Gln Lys Cys
                610                 615                 620

Asn Asn Leu Phe Asp Trp Thr Leu Lys Tyr Asn Phe Asn Glu Leu Phe
625                 630                 635                 640

Pro Glu Gln Val His Lys Asp Leu Gly Ala Pro Ile Ser Ala Ile Pro
                645                 650                 655

Leu Gly Trp Ser His Ala Met Val Ile Ala Ile His Gly Asn Phe
                660                 665                 670

Asp Ile Leu Ile Pro
                675

<210> SEQ ID NO 13
<211> LENGTH: 1779
<212> TYPE: DNA
<213> ORGANISM: Unknown
<220> FEATURE:
<223> OTHER INFORMATION: Obtained from an environmental sample
```

<400> SEQUENCE: 13

```
atgattgttg gtaataatag ctttttatgt aagataggggg atcatggaga aattgaatat      60
gcattctacc cccatgttgg ttatgaacta cattttttg atagttcttt agctatatat     120
gataaagaaa ttatgtggat atgggataaa gagtggagtg tatatcagaa atatattgag     180
gacactaata tattcaaaac tactttagaa aatgagaata tcatatttgt tataaaagat     240
ttagtcccaa tttcacataa tgtattaatt aggagagttt tcattaaaaa taaacttcca     300
tataattata attttaaact attttctat gaaaatctta gaattggaga acatccttca      360
gaaaatacag ttaagttttt agatgattgt atagttaaat ttaatggcaa atatactttt     420
tgtataagca gtgataaaaa aataaattca tatcagtgtg gaaatagata tagtgaaaaa     480
tctgcttata agatattga aaatggttta ttatctgaaa atcctgaaag tgttggagtt      540
ctaactgaca gtgctattga atgggatata gatttaaaac cacatggaaa agtagcattt     600
aacatctaca tctttcctca tattggaaat aatatagaga ttataaaaaa tcagttaaat     660
attattaaaa atctctcttc tgaaataaaa aatatatctc taaattattg gaagagttct     720
tttgatataa aaggttatct atttaatgaa aaatatttaa aattagcaaa aagggcttta    780
atgatactaa caatgctttc tgacaaaaat ggaggaatta tagcctctcc atctattcat    840
cctgattata gatatgtttg gggtagagat ggaagttata tggctgtggc attatccatt    900
tatgaaataa aaaacattcc atggaggttc ttccattta tgtctaaagt ccagaatctt     960
gatggttcat ggttacaaaa ctattataca gatggtaaac caagattaac tgctttacaa   1020
atagatcaaa taggttcagt tctttgggct atggaagttt attatagaac tacaggtgat   1080
agagagtttg ttaaaaaatt ctgggaaact attgagaaag ctggaaattt cttatataat   1140
gcttcattat ctttaatgcc atgttttgat ctttgggaag aaaaatatgg ggtattttca   1200
tatactttag gagcaatgta tggaggatta agggcaggat gtagtttagc taaagctata   1260
gaagagaaaa aagaagattg gaaaaaggct ttagataaat taagaaagga tgttgattta   1320
ttatatttaa gtgatgaaga aagatttgtt aaatctatta acccattgaa caaagagatt   1380
gatacaagta tattagggct tagctatcca tttggactag ttaaagttaa tgatgaagaa   1440
atgataaaaa ctgctgaagc catagaaaaa gcttttaaat acaaagttgg aggtattggg   1500
agatatccat ctgatgttta ttttggagga atccttggaa ttataacaac actttggtta   1560
gctttatatt atagaagact atttattact acaaatgata gaaaatattt agaaaaatca   1620
aaaaagctat ttaattgggt tattaaccat atctatctat tccctgaaca gatacataaa   1680
gaattagcta ttcctgtatc agctatgcct ttaggttgga gttgtgctat gctgttattc   1740
tatctatata aaaatgatga cataatagtg ataaaatga                          1779
```

<210> SEQ ID NO 14
<211> LENGTH: 592
<212> TYPE: PRT
<213> ORGANISM: Unknown
<220> FEATURE:
<223> OTHER INFORMATION: Obtained from an environmental sample

<400> SEQUENCE: 14

```
Met Ile Val Gly Asn Asn Ser Phe Leu Cys Lys Ile Gly Asp His Gly
  1               5                  10                  15

Glu Ile Glu Tyr Ala Phe Tyr Pro His Val Gly Tyr Glu Leu His Phe
             20                  25                  30

Phe Asp Ser Ser Leu Ala Ile Tyr Asp Lys Glu Ile Met Trp Ile Trp
```

```
                 35                  40                  45
Asp Lys Glu Trp Ser Val Tyr Gln Lys Tyr Ile Glu Asp Thr Asn Ile
                 50                  55                  60

Phe Lys Thr Thr Leu Glu Asn Glu Asn Ile Ile Phe Val Ile Lys Asp
 65                  70                  75                  80

Leu Val Pro Ile Ser His Asn Val Leu Ile Arg Arg Val Phe Ile Lys
                 85                  90                  95

Asn Lys Leu Pro Tyr Asn Tyr Asn Phe Lys Leu Phe Phe Tyr Glu Asn
                100                 105                 110

Leu Arg Ile Gly Glu His Pro Ser Glu Asn Thr Val Lys Phe Leu Asp
                115                 120                 125

Asp Cys Ile Val Lys Phe Asn Gly Lys Tyr Thr Phe Cys Ile Ser Ser
                130                 135                 140

Asp Lys Lys Ile Asn Ser Tyr Gln Cys Gly Asn Arg Tyr Ser Glu Lys
145                 150                 155                 160

Ser Ala Tyr Lys Asp Ile Glu Asn Gly Leu Leu Ser Glu Asn Pro Glu
                165                 170                 175

Ser Val Gly Val Leu Thr Asp Ser Ala Ile Glu Trp Asp Ile Asp Leu
                180                 185                 190

Lys Pro His Gly Lys Val Ala Phe Asn Ile Tyr Ile Phe Pro His Ile
                195                 200                 205

Gly Asn Asn Ile Glu Ile Ile Lys Asn Gln Leu Asn Ile Ile Lys Asn
                210                 215                 220

Leu Ser Ser Glu Ile Lys Asn Ile Ser Leu Asn Tyr Trp Lys Ser Ser
225                 230                 235                 240

Phe Asp Ile Lys Gly Tyr Leu Phe Asn Glu Lys Tyr Leu Lys Leu Ala
                245                 250                 255

Lys Arg Ala Leu Met Ile Leu Thr Met Leu Ser Asp Lys Asn Gly Gly
                260                 265                 270

Ile Ile Ala Ser Pro Ser Ile His Pro Asp Tyr Arg Tyr Val Trp Gly
                275                 280                 285

Arg Asp Gly Ser Tyr Met Ala Val Ala Leu Ser Ile Tyr Gly Ile Lys
                290                 295                 300

Asn Ile Pro Trp Arg Phe His Phe Met Ser Lys Val Gln Asn Leu
305                 310                 315                 320

Asp Gly Ser Trp Leu Gln Asn Tyr Tyr Thr Asp Gly Lys Pro Arg Leu
                325                 330                 335

Thr Ala Leu Gln Ile Asp Gln Ile Gly Ser Val Leu Trp Ala Met Glu
                340                 345                 350

Val Tyr Tyr Arg Thr Thr Gly Asp Arg Glu Phe Val Lys Lys Phe Trp
                355                 360                 365

Glu Thr Ile Glu Lys Ala Gly Asn Phe Leu Tyr Asn Ala Ser Leu Ser
                370                 375                 380

Leu Met Pro Cys Phe Asp Leu Trp Glu Glu Lys Tyr Gly Val Phe Ser
385                 390                 395                 400

Tyr Thr Leu Gly Ala Met Tyr Gly Gly Leu Arg Ala Gly Cys Ser Leu
                405                 410                 415

Ala Lys Ala Ile Glu Glu Lys Leu Glu Asp Trp Lys Lys Ala Leu Asp
                420                 425                 430

Lys Leu Lys Lys Asp Val Asp Leu Leu Tyr Leu Ser Asp Glu Glu Arg
                435                 440                 445

Phe Val Lys Ser Ile Asn Pro Leu Asn Lys Glu Ile Asp Thr Ser Ile
                450                 455                 460
```

```
Leu Gly Leu Ser Tyr Pro Phe Gly Leu Val Lys Val Asn Asp Glu Arg
465                 470                 475                 480

Met Ile Lys Thr Ala Glu Ala Ile Glu Lys Ala Phe Lys Tyr Lys Val
            485                 490                 495

Gly Gly Ile Gly Arg Tyr Pro Ser Asp Val Tyr Phe Gly Gly Asn Pro
            500                 505                 510

Trp Ile Ile Thr Thr Leu Trp Leu Ala Leu Tyr Tyr Arg Arg Leu Phe
            515                 520                 525

Ile Thr Thr Asn Asp Arg Lys Tyr Leu Glu Lys Ser Lys Lys Leu Phe
            530                 535                 540

Asn Trp Val Ile Asn His Ile Tyr Leu Phe Pro Glu Gln Ile His Lys
545                 550                 555                 560

Glu Leu Ala Ile Pro Val Ser Ala Met Pro Leu Gly Trp Ser Cys Ala
                565                 570                 575

Met Leu Leu Phe Tyr Leu Tyr Lys Asn Asp Asp Ile Ile Val Ile Lys
                580                 585                 590
```

<210> SEQ ID NO 15
<211> LENGTH: 2121
<212> TYPE: DNA
<213> ORGANISM: Unknown
<220> FEATURE:
<223> OTHER INFORMATION: DNA derived from Bacteria

<400> SEQUENCE: 15

```
atgaaattga atagaaaact tataaaatat ttacccgtac tatttcttgc gtccagtgtg      60
ctaagtggat gcgctaacaa taatatatca aacattaaaa ttgagagatt gaataatgta     120
caagcagtaa atggccctgg agaggctgat acttgggcta agctcagaa acaaggtgta      180
gggactgcaa acaactatac ttccaaagta tggtttacca ttgcagacgg ggggatatct     240
gaggtttact atccgactat agatactgct gatgtaaagg atattaaatt ttttgtgaca     300
gatggaaaaa cgtttgtctc agatgagaca aaagacacaa taaccaaagt cgaaaagttt     360
actgaaaaat cgttggggta taaaatcatt aacacagata agaagggag atataagata      420
actaagaaa tatttacgga tgtaaagagg aattctctcg taattaaaac gaagtttgaa      480
gccttaaaag gcaatgttga tgattacagg ctttacgtaa tgtgtgatcc tcatgtaaaa     540
aatcagggca aatataatga aggatatgca gttaaggcaa atggcaatgt tgcgctaatt     600
gctgaaagag atggaattta cactgcattg tcatctgaca taggatggaa aaagtattcg     660
ataggtttatt ataagtaaa tgacattgag accgatcttt ataaaaatat gcaaatgact     720
tacaattacg acagtgcaag aggcaacatc atagaaggtg ctgagataga tcttaagaaa     780
aacaggcaat ttgaaatcgt tctgtctttc ggacagagtg aagacgaggc agtaaaaaca     840
aacatggaaa ctttaaatga taattatgac agcttaaaga aagcgtatat agaccaatgg     900
gagaagtatt gcgatagcct taatgactt ggaggaaaag caaattcact gtattttaac      960
agtatgatga tattaaaggc cagtgaagac aagacaaaca aaggtgctta tatagcatcg    1020
ctatctattc cgtggggtga tggccaagaa gatgacaata ttggtggcta ccatctcgta    1080
tggtcaagag atctgtacca tgtagcgaat gcatttatg ttgctggtga tactgattcg     1140
gcaaatagag cactggatta tttagacaaa gtagtgaaag acaatggaat gattcctcaa    1200
aatacatgga taaatggaag gcctattgg acaggcatac agcttgatga gcaggcggat     1260
ccaataatat taagctatag gttgaaaaga tacgatctct atgaaagtct tgttaagcct    1320
```

-continued

```
ttggcggatt tcatcatgaa aataggccct aagacgggac aagaaagatg ggaagaaata    1380
ggtggatatt cgccagcaac attggcttca gaagtagctg gacttacatg tgctgcgtat    1440
atagctgaac aaaataagga cttttgaatct gctaaaaaat atcaagaaaa ggcggataat    1500
tggcaaaggc ttattgacaa cctaacttac acagaaaaag gcccattggg agatggtcac    1560
tattatataa ggatagcagg gcttccagat ccaaatgccg atttcatgat aagcatagcg    1620
aatggcggtg gtgtatacga ccaaaaagaa atcgtggatc caagttttct ggaacttgta    1680
aggcttggag taaaatcagc agatgaccct aaaatactaa atacgctgaa agtcgtggat    1740
gaaacaataa aagtcgatac accgaaagga ccatcatggt ataggtataa tcatgatgga    1800
tatggtgaga tgtctaagac agaactatat catgggacag gaaaaggaag attgtggcca    1860
ctgcttacag gtgagagagg catgtacgaa attgctgcag agtatgatga tgtaataatt    1920
ataaagacaa gaataggttt attgaaaggc tcaaggataa gatttgagta cgatatagtg    1980
aaagaagatg aaaataagct tttagcacaa ggtatgacag aacacccatt tacgacactt    2040
gacagaaaac ctgtaaatat aaaaaagatt ttgcctcatg tttatgaaat gttgaacaaa    2100
tgctatgatg atggtgttta g                                              2121
```

<210> SEQ ID NO 16
<211> LENGTH: 706
<212> TYPE: PRT
<213> ORGANISM: Unknown
<220> FEATURE:
<223> OTHER INFORMATION: Protein derived from Bacteria

<400> SEQUENCE: 16

```
Met Lys Leu Asn Arg Lys Leu Ile Lys Tyr Leu Pro Val Leu Phe Leu
1               5                  10                  15

Ala Ser Ser Val Leu Ser Gly Cys Ala Asn Asn Ile Ser Asn Ile
            20                  25                  30

Lys Ile Glu Arg Leu Asn Asn Val Gln Ala Val Asn Gly Pro Gly Glu
        35                  40                  45

Ala Asp Thr Trp Ala Lys Ala Gln Lys Gln Gly Val Gly Thr Ala Asn
    50                  55                  60

Asn Tyr Thr Ser Lys Val Trp Phe Thr Ile Ala Asp Gly Gly Ile Ser
65                  70                  75                  80

Glu Val Tyr Tyr Pro Thr Ile Asp Thr Ala Asp Val Lys Asp Ile Lys
                85                  90                  95

Phe Phe Val Thr Asp Gly Lys Thr Phe Val Ser Asp Glu Thr Lys Asp
            100                 105                 110

Thr Ile Thr Lys Val Glu Lys Phe Thr Glu Lys Ser Leu Gly Tyr Lys
        115                 120                 125

Ile Ile Asn Thr Asp Lys Glu Gly Arg Tyr Lys Ile Thr Lys Glu Ile
    130                 135                 140

Phe Thr Asp Val Lys Arg Asn Ser Leu Val Ile Lys Thr Lys Phe Glu
145                 150                 155                 160

Ala Leu Lys Gly Asn Val Asp Asp Tyr Arg Leu Tyr Val Met Cys Asp
                165                 170                 175

Pro His Val Lys Asn Gln Gly Lys Tyr Asn Glu Gly Tyr Ala Val Lys
            180                 185                 190

Ala Asn Gly Asn Val Ala Leu Ile Ala Glu Arg Asp Gly Ile Tyr Thr
        195                 200                 205

Ala Leu Ser Ser Asp Ile Gly Trp Lys Lys Tyr Ser Ile Gly Tyr Tyr
    210                 215                 220
```

-continued

```
Lys Val Asn Asp Ile Glu Thr Asp Leu Tyr Lys Asn Met Gln Met Thr
225                 230                 235                 240

Tyr Asn Tyr Asp Ser Ala Arg Gly Asn Ile Glu Gly Ala Glu Ile
            245                 250                 255

Asp Leu Lys Lys Asn Arg Gln Phe Glu Ile Val Leu Ser Phe Gly Gln
            260                 265                 270

Ser Glu Asp Glu Ala Val Lys Thr Asn Met Glu Thr Leu Asn Asp Asn
            275                 280                 285

Tyr Asp Ser Leu Lys Lys Ala Tyr Ile Asp Gln Trp Glu Lys Tyr Cys
    290                 295                 300

Asp Ser Leu Asn Asp Phe Gly Lys Ala Asn Ser Leu Tyr Phe Asn
305                 310                 315                 320

Ser Met Met Ile Leu Lys Ala Ser Glu Asp Lys Thr Asn Lys Gly Ala
                325                 330                 335

Tyr Ile Ala Ser Leu Ser Ile Pro Trp Gly Asp Gly Gln Glu Asp Asp
                340                 345                 350

Asn Ile Gly Gly Tyr His Leu Val Trp Ser Arg Asp Leu Tyr His Val
            355                 360                 365

Ala Asn Ala Phe Ile Val Ala Gly Asp Thr Asp Ser Ala Asn Arg Ala
370                 375                 380

Leu Asp Tyr Leu Asp Lys Val Val Lys Asp Asn Gly Met Ile Pro Gln
385                 390                 395                 400

Asn Thr Trp Ile Asn Gly Arg Pro Tyr Trp Thr Gly Ile Gln Leu Asp
                405                 410                 415

Glu Gln Ala Asp Pro Ile Ile Leu Ser Tyr Arg Leu Lys Arg Tyr Asp
            420                 425                 430

Leu Tyr Glu Ser Leu Val Lys Pro Leu Ala Asp Phe Ile Met Lys Ile
            435                 440                 445

Gly Pro Lys Thr Gly Gln Glu Arg Trp Glu Glu Ile Gly Gly Tyr Ser
450                 455                 460

Pro Ala Thr Leu Ala Ser Glu Val Ala Gly Leu Thr Cys Ala Ala Tyr
465                 470                 475                 480

Ile Ala Glu Gln Asn Lys Asp Phe Glu Ser Ala Lys Lys Tyr Gln Glu
                485                 490                 495

Lys Ala Asp Asn Trp Gln Arg Leu Ile Asp Asn Leu Thr Tyr Thr Glu
            500                 505                 510

Lys Gly Pro Leu Gly Asp Gly His Tyr Tyr Ile Arg Ile Ala Gly Leu
            515                 520                 525

Pro Asp Pro Asn Ala Asp Phe Met Ile Ser Ile Ala Asn Gly Gly Gly
530                 535                 540

Val Tyr Asp Gln Lys Glu Ile Val Asp Pro Ser Phe Leu Glu Leu Val
545                 550                 555                 560

Arg Leu Gly Val Lys Ser Ala Asp Pro Lys Ile Leu Asn Thr Leu
            565                 570                 575

Lys Val Val Asp Glu Thr Ile Lys Val Asp Thr Pro Lys Gly Pro Ser
            580                 585                 590

Trp Tyr Arg Tyr Asn His Asp Gly Tyr Gly Glu Met Ser Lys Thr Glu
            595                 600                 605

Leu Tyr His Gly Thr Gly Lys Gly Arg Leu Trp Pro Leu Leu Thr Gly
    610                 615                 620

Glu Arg Gly Met Tyr Glu Ile Ala Ala Glu Tyr Asp Asp Val Ile Ile
625                 630                 635                 640
```

```
-continued

Ile Lys Thr Arg Ile Gly Leu Leu Lys Gly Ser Arg Ile Arg Phe Glu
                645                 650                 655

Tyr Asp Ile Val Lys Glu Asp Glu Asn Lys Leu Leu Ala Gln Gly Met
            660                 665                 670

Thr Glu His Pro Phe Thr Thr Leu Asp Arg Lys Pro Val Asn Ile Lys
        675                 680                 685

Lys Ile Leu Pro His Val Tyr Glu Met Leu Asn Lys Cys Tyr Asp Asp
    690                 695                 700

Gly Val
705
```

What is claimed is:

1. A method for hydrolyzing a starch comprising:
   (a) providing a starch;
   (b) providing a polypeptide having glucoamylase activity, wherein the polypeptide is at least 85% identical to the amino acid sequence of SEQ ID NO:12; and
   (c) contacting the starch of (a) with the polypeptide of (b) wherein the polypeptide hydrolyzes the starch.

2. The method of claim 1, wherein the starch is from rice, corn, barley, wheat, legumes, or potato.

3. The method of claim 1, wherein the hydrolysis of starch forms an animal feed product.

4. The method of claim 1, wherein the hydrolysis of starch forms a food product.

5. The method of claim 1, wherein the hydrolysis of starch is for desizing the fabric.

6. The method of claim 1, wherein the hydrolysis of starch is for paper processing.

7. A method of claim 1, wherein the hydrolysis of starch produces a high-maltose or a high-glucose syrup.

8. A method of claim 1, wherein hydrolysis of starch in a baked product prevents staling of the baked product.

9. The method as set forth in claim 8, wherein the baked product is bread.

10. A method of claim 1, wherein the hydrolysis of starch is for alcohol production.

11. A method of claim 1, wherein the hydrolysis of starch is for a brewing process.

12. The method as set forth in claim 11, wherein a composition comprising the starch is in a wort used for brewing beer.

13. The method of claim 1, wherein the hydrolysis of starch is used for saccharification.

* * * * *